(12) United States Patent
Fujii et al.

(10) Patent No.: US 8,410,059 B2
(45) Date of Patent: *Apr. 2, 2013

(54) CXCR4 ANTAGONIST AND USE THEREOF

(75) Inventors: Nobutaka Fujii, Shiga (JP); Hirokazu Tamamura, Kyoto (JP); Akira Hori, Hyogo (JP)

(73) Assignee: Biokine Therapeutics Ltd., Nes Ziona (IL)

( * ) Notice: Subject to any disclaimer, the term of this patent is extended or adjusted under 35 U.S.C. 154(b) by 0 days.

This patent is subject to a terminal disclaimer.

(21) Appl. No.: 13/178,737

(22) Filed: Jul. 8, 2011

(65) Prior Publication Data

US 2011/0269686 A1 Nov. 3, 2011

Related U.S. Application Data

(62) Division of application No. 12/172,007, filed on Jul. 11, 2008, now Pat. No. 8,017,585, which is a division of application No. 10/525,838, filed as application No. PCT/JP03/10753 on Aug. 26, 2003, now Pat. No. 7,423,007.

(30) Foreign Application Priority Data

Aug. 27, 2002 (JP) ................................ 2002-247843

(51) Int. Cl.
*A61K 38/10* (2006.01)
*A61K 38/00* (2006.01)
*C07K 7/08* (2006.01)
*C07K 7/00* (2006.01)

(52) U.S. Cl. .................... 514/19.3; 514/19.4; 514/19.6; 514/19.8; 514/16.6; 514/21.5; 530/300; 530/327

(58) Field of Classification Search .......................... None
See application file for complete search history.

(56) References Cited

U.S. PATENT DOCUMENTS

| | | | |
|---|---|---|---|
| 4,179,337 A | 12/1979 | Davis et al. | |
| 4,342,828 A | 8/1982 | Takaku et al. | |
| 5,206,018 A | 4/1993 | Sehgal et al. | |
| 5,250,732 A | 10/1993 | Kogan et al. | |
| 5,492,126 A | 2/1996 | Hennige et al. | |
| 5,595,756 A * | 1/1997 | Bally et al. .................... | 424/450 |
| 6,128,522 A | 10/2000 | Acker et al. | |
| 6,365,583 B1 | 4/2002 | MacFarland et al. | |
| 6,576,875 B1 | 6/2003 | Kleffner et al. | |
| 6,875,738 B1 | 4/2005 | Clark-Lewis et al. | |
| 6,946,445 B1 | 9/2005 | Clark-Lewis et al. | |
| 7,138,488 B2 | 11/2006 | Fujii | |
| 7,169,750 B2 | 1/2007 | Bridger et al. | |
| 7,291,631 B2 | 11/2007 | Bridger et al. | |
| 7,423,007 B2 | 9/2008 | Fujii et al. | |
| 7,595,298 B2 | 9/2009 | Fujii | |
| 7,630,750 B2 | 12/2009 | Liang et al. | |
| 8,017,585 B2 | 9/2011 | Fujii et al. | |
| 2002/0156034 A1 | 10/2002 | Tudan et al. | |
| 2004/0116655 A1 | 6/2004 | Fujii | |
| 2004/0209921 A1 | 10/2004 | Bridger et al. | |
| 2005/0002939 A1 | 1/2005 | Zlotnik et al. | |
| 2005/0043367 A1 | 2/2005 | Bridger et al. | |
| 2006/0008465 A1 | 1/2006 | Steinaa et al. | |
| 2006/0079492 A1 | 4/2006 | Ahlem et al. | |
| 2006/0264378 A1 | 11/2006 | Fujii et al. | |
| 2006/0264605 A1 | 11/2006 | Fujii | |
| 2007/0129760 A1 | 6/2007 | Demarais et al. | |
| 2007/0167459 A1 | 7/2007 | Habashita et al. | |
| 2009/0181897 A1 | 7/2009 | Fujii et al. | |
| 2010/0143334 A1 | 6/2010 | Peled et al. | |
| 2010/0166715 A1 | 7/2010 | Peled et al. | |
| 2010/0184694 A1 | 7/2010 | Peled et al. | |
| 2010/0222256 A1 | 9/2010 | Fujii | |
| 2012/0094907 A1 | 4/2012 | Abraham et al. | |
| 2012/0207748 A1 | 8/2012 | Peled et al. | |

FOREIGN PATENT DOCUMENTS

| | | |
|---|---|---|
| CA | 1297007 | 3/1992 |
| EP | 0243153 | 10/1987 |
| EP | 0396158 | 11/1990 |
| EP | 0215126 | 7/1991 |
| EP | 0220520 | 9/1991 |
| EP | 0459516 | 12/1991 |
| EP | 0459795 | 12/1991 |
| EP | 0231819 | 4/1992 |
| EP | 0355811 | 12/1993 |
| EP | 0373679 | 6/1994 |
| EP | 0331186 | 8/1994 |
| EP | 0344796 | 9/1994 |
| EP | 0263490 | 1/1995 |
| EP | 0230980 | 3/1996 |
| EP | 0401384 | 3/1996 |
| EP | 0272703 | 10/1997 |
| EP | 0370205 | 7/1998 |
| EP | 0459630 | 8/1998 |
| EP | 0217404 | 1/1999 |
| EP | 0237545 | 8/1999 |
| EP | 0169566 | 7/2000 |
| EP | 0335423 | 3/2003 |
| EP | 1323730 | 7/2003 |
| EP | 0473268 | 10/2003 |
| EP | 2058395 | 5/2009 |
| JP | 2002-506830 | 3/2002 |

(Continued)

OTHER PUBLICATIONS

Sporn MB, Suh N, "Chemoprevention of cancer," Carcinogenesis, 2000, 21(3): 525-530; Attached also is the same journal article as an HTML version for cleaner scan, pp. 1-13.*
Cancer Drug Design and Discovery Neidle, Stephen, ed. (Elsevier/Academic Press, 2008) pp. 427-431.*
European Search Report and the European Search Opinion Dated Feb. 3, 2012 From the European Patent Office Re. Application No. 10176632.7.
International Preliminary Report on Patentability Dated Aug. 19, 2004 From the International Preliminary Examining Authority Re. Application No. PCT/JP2003/010753.
International Search Report Dated Nov. 4, 2003 From the International Searching Authority Re. Application No. PCT/JP2003/010753.

(Continued)

*Primary Examiner* — Julie Ha

(57) ABSTRACT

Therapeutic drugs for cancer and chronic rheumatoid arthritis which contain a peptide having a CXCR4 antagonism, its amide, its ester or its salt are described. Also, the present invention provides a novel peptide having a CXCR4 antagonism, its amide, its ester and its salt.

3 Claims, 7 Drawing Sheets

FOREIGN PATENT DOCUMENTS

| WO | WO 91/07988 | 6/1991 |
|---|---|---|
| WO | WO 93/15211 | 8/1993 |
| WO | 95/10534 | 4/1995 |
| WO | WO 95/10534 | 4/1995 |
| WO | 99//47158 | 9/1999 |
| WO | WO 99/47158 | 9/1999 |
| WO | 00/06086 A1 | 2/2000 |
| WO | WO 00/09152 | 2/2000 |
| WO | 01/38352 | 5/2001 |
| WO | WO 01/64716 | 9/2001 |
| WO | 01/85196 | 11/2001 |
| WO | WO 01/85196 | 11/2001 |
| WO | 02/20561 A1 | 3/2002 |
| WO | WO 02/20561 | 3/2002 |
| WO | WO 2004/020462 | 3/2004 |
| WO | WO 2004/024178 | 3/2004 |
| WO | WO 2004/087068 | 10/2004 |
| WO | WO 2008/017025 | 2/2008 |
| WO | WO 2008/075369 | 6/2008 |
| WO | WO 2008/075370 | 6/2008 |
| WO | WO 2008/075371 | 6/2008 |
| WO | WO 2010/146578 | 12/2010 |
| WO | WO 2010/146584 | 12/2010 |
| WO | WO 2012/095849 | 7/2012 |

OTHER PUBLICATIONS

Communication Under Rule 71(3) EPC Dated Apr. 16, 2012 From the European Patent Office Re. Application No. 03791288.8.

Hatse et al., CXC-chemokine receptor 4 as a potential new therapeutic target for neuroblastoma and breast cancer, International Journal of Canc. Suppl, 2002: 13:349.

Hiramatsu et al., Synthesis of CXCR4 antagonists, T140 derivatives with improved biostability, and their SAR study. Peptide Science 203; 2002: 213-216 (Yamada, T, ed.).

Mod et al., Involvement of Stromal cell-Derived Factor 1 and CXCR4 receptor system in pancreatic cancer. Gastroenterology, 2002; 122(4), Suppl 1:A490. (Abstract T1608).

Tamamura et al., Downsizing of an HIV-cell fusion inhibitor, T22([Tyr5, 12, Lys7]-polyphemusin II), with the maintenance of anti-HIV activity and solution structure. Bioorg Med.Chem. 1998, 6:473-9.

Tamamura et al., T140 analogs as CXCR4 antagonists identified as anti-metastatic agents in the treatment of breast cancer. FEBS Lett. 2003 (Aug. 28) 550:79-83.

Tamamura H, Arakaki R, Funakoshi H, Imai M, Otaka A, Ibuka T, Nakashima H, Murakami T, Waki M, Matsumoto A, Yamamoto N and Fujii N, Effective lowly cytotoxic analgos of an HIV-cell fusion inhibitor, T22([Tyr 5 12, Lys7]- polyphemusin II), Bioorg Med Chem, 1998, 6:231-238.

Tamamura H, Xu Y, Hattori T, Zhang X, Arakaki R, Kanbara K, Omagari A, Otaka A, Ibuka T, Yamamoto N, Nakashima H and Fujii N, A Low-Molecular-Weight Inhibitor against the Chemokine Receptor CXCR4: A Strong Anti-HIV Peptide T140, BBRC, 1998, 253:877-882.

Introduction to Cancer from the Merck manual, Accessed Jun. 26, 2007.

Clinical Aspects of Cancer from the Merck manual, Accessed Jun. 26, 2007.

Auerbach R, Akhtar N, Lewis RL, Shinners BL, Angiogenesis assays: Problems and pitfalls, Cancer and Metastasis Reviews, 2000, 19: 167-172.

Gura T, Cancer Models: Systems for Identifying New Drugs Are Often Faulty, Science, 1997, 278 (5340): 1041-1042, enclosed pp. 1-5.

Tamamura et al., "Efficient Analogs of an Anti-HIV Peptide, T22 ([Tyr 5, 12, Lys71)-Polyphemusin II), Having Low Cytotoxicity" Peptide Science-Present and Future 1:427-429, 1997.

Tamamura et al., "Development of Specific CXCR4 Inhibitors Possessing High Selectivity Indexes as well as Complete Stability in Serum Based on an Anti-HIV Peptide T140" Bioorganic & Medical Chemistry Letters 11:1897-1902, 2001.

Jain, "Barriers to Drug Delivery in Solid Tumors" Scientific American, 58-65, 1994.

Rheumatoid Arthritis from the Merck Manual, 18th Ed., 2005.

Koshiba, Takatomo et al., (2000) Expression of Stromal Cell-derived Factor 1 and CXCR4 Ligand Receptor System in Pancreatic Cancer: A Possible Role for Tumor Progression. Clin Cancer Res. 6(9)3530-3535.

Tamamura, Hirokazu et al., (2000) Pharmacophore identification of a specific CXCR4 inhibitor, T140, leads to development of effective anti-HIV agents with very high selectivity indexes. Bioorg Med Chem Lett 10(23):2633-2637.

Tamamura, Hirokazu et al., (2002) Certification of the critical importance of L-3-(2-naphthyl)alanine at position 3 of a specific CXCR4 inhibitor, T140, leads to an exploratory performance of its downsizing study. Bioorganic & Medicinal Chemistry 10(5):1417-1426.

Fujii, Nobutaka et al. Research Report (2001) Manufacturing and Practical Application of a Strategic Anti-AIDS Agent with a Base Molecule as an HIV-2 Receptor Antagonist. Year 2000 AIDS Drug Development Research, Japan Health Sciences Foundation.

Fujii, Nobutaka and Tamamura, Hirokazu (2001) Peptide-lead CXCR4 antagonists with high anti-HIV activity. Curr Opin Investig Drugs 2(9):1198-1202.

Matthys, Patrick et al., (2001) AMD3100, a potent and specific antagonist of the stromal cell-derived factor-1 chemokine receptor CXCR4, inhibits autoimmune joint inflammation in IFN-gamma receptor-deficient mice. J Immunol 167(8):4686-4692.

Tamamura, Hirokazu (2001) Development of selective antagonists against an HIV second receptor. Yakugaku Zasshi 121(11):781-792 (abstract in English).

Amendment Dated May 15, 2008 After Notice of Allowance of Apr. 14, 2008 From the US Patent and Trademark Office Re. U.S. Appl. No. 10/525,838.

Communication Pursuant to Article 94(3) EPC Dated Oct. 4, 2010 From the European Patent Office Re. Application No. 03791288.8.

Communication Pursuant to Article 94(3) EPC Dated Apr. 9, 2008 From the European Patent Office Re. Application No. 03791288.8.

Communication Pursuant to Article 94(3) EPC Dated Dec. 15, 2008 From the European Patent Office Re. Application No. 03791288.8.

Communication Pursuant to Article 94(3) EPC Dated Sep. 15, 2009 From the European Patent Office Re. Application No. 03791288.8.

Notice of Allowance Dated Apr. 11, 2011 From the US Patent and Trademark Office Re. U.S. Appl. No. 12/172,007.

Notice of Allowance Dated Apr. 14, 2008 From the US Patent and Trademark Office Re. U.S. Appl. No. 10/525,838.

Official Action Dated Jul. 1, 2010 From the US Patent and Trademark Office Re. U.S. Appl. No. 12/172,007.

Official Action Dated Jul. 11, 2007 From the US Patent and Trademark Office Re. U.S. Appl. No. 10/525,838.

Official Action Dated Jan. 24, 2011 From the US Patent and Trademark Office Re. U.S. Appl. No. 12/172,007.

Requisition by the Examiner Dated Oct. 17, 2011 From the Canadian Intellectual Property Office Re. Appllication No. 2,537,158.

Requisition by the Examiner Dated May 25, 2010 From the Canadian Intellectual Property Office Re. Application No. 2,537,158.

Response Dated Nov. 1, 2010 to Official Action of Jul. 1, 2010 From the US Patent and Trademark Office Re. U.S. Appl. No. 12/172,007.

Response Dated Jan. 8, 2008 to Official Action of Jul. 11, 2007 From the US Patent and Trademark Office Re. U.S. Appl. No. 10/525,838.

Response Dated Jun. 10, 2009 to Restriction Official Action of Mar. 26, 2009 From the US Patent and Trademark Office Re. U.S. Appl. No. 12/172,007.

Response Dated Oct. 12, 2010 to Communication Pursuant to Article 94(3) EPC of Oct. 4, 2010 From the European Patent Office Re. Application No. 03791288.8.

Response Dated Apr. 15, 2009 to Communication Pursuant to Article 94(3) EPC of Dec. 15, 2008 From the European Patent Office Re. Application No. 03791288.8.

Response Dated Oct. 15, 2008 to Communication Pursuant to Article 94(3) EPC of Apr. 9, 2008 From the European Patent Office Re. Application No. 03791288.8.

Response Dated Jan. 21, 2010 to Communication Pursuant to Article 94(3) EPC of Sep. 15, 2009 From the European Patent Office Re. Application No. 03791288.8.

Response Dated Mar. 23, 2011 to Official Action of Jan 24, 2011 From the US Patent and Trademark Office Re. U.S. Appl. No. 12/172,007.
Response Dated May 25, 2007 to Restriction Official Action of Feb. 6, 2007 From the US Patent and Trademark Office Re. U.S. Appl. No. 10/525,838.
Response Dated Nov. 25, 2011 to Requisition by the Examiner of May 25, 2010 From the Canadian Intellectual Property Office Re. Application No. 2,537,158.
Restriction Official Action Dated Feb. 6, 2007 From the US Patent and Trademark Office Re. U.S. Appl. No. 10/525,838.
Restriction Official Action Dated Mar. 26, 2009 From the US Patent and Trademark Office Re. U.S. Appl. No. 12/172,007.
Second Amendment Dated Jul. 14, 2008 to Amendment of May 15, 2008 After Notice of Allowance of Apr. 14, 2008 From the US Patent and Trademark Office Re. U.S. Appl. No. 10/525,838.
Supplementary Partial European Search Report Dated Nov. 28, 2007 From the European Patent Office Re. Application No. 03791288.8.
Tamamura et al. "Development of Specific CXCR4 Inhibitors Possessing High Selectivity Indexes as Well as Complete Stability in Serum Based on an Anti-HIV Peptide T140", Bioorganic & Medicinal Chemistry Letters, 11: 1897-1902, Jul. 23, 2001.
Response Dated Dec. 8, 2009 to Office Action of Aug. 11, 2009 From the Japanese Patent Office Re. Application No. 2003-301176.
Response Dated Jan. 31, 2011 to Office Action of Oct. 19, 2010 From the Japanese Patent Office Re. Application No. 2003-301176.
Translation of Office Action Dated Aug. 11, 2009 From the Japanese Patent Office Re. Application No. 2003-301176.
Translation of Office Action Dated Oct. 19, 2010 From the Japanese Patent Office Re. Application No. 2003-301176.
Koshiba et al. "Expression of Stromal Cell-Derived Factor 1 and CXCR4 Ligand Receptor System in Pancreatic Cancer: A Possible Role for Tumor Progression", Clinical Cancer Research, 6: 3530-3535, Sep. 2000.
Kucia et al. "Trafficking of Normal Stem Cells and Metastasis of Cancer Stem Cells Involve Similar Mechanisms: Pivotal Role of the SDF-1—CXCR4 Axis", Stem Cells, 23(7): 879-894, Aug. 2005.
Voermans et al. "Migratory Behavior of Leukemic Cells From Acute Myeloid Leukemia Patients", Leukemia, 16(4): 650-657, Apr. 2002.
Advisory Action Before the Filing of an Appeal Brief Dated Nov. 16, 2012 From the US Patent and Trademark Office Re. U.S. Appl. No. 12/520,699.
Communication Pursuant to Rule 69 EPC—Reminder Concerning Payment of the Designation Fee (Art. 79(2) EPC) and of the Examination Fee (Art. 94(1) EPC)—and Invitation Pursuant to Rule 70a(1) EPC Dated Mar. 12, 2012 From the European Patent Office Re. Application No. 10176632.7.
Communication Pursuant to Article 96(2) EPC Dated Feb. 6, 2006 From the European Patent Office Re. Application No. 10963414.6.
Communication Pursuant to Article 96(2) EPC Dated Mar. 17, 2005 From the European Patent Office Re. Application No. 10963414.6.
Communication Pursuant to Article 96(2) EPC Dated Jul. 18, 2006 From the European Patent Office Re. Application No. 10963414.6.
Communication Pursuant to Article 96(2) EPC Dated Jul. 26, 2007 From the European Patent Office Re. Application No. 10963414.6.
International Preliminary Report on Patentability Dated Apr. 19, 2002 From the International Preliminary Examining Authority Re. PCT/JP2001/007668.
International Preliminary Report on Patentability Dated Jun. 24, 2009 From the International Bureau of WIPO Re. Application No. PCT/IL2007/001596.
International Preliminary Report on Patentability Dated Jun. 24, 2009 From the International Bureau of WIPO Re. Application No. PCT/IL2007/001598.
International Preliminary Report on Patentability Dated Dec. 29, 2011 From the International Bureau of WIPO Re. Application No. PCT/IL2010/000466.
International Search Report and the Written Opinion Dated Jun. 4, 2008 From the International Searching Authority Re. Application No. PCT/IL2007/001598.
International Search Report and the Written Opinion Dated Dec. 5, 2008 From the International Searching Authority Re. Application No. PCT/IL2007/001596.

International Search Report and the Written Opinion Dated Oct. 15, 2010 From the International Searching Authority Re. Application No. PCT/IL2010/000466.
International Search Report and the Written Opinion Dated Jun. 24, 2009 From the International Searching Authority Re. Application No. PCT/IL2007/001597.
International Search Report and the Written Opinion Dated May 30, 2012 From the International Searching Authority Re. Application No. PCT/IL2012/050008.
International Search Report Dated Dec. 11, 2001 From the International Searching Authority Re. Application No. PCT/JP2001/007668.
Interview Summary Dated May 3, 2005 From the US Patent and Trademark Office Re. U.S. Appl. No. 10/363,209.
Interview Summary Dated Feb. 21, 2006 From the US Patent and Trademark Office Re. U.S. Appl. No. 10/363,209.
Notice of Allowance Dated Mar. 9, 2006 From the US Patent and Trademark Office Re. U.S. Appl. No. 10/363,209.
Notice of Allowance Dated May 21, 2009 From the US Patent and Trademark Office Re. U.S. Appl. No. 11/497,225.
Office Action Dated May 4, 2010 From the Israel Patent Office Re. Application No. 199468.
Office Action Dated May 4, 2010 From the Israel Patent Office Re. Application No. 199469.
Office Action Dated Sep 4, 2011 From the Israel Patent Office Re. Application No. 199468 and Its Translation Into English.
Office Action Dated Oct. 31, 2011 From the Israel Patent Office Re. Application No. 199469 and Its Translation Into English.
Official Action Dated Nov. 3, 2005 From the US Patent and Trademark Office Re. U.S. Appl. No. 10/363,209.
Official Action Dated May 4, 2012 From the US Patent and Trademark Office Re. U.S. Appl. No. 12/520,699.
Official Action Dated Mar. 5, 2012 From the US Patent and Trademark Office Re. U.S. Appl. No. 12/520,803.
Official Action Dated Jun. 15, 2005 From the US Patent and Trademark Office Re. U.S. Appl. No. 10/363,209.
Official Action Dated Jun. 25, 2012 From the US Patent and Trademark Office Re. U.S. Appl. No. 12/520,811.
Official Action Dated Aug. 28, 2008 From the US Patent and Trademark Office Re. U.S. Appl. No. 11/497,225.
Official Action Dated Dec. 28, 2011 From the US Patent and Trademark Office Re. U.S. Appl. No. 12/583,746.
Requisition—Sequence Listing Dated Jan. 5, 2011 From the Canadian Intellectual Property Office Re. Application No. 2,673,719.
Requisition by the Examiner Dated Jul. 6, 2012 From the Canadian Intellectual Property Office Re. Application No. 2,421,183.
Requisition by the Examiner Dated Mar. 8, 2011 From the Canadian Intellectual Property Office Re. Application No. 2,421,183.
Requisition by the Examiner Dated May 19, 2011 From the Canadian Intellectual Property Office Re. Application No. 2,421,183.
Requisition by the Examiner Dated Aug. 25, 2009 From the Canadian Intellectual Property Office Re. Application No. 2,421,183.
Respone Dated Jan. 4, 2012 to Office Action of Sep. 4, 2011 From the Israel Patent Office Re. Application No. 199468 and Its Translation Into English.
Response Dated Jul. 1, 2005 to Communication Pursuant to Article 96(2) EPC of Mar. 17, 2005 From the European Patent Office Re. Application No. 10963414.6.
Response Dated Feb. 3, 2006 to Official Action of Nov. 3, 2005 From the US Patent and Trademark Office Re. U.S. Appl. No. 10/363,209.
Response Dated Jun. 4, 2008 to Restriction Official Action of Apr. 8, 2008 From the US Patent and Trademark Office Re. U.S. Appl. No. 11/497,225.
Response Dated Sep. 7, 2011 to Requisition by the Examiner of Mar. 8, 2011 From the Canadian Intellectual Property Office Re. Application No. 2,421,183.
Response Dated May 9, 2006 to Communication Pursuant to Article 96(2) EPC of Feb. 6, 2006 From the European Patent Office Re. Application No. 10963414.6.
Response Dated Oct. 14, 2011 to Restriction Official Action of Sep. 14, 2011 From the US Patent and Trademark Office Re. U.S. Appl. No. 12/583,746.

Response Dated Sep. 15, 2005 to Official Action of Jun. 15, 2005 From the US Patent and Trademark Office Re. U.S. Appl. No. 10/363,209.
Response Dated Nov. 16, 2007 to Communication Pursuant to Article 96(2) EPC of Jul. 26, 2007 From the European Patent Office Re. Application No. 10963414.6.
Response Dated Apr. 18, 2005 to Restriction Official Action of Mar. 18, 2005 From the US Patent and Trademark Office Re. U.S. Appl. No. 10/363,209.
Response Dated Oct. 21, 2010 to Office Action of May 4, 2010 From the Israel Patent Office Re. Application No. 199468.
Response Dated Oct. 21, 2010 to Office Action of May 4, 2010 From the Israel Patent Office Re. Application No. 199469.
Response Dated Mar. 22, 2011 to Requisition—Sequence Listing of Jan. 5, 2011 From the Canadian Intellectual Property Office Re. Application No. 2,673,719.
Response Dated Feb. 24, 2010 to Requisition by the Examiner of Aug. 25, 2009 From the Canadian Intellectual Property Office Re. Application No. 2,421,183.
Response Dated Jan. 26, 2009 to Official Action of Aug. 28, 2008 From the US Patent and Trademark Office Re. U.S. Appl. No. 11/497,225.
Response Dated Jan. 29, 2007 to Communication Pursuant to Article 96(2) EPC of Jul. 18, 2006 From the European Patent Office Re. Application No. 10963414.6.
Response Dated Jun. 30, 2010 to Requisition by the Examiner of May 19, 2011 From the Canadian Intellectual Property Office Re. Application No. 2,421,183.
Restriction Official Action Dated Mar. 1, 2012 From the US Patent and Trademark Office Re. U.S. Appl. No. 12/520,699.
Restriction Official Action Dated Apr. 8, 2008 From the US Patent and Trademark Office Re. U.S. Appl. No. 11/497,225.
Restriction Official Action Dated Sep. 14, 2011 From the US Patent and Trademark Office Re. U.S. Appl. No. 12/583,746.
Restriction Official Action Dated Mar. 18, 2005 From the US Patent and Trademark Office Re. U.S. Appl. No. 10/363,209.
Restriction Official Action Dated Dec. 28, 2011 From the US Patent and Trademark Office Re. U.S. Appl. No. 12/520,803.
Restriction Official Action Dated Mar. 28, 2012 From the US Patent and Trademark Office Re. U.S. Appl. No. 12/520,811.
Supplementary European Search Report Dated Nov. 19, 2004 From the European Patent Office Re. Application No. 01963414.6.
AACR "97th Annual Meeting 2006: Publications", AACR, American Association of Cancer Research, Retreived From the Internet, 2006.
Arakaki et al. "T134, A Small-Molecule CXCR4 Inhibitor, Has No Cross-Drug Resistance With AMD3100, a CXCR4 Antagonist With a Different Structure", Journal of Virology, XP002199036, 73(2): 1719-1723, Feb. 1999.
Avniel et al. "Involvement of the CXCL12/CXCR4 Pathway in the Recovery of Skin Following Burns", Journal of Investigative Dermatology, 126(2): 468-476, 2006.
Balkwill "The Significance of Cancer Cell Expression of the Chemokine Receptor CXCR4", Seminars in Cancer Biology, 14: 171-179, 2004.
Bork "Powers and Pitfalls in Sequence Analysis: The 70% Hurdle", Genome Research, 10: 398-400, 2000.
Brenner "Errors in Genome Annotation", Trends in Genetics, TIG, 15(4): 132-133, Apr. 1999.
Broxmeyer et al. "Rapid Mobilization of Murine and Human Hematopoietic Stem and Progenitor Cells With AMD3100, a CXCR4 Antagonist", The Journal of Experimental Medicine, 201(8): 1307-1318, Apr. 18, 2005.
Burger et al. "Small Peptide Inhibitors of the CXCR4 Chemokine Receptor (CD184) Antagonize the Activation, Migration, and Antiapoptotic Responses of CXCL12 in Chronic Lymphocytic Leukemia B Cells", Blood, 106(5): 1824-1830, Sep. 1, 2005.
Dar et al. "Chemokine Receptor CXCR4-Dependent Internalization and Resecretion of Functional Chemokine SDF-1 by Bonc Marrow Endothelial and Stromal Cells", Nature Immunology, 6(10): 1038-1046, Oct. 2005.
Darash-Yahana et al. "Role of High Expression Levels of CXCR4 in Tumor Growth, Vascularization, and Metastatis", The FASEB Journal, 18: 1240-1242, 2004. p. 1242, Last Para.

Di Cesare et al. "In Vitro Characterization and Inhibition of the CXCR4/CXCL12 Chemokine Axis in Human Uveal Melanoma Cell Lines", Cancer Cell International, XP021036445, 7(17): 1-8, Nov. 14, 2007. Abstract, Last Para, Title, p. 5, Right col., Last Para.
Doerks et al. "Protein Annotation: Detective Work for Function Predicition", Trends in Genetics, 14(6): 248-250, Jun. 1998.
Esler et al. "Renal Sympathetic Denervation in Patients With Treatment-Resistant Hypertension (The Symplicity HTN-2 Trial): A Randomised Controlled Trial", The Lancet, 376: 1903-1909, Published Online Nov. 17, 2010.
Flomenberg et al. "The Use of AMD3100 Plus G-CSF for Autologous Hematopoietic Progenitor Cell Mobilization Is Superior to G-CSF Alone", Blood, 106(5): 1867-1874, 2005.
Fransen et al. "Suppression of Dualtropic Human Immunodeficiency Virus Type 1 by the CXCR4 Antagonist AMD3100 Is Associated With Efficiency of CXCR4 Use and Baseline Virus Composition", Antimicrobial Agents and Chemotherapy, 52(7): 2608-2615, Apr. 28, 2008.
Ghobrial et al. "Molecular Mechanisms Involved in Homing and Migration of Plasma Cells in Response to CXCR4", Blood, XP002629051, 104(11): 1-33, Apr. 12, 2005.
Gotoh et al. "Increase of R5 HIV-1 Infection and CCR5 Expression in T Cells Treated With High Concentrations of CXCR4 Antagonists and SDF-1", Journal of Infection and Chemotherapy, 7(1): 28-36, 2001.
Hendrix et al. "Safety, Pharmacokinetics, and Antiviral Activity of AMD3100, a Selective CXCR4 Receptor Inhibitor, in HIV-1 Infection", Journal of Aquired Immune Deficiency Syndromes, JAIDS, 37(2): 1253-1261, Oct. 1, 2004.
Heredia et al. "Rapamycin Causes Down-Regulation of CCR5 and Accumulation of Anti-HIV Beta-Chemokines: An Approach to Suppress R5 Strains of HIV-1", Proc. Natl. Acad. Sci. USA, PNAS, 100(18): 10411-10416, Sep. 2, 2003.
Hesselgesser et al. "Neuronal Apoptosis Induced by HIV-1 Gp120 and the Chemokine SDF-1Alpha Is Mediated by the Chemokine Receptor CXCR4", Current Biology, 8: 595-598, Apr. 27, 1998.
Kim et al. "In Vitro Behavior of Hematopoietic Progenitor Cells Under the Influence of Chemoattractants: Stromal Cell-DErived Factor-1, Steel Factor, and the Bone Marrow Environment", Blood, 91(1): 100-110, 1998.
Kollet et al. "Human CD34+CXCR4- Sorted Cells Harbor Intracellular CXCR4, Which Can Be Functionally Expressed and Provide NOD/SCID Repopulation", Blood, 100(8): 2778-2786, 2002.
Lack et al. "A Pharmacokinetic-Pharmacodynamic Model for the Mobilization of CD34+Hematopoictic Progenitor Cells by AMD3100", Clinical Pharmacology and Therapeutics, 77(5): 427-436, 2005.
Lapidot et al. "How Do Stem Cells Find Their Way Home?", Blood, 106(6): 1901-1910, 2005.
Lapidot et al. "The Essential Roles of the Chemokine SDF-1 and Its Receptor CXCR4 in Human Stem Cell Homing and Repopulation of Transplanted Immune-Deficient NOD/SCID and NOD/SCID/B2m<Null> Mice", Leukemia, 16(10): 1992-2003, 2002.
Levesque et al. "Disruption of the CXCR4/CXCL12 Chemotactic Interaction During Hematopoietic Stem Cell Mobilization Induced by GCSF or Cyclophosphamide", Journal of Clinical investigation, 111(2): 187-196, Jan. 2003.
Martin et al. "Chemokines Acting Via CXCR2 and CXCR4 Control the Release of Neutrophils From the Bone Marrow and Their Return Following Senescence", Immunity, 19(4): 583-593, Oct. 2003.
Menu et al. "The Involvement of Stromal Derived Factor 1Alpha in Homing and Progression of Multiple Myeloma in the 5TMM Model", Haematologica/The Hematology Journal, 91(5): 605-612, 2006.
Mueller et al. "Involvement of Chemokine Receptors in Breast Cancer Metastasis", Nature, 410: 50-56, Mar. 2001.
Nagasawa et al. "Molecular Cloning and Structure of a Pre-B-Cell Growth-Stimulating Factor", Proc. Natl. Acad. sci. USA, 91: 2305-2309, Mar. 1994.
Nakashima et al. "Anti-Human Immunodeficiency Virus Activity of a Novel Synthetic Peptide, T22 ([Tyr-5,12, Lys-7]Polyphemusin II): A Possible Inhibitor of Virus-Cell Fusion", Antimicrobial Agents and Chemotherapy, 36(6): 1249-1255, Jun. 1992.

Ngo et al. "Computational Complexity, Protein Structure Prediction, and the Levinthal Paradox", The Protein Folding Problem and Tertiary Structure Prediction, Chap.14: 433-440, 492-495, 1994.

Omagari et al. "Development of Specific CXCR4 Inhibitors Based on An Anti-HIV Peptide, T140, and Their Structure-Activity Relationships Study", Peptide Science, 2000(37): 129-132, 2001.

Peled et al. "Dependence of Human Stem Cell Engraftment and Repopulation of NOD/SCID Mice on CXCR4", Science, 283(5403): 845-848, 1999.

Phillips et al. "Epidermal Growth Factor and Hypoxia-Induced Expression of CXC Chemokine Receptor 4 on Non-Small Cell Lung Cancer Cells Is Regulated by the Phosphatidylinositol 3-Kinase/PTEN/AKT/Mammalian Target of Rapamycin Signaling Pathway and Activation of Hypoxia Inducible Factor-1Alpha", The Journal of Biological Chemistry, 280(23): 22473-22481, 2005.

Phillips et al. "The Stromal Derived Factor-1/CXCL12-CXC Chemokine Receptor 4 Biological Axis in Non-Small Cell Lung Cancer Metastasis", 167: 1676-1686, 2003.

Princen et al. "HIV Chemokine Receptor Inhibitors as Novel Anti-HIV Drugs", Cytokine & Growth Factor Reviews, 16(6): 659-677, 2005.

Ratajczak et al. "T140 Enhances G-CSF-Induced Mobilization of Hematopoietic Stem Cells", Experimental Hematology, 31: 154, Abstract #280, 2003.

Rossi et al. "The Biology of Chemokines and Their Receptors", Annual Reviews of Immunology, 18: 217-242, 2000.

Skolnick et al. "From Genes to Protein Structure and Function: Novel Applications of Computational Approaches in the Genomic Era", Trends in Biotechnology, TIBTECH, 18(1): 34-39, Jan. 2000.

Tamamura et al. "A Future Perspective on the Development of Chemokine Receptor CXCR4 Antagonists", Database EMBASE [Online], XP002675634, Database Accession No. EMB-2008509452, Oct. 2008. & Expert Opinion on Drug Discovery, 3(10): 1155-1166, Oct. 2008.

Tamamura et al. "A Low-Molecular-Weight Inhibitor Against the Chemokine Receptor CXCR4: A Strong Anti-HIV Peptide T140", Biochemical and Biophysical Research Communications, 253(3): 877-882, 1998.

Tamamura et al. "A Low-Molecular-Weight Inhibitor Against the Chemokine Receptor CXCR4: A Strong Anti-HIV Peptide T140", Biochemical and Biophysical Research Communications, 253(3): 877-882, 1998.

Tamamura et al. "Downsizing of an HIV-Cell Fusion Inhibitor, T22 ([Tyr5,12, Lys7]-Polyphemusin II), With the Maintenance of Anti-HIV Activity and Solution Structure", Bioorganic & Medicinal Chemistry, 6: 473-479, 1998.

Tamamura et al. "Effective Lowly Cytotoxic Analogs of an HIV-Cell Fusion Inhibitor, T22 ([Tyr5,12, Lys7]-Polyphemusin II)", Bioorganic & Medicinal Chemistry, 6(2): 231-238, 1998.

Tamamura et al. "Enhancement of the T140-Based Pharmacophores Leads to the Development of More Potent and Bio-Stable CXCR4 Antagonists", Organic Biomolecular Chemistry, 1: 3663-3669, 2003.

Tamamura et al. "HIV-Cell Fusion Inhibitors Targeted to the HIV Second Receptor: T22 and Its Downsized Analogs With High Activity", Peptide Science, 1998(35): 49-52, 1999.

Tamamura et al. "Pharmacophore Identification of A Specific CXCR4 Inhibitor, T140, Leads to Development of Effective Anti-HIV Agents With Very High Selectivity Indexes", Bioorganic & Medicinal Chemistry Letters, 10(23): 2633-2637, 2000.

Tamamura et al. "T140 Analogs as CXCR4 Antagonists Identified as Anti-Metastatic Agents in the Treatment of Breast Cancer", FEBS Letters, 550: 79-83, 2003.

Tamamura et al. "The Therapeutic Potential of CXCR4 Antagonists in the Treatment of HIV Infection, Cancer Metastasis and Rheumatoid Arthritis", Expert Opinion of Therapeutic Targets, 9(6): 1267-1282, 2005.

Tsutsumi et al. "Therapeutic Potential of the Chemokine Receptor CXCR4 Antagonists as Multifunctional Agents", Biopolymers (Peptide Science), XP002629052, 88(2): 279-289, 2006.

Ulvatne et al. "Short Antibacterial Peptides and Erythromycin Act Synergically Against Eschcrichia Coli", Journal of Antimicrobial Chemotherapy, 48: 203-208, 2001.

Weekes et al. "Stromal Derived Factor1Alpha Mediates Resistance to mTOR Inhibition by the Preservation of Hypoxia Inducible Factor-1Alpha (HIF-1Alpha) Expression", Proceedings of the Annual Meeting of the American Association for Cancer Research, AACR, 47: 553, Abstract #2341, 2006.

Wells "Additivity of Mutational Effects in Proteins", Biochemistry, 29(37): 8509-8517, Sep. 18, 1990.

Zannettino et al. "Elevated Serum Levels of Stromal-Derived Factor-1Alpha Are Associated With Increased Osteoclast Activity and Osteolytic Bone Disease in Multiple Myeloma Patients", Cancer Research, 65(5): 1700-1709, Mar. 1, 2005. Abstract, p. 1707, Last Para—p. 1708, First Para.

Zhou et al. "CXCR4 Is A Major Chemokine Receptor on Glioma Cells and Mediates Their Survival", The Journal of Biological Chemistry, 277(51): 49481-49487, Dec. 29, 2002.

Zuluaga et al. "Neutropenia Induced in Outbred Mice by A Simplified Low-Dose Cyclophosphamide Regimen: Characterization and Applicability to Diverse Experimental Models of Infectious Diseases", BMC Infectious Diseases, 6(55): 1-10, Mar. 17, 2006.

Official Action Dated Sep. 12, 2012 From the US Patent and Trademark Office Re. U.S. Appl. No. 12/520,803.

Official Action Dated Sep. 5, 2012 From the US Patent and Trademark Office Re. U.S Appl. No. 12/520,699.

Official Action Dated Sep. 10, 2012 From the US Patent and Trademark Office Re. U.S. Appl. No. 12/583,746.

* cited by examiner

SEQUENCE LISTING

```
<160> NUMBER OF SEQ ID NOS: 68

<210> SEQ ID NO 1
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(14)
<223> OTHER INFORMATION: L-amino acid or D-amino acid
```

```
<220> FEATURE:
<221> NAME/KEY: MISC_FEATURE
<222> LOCATION: (1)..(1)
<223> OTHER INFORMATION: Xaa is Arg, Lys, Orn, citrulline, Ala or Glu
<220> FEATURE:
<221> NAME/KEY: MISC_FEATURE
<222> LOCATION: (2)..(2)
<223> OTHER INFORMATION: Xaa is Arg or Glu
<220> FEATURE:
<221> NAME/KEY: MISC_FEATURE
<222> LOCATION: (3)..(3)
<223> OTHER INFORMATION: Xaa is an aromatic amino acid residue
<220> FEATURE:
<221> NAME/KEY: MISC_FEATURE
<222> LOCATION: (6)..(6)
<223> OTHER INFORMATION: Xaa is Arg, Lys, Orn, citrulline, Ala or Glu
<220> FEATURE:
<221> NAME/KEY: MISC_FEATURE
<222> LOCATION: (7)..(7)
<223> OTHER INFORMATION: Xaa is Arg, Lys, Orn, citrulline, Ala or Glu
<220> FEATURE:
<221> NAME/KEY: MISC_FEATURE
<222> LOCATION: (8)..(8)
<223> OTHER INFORMATION: Xaa is Pro, Gly, Orn, Lys, Ala, citrulline, Arg
      or Glu
<220> FEATURE:
<221> NAME/KEY: MISC_FEATURE
<222> LOCATION: (9)..(9)
<223> OTHER INFORMATION: Xaa is Pro, Gly, Orn, Lys, Ala, citrulline or
      Arg
<220> FEATURE:
<221> NAME/KEY: MISC_FEATURE
<222> LOCATION: (10)..(10)
<223> OTHER INFORMATION: Xaa is Tyr, Phe, Ala, naphthyl Ala, citrulline
      or Glu
<220> FEATURE:
<221> NAME/KEY: MISC_FEATURE
<222> LOCATION: (11)..(11)
<223> OTHER INFORMATION: Xaa is Arg, Lys, Orn, citrulline, Ala or Glu
<220> FEATURE:
<221> NAME/KEY: MISC_FEATURE
<222> LOCATION: (12)..(12)
<223> OTHER INFORMATION: Xaa is Arg, Lys, or citrulline
<220> FEATURE:
<221> NAME/KEY: MISC_FEATURE
<222> LOCATION: (14)..(14)
<223> OTHER INFORMATION: Xaa is Arg, Glu, Lys or citrulline

<400> SEQUENCE: 1

Xaa Xaa Xaa Cys Tyr Xaa Xaa Xaa Xaa Xaa Xaa Xaa Cys Xaa
1               5                   10

<210> SEQ ID NO 2
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(14)
<223> OTHER INFORMATION: L-amino acid or D-amino acid
<220> FEATURE:
<221> NAME/KEY: MISC_FEATURE
<222> LOCATION: (2)..(2)
<223> OTHER INFORMATION: Xaa is Arg or Glu
<220> FEATURE:
<221> NAME/KEY: MISC_FEATURE
<222> LOCATION: (3)..(3)
<223> OTHER INFORMATION: Xaa is an aromatic amino acid residue
<220> FEATURE:
<221> NAME/KEY: MISC_FEATURE
<222> LOCATION: (6)..(6)
<223> OTHER INFORMATION: Xaa is Arg, Lys, Orn, citrulline, Ala or Glu
<220> FEATURE:
<221> NAME/KEY: MISC_FEATURE
<222> LOCATION: (7)..(7)
<223> OTHER INFORMATION: Xaa is Arg, Lys, Orn, citrulline, Ala or Glu
```

```
<220> FEATURE:
<221> NAME/KEY: MISC_FEATURE
<222> LOCATION: (8)..(8)
<223> OTHER INFORMATION: Xaa is Pro, Gly, Orn, Lys, Ala, citrulline, Arg
      or Glu
<220> FEATURE:
<221> NAME/KEY: MISC_FEATURE
<222> LOCATION: (9)..(9)
<223> OTHER INFORMATION: Xaa is Pro, Gly, Orn, Lys, Ala, citrulline or
      Arg
<220> FEATURE:
<221> NAME/KEY: MISC_FEATURE
<222> LOCATION: (10)..(10)
<223> OTHER INFORMATION: Xaa is Tyr, Phe, Ala, naphthyl Ala, citrulline
      or Glu
<220> FEATURE:
<221> NAME/KEY: MISC_FEATURE
<222> LOCATION: (11)..(11)
<223> OTHER INFORMATION: Xaa is Arg, Lys, Orn, citrulline, Ala or Glu
<220> FEATURE:
<221> NAME/KEY: MISC_FEATURE
<222> LOCATION: (12)..(12)
<223> OTHER INFORMATION: Xaa is citrulline, Glu, Arg or Lys
<220> FEATURE:
<221> NAME/KEY: MISC_FEATURE
<222> LOCATION: (14)..(14)
<223> OTHER INFORMATION: Xaa is Arg, Glu, Lys or citrulline

<400> SEQUENCE: 2

Glu Xaa Xaa Cys Tyr Xaa Xaa Xaa Xaa Xaa Xaa Xaa Cys Xaa
1               5                   10

<210> SEQ ID NO 3
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(14)
<223> OTHER INFORMATION: L-amino acid or D-amino acid
<220> FEATURE:
<221> NAME/KEY: MISC_FEATURE
<222> LOCATION: (1)..(1)
<223> OTHER INFORMATION: Xaa is Arg, Lys, Orn, citrulline, Ala or Glu
<220> FEATURE:
<221> NAME/KEY: MISC_FEATURE
<222> LOCATION: (3)..(3)
<223> OTHER INFORMATION: Xaa is an aromatic amino acid residue
<220> FEATURE:
<221> NAME/KEY: MISC_FEATURE
<222> LOCATION: (6)..(6)
<223> OTHER INFORMATION: Xaa is Arg, Lys, Orn, citrulline, Ala or Glu
<220> FEATURE:
<221> NAME/KEY: MISC_FEATURE
<222> LOCATION: (7)..(7)
<223> OTHER INFORMATION: Xaa is Arg, Lys, Orn, citrulline, Ala or Glu
<220> FEATURE:
<221> NAME/KEY: MISC_FEATURE
<222> LOCATION: (8)..(8)
<223> OTHER INFORMATION: Xaa is Pro, Gly, Orn, Lys, Ala, citrulline, Arg
      or Glu
<220> FEATURE:
<221> NAME/KEY: MISC_FEATURE
<222> LOCATION: (9)..(9)
<223> OTHER INFORMATION: Xaa is Pro, Gly, Orn, Lys, Ala, citrulline or
      Arg
<220> FEATURE:
<221> NAME/KEY: MISC_FEATURE
<222> LOCATION: (10)..(10)
<223> OTHER INFORMATION: Xaa is Tyr, Phe, Ala, naphthyl Ala, citrulline
      or Glu
<220> FEATURE:
<221> NAME/KEY: MISC_FEATURE
<222> LOCATION: (11)..(11)
<223> OTHER INFORMATION: Xaa is Arg, Lys, Orn, citrulline, Ala or Glu
<220> FEATURE:
```

```
<221> NAME/KEY: MISC_FEATURE
<222> LOCATION: (12)..(12)
<223> OTHER INFORMATION: Xaa is citrulline, Glu, Arg or Lys
<220> FEATURE:
<221> NAME/KEY: MISC_FEATURE
<222> LOCATION: (14)..(14)
<223> OTHER INFORMATION: Xaa is Arg, Glu, Lys or citrulline

<400> SEQUENCE: 3

Xaa Glu Xaa Cys Tyr Xaa Xaa Xaa Xaa Xaa Xaa Xaa Cys Xaa
1               5                   10

<210> SEQ ID NO 4
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(14)
<223> OTHER INFORMATION: L-amino acid or D-amino acid
<220> FEATURE:
<221> NAME/KEY: MISC_FEATURE
<222> LOCATION: (1)..(1)
<223> OTHER INFORMATION: Xaa is Arg, Lys, Orn, citrulline, Ala or Glu
<220> FEATURE:
<221> NAME/KEY: MISC_FEATURE
<222> LOCATION: (2)..(2)
<223> OTHER INFORMATION: Xaa is Arg or Glu
<220> FEATURE:
<221> NAME/KEY: MISC_FEATURE
<222> LOCATION: (3)..(3)
<223> OTHER INFORMATION: Xaa is an aromatic amino acid residue
<220> FEATURE:
<221> NAME/KEY: MISC_FEATURE
<222> LOCATION: (7)..(7)
<223> OTHER INFORMATION: Xaa is Arg, Lys, Orn, citrulline, Ala or Glu
<220> FEATURE:
<221> NAME/KEY: MISC_FEATURE
<222> LOCATION: (8)..(8)
<223> OTHER INFORMATION: Xaa is Pro, Gly, Orn, Lys, Ala, citrulline, Arg
      or Glu
<220> FEATURE:
<221> NAME/KEY: MISC_FEATURE
<222> LOCATION: (9)..(9)
<223> OTHER INFORMATION: Xaa is Pro, Gly, Orn, Lys, Ala, citrulline or
      Arg
<220> FEATURE:
<221> NAME/KEY: MISC_FEATURE
<222> LOCATION: (10)..(10)
<223> OTHER INFORMATION: Xaa is Tyr, Phe, Ala, naphthyl Ala, citrulline
      or Glu
<220> FEATURE:
<221> NAME/KEY: MISC_FEATURE
<222> LOCATION: (11)..(11)
<223> OTHER INFORMATION: Xaa is Arg, Lys, Orn, citrulline, Ala or Glu
<220> FEATURE:
<221> NAME/KEY: MISC_FEATURE
<222> LOCATION: (12)..(12)
<223> OTHER INFORMATION: Xaa is citrulline, Glu, Arg or Lys
<220> FEATURE:
<221> NAME/KEY: MISC_FEATURE
<222> LOCATION: (14)..(14)
<223> OTHER INFORMATION: Xaa is Arg, Glu, Lys or citrulline

<400> SEQUENCE: 4

Xaa Xaa Xaa Cys Tyr Glu Xaa Xaa Xaa Xaa Xaa Xaa Cys Xaa
1               5                   10

<210> SEQ ID NO 5
<211> LENGTH: 14
<212> TYPE: PRT
<213> ORGANISM: Artificial Sequence
<220> FEATURE:
<223> OTHER INFORMATION: Synthetic
```

```
<220> FEATURE:
<221> NAME/KEY: MISC_FEATURE
<222> LOCATION: (1)..(14)
<223> OTHER INFORMATION: L-amino acid or D-amino acid
<220> FEATURE:
<221> NAME/KEY: MISC_FEATURE
<222> LOCATION: (1)..(1)
<223> OTHER INFORMATION: Xaa is Arg, Lys, Orn, citrulline, Ala or Glu
<220> FEATURE:
<221> NAME/KEY: MISC_FEATURE
<222> LOCATION: (2)..(2)
<223> OTHER INFORMATION: Xaa is Arg or Glu
<220> FEATURE:
<221> NAME/KEY: MISC_FEATURE
<222> LOCATION: (3)..(3)
<223> OTHER INFORMATION: Xaa is an aromatic amino acid residue
<220> FEATURE:
<221> NAME/KEY: MISC_FEATURE
<222> LOCATION: (6)..(6)
<223> OTHER INFORMATION: Xaa is Arg, Lys, Orn, citrulline, Ala or Glu
<220> FEATURE:
<221> NAME/KEY: MISC_FEATURE
<222> LOCATION: (7)..(7)
<223> OTHER INFORMATION: Xaa is Arg or Glu
<220> FEATURE:
<221> NAME/KEY: MISC_FEATURE
<222> LOCATION: (8)..(8)
<223> OTHER INFORMATION: Xaa is Pro, Gly, Orn, Lys, Ala, citrulline, Arg
      or Glu
<220> FEATURE:
<221> NAME/KEY: MISC_FEATURE
<222> LOCATION: (9)..(9)
<223> OTHER INFORMATION: Xaa is Pro, Gly, Orn, Lys, Ala, citrulline or
      Arg
<220> FEATURE:
<221> NAME/KEY: MISC_FEATURE
<222> LOCATION: (10)..(10)
<223> OTHER INFORMATION: Xaa is Tyr, Phe, Ala, naphthyl Ala, citrulline
      or Glu
<220> FEATURE:
<221> NAME/KEY: MISC_FEATURE
<222> LOCATION: (11)..(11)
<223> OTHER INFORMATION: Xaa is Arg, Lys, Orn, citrulline, Ala or Glu
<220> FEATURE:
<221> NAME/KEY: MISC_FEATURE
<222> LOCATION: (12)..(12)
<223> OTHER INFORMATION: Xaa is citrulline, Glu, Arg or Lys
<220> FEATURE:
<221> NAME/KEY: MISC_FEATURE
<222> LOCATION: (14)..(14)
<223> OTHER INFORMATION: Xaa is Arg, Glu, Lys or citrulline

<400> SEQUENCE: 5

Xaa Xaa Xaa Cys Tyr Xaa Xaa Xaa Xaa Xaa Xaa Xaa Cys Xaa
1               5                   10

<210> SEQ ID NO 6
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(14)
<223> OTHER INFORMATION: L-amino acid or D-amino acid
<220> FEATURE:
<221> NAME/KEY: MISC_FEATURE
<222> LOCATION: (1)..(1)
<223> OTHER INFORMATION: Xaa is Arg, Lys, Orn, citrulline, Ala or Glu
<220> FEATURE:
<221> NAME/KEY: MISC_FEATURE
<222> LOCATION: (2)..(2)
<223> OTHER INFORMATION: Xaa is Arg or Glu
<220> FEATURE:
<221> NAME/KEY: MISC_FEATURE
<222> LOCATION: (3)..(3)
<223> OTHER INFORMATION: Xaa is an aromatic amino acid residue
```

```
<220> FEATURE:
<221> NAME/KEY: MISC_FEATURE
<222> LOCATION: (6)..(6)
<223> OTHER INFORMATION: Xaa is Arg, Lys, Orn, citrulline, Ala or Glu
<220> FEATURE:
<221> NAME/KEY: MISC_FEATURE
<222> LOCATION: (7)..(7)
<223> OTHER INFORMATION: Xaa is Arg, Lys, Orn, citrulline, Ala or Glu
<220> FEATURE:
<221> NAME/KEY: MISC_FEATURE
<222> LOCATION: (9)..(9)
<223> OTHER INFORMATION: Xaa is Pro, Gly, Orn, Lys, Ala, citrulline or
      Arg
<220> FEATURE:
<221> NAME/KEY: MISC_FEATURE
<222> LOCATION: (10)..(10)
<223> OTHER INFORMATION: Xaa is Tyr, Phe, Ala, naphthyl Ala, citrulline
      or Glu
<220> FEATURE:
<221> NAME/KEY: MISC_FEATURE
<222> LOCATION: (11)..(11)
<223> OTHER INFORMATION: Xaa is Arg, Lys, Orn, citrulline, Ala or Glu
<220> FEATURE:
<221> NAME/KEY: MISC_FEATURE
<222> LOCATION: (12)..(12)
<223> OTHER INFORMATION: Xaa is citrulline, Glu, Arg or Lys
<220> FEATURE:
<221> NAME/KEY: MISC_FEATURE
<222> LOCATION: (14)..(14)
<223> OTHER INFORMATION: Xaa is Arg, Glu, Lys or citrulline

<400> SEQUENCE: 6

Xaa Xaa Xaa Cys Tyr Xaa Xaa Glu Xaa Xaa Xaa Xaa Cys Xaa
1               5                   10

<210> SEQ ID NO 7
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(14)
<223> OTHER INFORMATION: L-amino acid or D-amino acid
<220> FEATURE:
<221> NAME/KEY: MISC_FEATURE
<222> LOCATION: (1)..(1)
<223> OTHER INFORMATION: Xaa is Arg, Lys, Orn, citrulline, Ala or Glu
<220> FEATURE:
<221> NAME/KEY: MISC_FEATURE
<222> LOCATION: (2)..(2)
<223> OTHER INFORMATION: Xaa is Arg or Glu
<220> FEATURE:
<221> NAME/KEY: MISC_FEATURE
<222> LOCATION: (3)..(3)
<223> OTHER INFORMATION: Xaa is an aromatic amino acid residue
<220> FEATURE:
<221> NAME/KEY: MISC_FEATURE
<222> LOCATION: (6)..(6)
<223> OTHER INFORMATION: Xaa is Arg, Lys, Orn, citrulline, Ala or Glu
<220> FEATURE:
<221> NAME/KEY: MISC_FEATURE
<222> LOCATION: (7)..(7)
<223> OTHER INFORMATION: Xaa is Arg, Lys, Orn, citrulline, Ala or Glu
<220> FEATURE:
<221> NAME/KEY: MISC_FEATURE
<222> LOCATION: (8)..(8)
<223> OTHER INFORMATION: Xaa is Pro, Gly, Orn, Lys, Ala, citrulline, Arg
      or Glu
<220> FEATURE:
<221> NAME/KEY: MISC_FEATURE
<222> LOCATION: (9)..(9)
<223> OTHER INFORMATION: Xaa is Pro, Gly, Orn, Lys, Ala, citrulline or
      Arg
<220> FEATURE:
<221> NAME/KEY: MISC_FEATURE
<222> LOCATION: (10)..(10)
```

```
<223> OTHER INFORMATION: Xaa is  Glu
<220> FEATURE:
<221> NAME/KEY: MISC_FEATURE
<222> LOCATION: (11)..(11)
<223> OTHER INFORMATION: Xaa is Arg, Lys, Orn, citrulline, Ala or Glu
<220> FEATURE:
<221> NAME/KEY: MISC_FEATURE
<222> LOCATION: (12)..(12)
<223> OTHER INFORMATION: Xaa is citrulline, Glu, Arg or Lys
<220> FEATURE:
<221> NAME/KEY: MISC_FEATURE
<222> LOCATION: (14)..(14)
<223> OTHER INFORMATION: Xaa is Arg, Glu, Lys or citrulline

<400> SEQUENCE: 7

Xaa Xaa Xaa Cys Tyr Xaa Xaa Xaa Xaa Xaa Xaa Xaa Cys Xaa
1               5                  10

<210> SEQ ID NO 8
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(14)
<223> OTHER INFORMATION: L-amino acid or D-amino acid
<220> FEATURE:
<221> NAME/KEY: MISC_FEATURE
<222> LOCATION: (1)..(1)
<223> OTHER INFORMATION: Xaa is Arg, Lys, Orn, citrulline, Ala or Glu
<220> FEATURE:
<221> NAME/KEY: MISC_FEATURE
<222> LOCATION: (2)..(2)
<223> OTHER INFORMATION: Xaa is Arg or Glu
<220> FEATURE:
<221> NAME/KEY: MISC_FEATURE
<222> LOCATION: (3)..(3)
<223> OTHER INFORMATION: Xaa is an aromatic amino acid residue
<220> FEATURE:
<221> NAME/KEY: MISC_FEATURE
<222> LOCATION: (6)..(6)
<223> OTHER INFORMATION: Xaa is Arg, Lys, Orn, citrulline, Ala or Glu
<220> FEATURE:
<221> NAME/KEY: MISC_FEATURE
<222> LOCATION: (7)..(7)
<223> OTHER INFORMATION: Xaa is Arg, Lys, Orn, citrulline, Ala or Glu
<220> FEATURE:
<221> NAME/KEY: MISC_FEATURE
<222> LOCATION: (8)..(8)
<223> OTHER INFORMATION: Xaa is Pro, Gly, Orn, Lys, Ala, citrulline, Arg
      or Glu
<220> FEATURE:
<221> NAME/KEY: MISC_FEATURE
<222> LOCATION: (9)..(9)
<223> OTHER INFORMATION: Xaa is Pro, Gly, Orn, Lys, Ala, citrulline or
      Arg
<220> FEATURE:
<221> NAME/KEY: MISC_FEATURE
<222> LOCATION: (10)..(10)
<223> OTHER INFORMATION: Xaa is Tyr, Phe, Ala, naphthyl Ala, citrulline
      or Glu
<220> FEATURE:
<221> NAME/KEY: MISC_FEATURE
<222> LOCATION: (12)..(12)
<223> OTHER INFORMATION: Xaa is citrulline, Glu, Arg or Lys
<220> FEATURE:
<221> NAME/KEY: MISC_FEATURE
<222> LOCATION: (14)..(14)
<223> OTHER INFORMATION: Xaa is Arg, Glu, Lys or citrulline

<400> SEQUENCE: 8

Xaa Xaa Xaa Cys Tyr Xaa Xaa Xaa Xaa Xaa Glu Xaa Cys Xaa
1               5                  10
```

-continued

```
<210> SEQ ID NO 9
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(14)
<223> OTHER INFORMATION: L-amino acid or D-amino acid
<220> FEATURE:
<221> NAME/KEY: MISC_FEATURE
<222> LOCATION: (1)..(1)
<223> OTHER INFORMATION: Xaa is Arg, Lys, Orn, citrulline, Ala or Glu
<220> FEATURE:
<221> NAME/KEY: MISC_FEATURE
<222> LOCATION: (2)..(2)
<223> OTHER INFORMATION: Xaa is Arg or Glu
<220> FEATURE:
<221> NAME/KEY: MISC_FEATURE
<222> LOCATION: (3)..(3)
<223> OTHER INFORMATION: Xaa is an aromatic amino acid residue
<220> FEATURE:
<221> NAME/KEY: MISC_FEATURE
<222> LOCATION: (6)..(6)
<223> OTHER INFORMATION: Xaa is Arg, Lys, Orn, citrulline, Ala or Glu
<220> FEATURE:
<221> NAME/KEY: MISC_FEATURE
<222> LOCATION: (7)..(7)
<223> OTHER INFORMATION: Xaa is Arg, Lys, Orn, citrulline, Ala or Glu
<220> FEATURE:
<221> NAME/KEY: MISC_FEATURE
<222> LOCATION: (8)..(8)
<223> OTHER INFORMATION: Xaa is Pro, Gly, Orn, Lys, Ala, citrulline, Arg
      or Glu
<220> FEATURE:
<221> NAME/KEY: MISC_FEATURE
<222> LOCATION: (9)..(9)
<223> OTHER INFORMATION: Xaa is Pro, Gly, Orn, Lys, Ala, citrulline or
      Arg
<220> FEATURE:
<221> NAME/KEY: MISC_FEATURE
<222> LOCATION: (10)..(10)
<223> OTHER INFORMATION: Xaa is Tyr, Phe, Ala, naphthyl Ala, citrulline
      or Glu
<220> FEATURE:
<221> NAME/KEY: MISC_FEATURE
<222> LOCATION: (11)..(11)
<223> OTHER INFORMATION: Xaa is Arg, Lys, Orn, citrulline, Ala or Glu
<220> FEATURE:
<221> NAME/KEY: MISC_FEATURE
<222> LOCATION: (12)..(12)
<223> OTHER INFORMATION: Xaa is Glu, Arg or Lys
<220> FEATURE:
<221> NAME/KEY: MISC_FEATURE
<222> LOCATION: (14)..(14)
<223> OTHER INFORMATION: Xaa is Arg, Glu, Lys or citrulline

<400> SEQUENCE: 9

Xaa Xaa Xaa Cys Tyr Xaa Xaa Xaa Xaa Xaa Xaa Xaa Cys Xaa
1               5                   10

<210> SEQ ID NO 10
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(14)
<223> OTHER INFORMATION: L-amino acid or D-amino acid
<220> FEATURE:
<221> NAME/KEY: MISC_FEATURE
<222> LOCATION: (1)..(1)
<223> OTHER INFORMATION: Xaa is Arg, Lys, Orn, citrulline, Ala or Glu
<220> FEATURE:
<221> NAME/KEY: MISC_FEATURE
```

```
<222> LOCATION: (2)..(2)
<223> OTHER INFORMATION: Xaa is Arg or Glu
<220> FEATURE:
<221> NAME/KEY: MISC_FEATURE
<222> LOCATION: (3)..(3)
<223> OTHER INFORMATION: Xaa is an aromatic amino acid residue
<220> FEATURE:
<221> NAME/KEY: MISC_FEATURE
<222> LOCATION: (6)..(6)
<223> OTHER INFORMATION: Xaa is Arg, Lys, Orn, citrulline, Ala or Glu
<220> FEATURE:
<221> NAME/KEY: MISC_FEATURE
<222> LOCATION: (7)..(7)
<223> OTHER INFORMATION: Xaa is Arg, Lys, Orn, citrulline, Ala or Glu
<220> FEATURE:
<221> NAME/KEY: MISC_FEATURE
<222> LOCATION: (8)..(8)
<223> OTHER INFORMATION: Xaa is Pro, Gly, Orn, Lys, Ala, citrulline, Arg
      or Glu
<220> FEATURE:
<221> NAME/KEY: MISC_FEATURE
<222> LOCATION: (9)..(9)
<223> OTHER INFORMATION: Xaa is Pro, Gly, Orn, Lys, Ala, citrulline or
      Arg
<220> FEATURE:
<221> NAME/KEY: MISC_FEATURE
<222> LOCATION: (10)..(10)
<223> OTHER INFORMATION: Xaa is Tyr, Phe, Ala, naphthyl Ala, citrulline
      or Glu
<220> FEATURE:
<221> NAME/KEY: MISC_FEATURE
<222> LOCATION: (11)..(11)
<223> OTHER INFORMATION: Xaa is Arg, Lys, Orn, citrulline, Ala or Glu
<220> FEATURE:
<221> NAME/KEY: MISC_FEATURE
<222> LOCATION: (12)..(12)
<223> OTHER INFORMATION: Xaa is citrulline, Glu, Arg or Lys
<220> FEATURE:
<221> NAME/KEY: MISC_FEATURE
<222> LOCATION: (14)..(14)
<223> OTHER INFORMATION: Xaa is Glu, Lys or citrulline

<400> SEQUENCE: 10

Xaa Xaa Xaa Cys Tyr Xaa Xaa Xaa Xaa Xaa Xaa Xaa Cys Xaa
1               5                   10

<210> SEQ ID NO 11
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is Naphthyl-alanine
<220> FEATURE:
<221> NAME/KEY: MISC_FEATURE
<222> LOCATION: (6)..(6)
<223> OTHER INFORMATION: Xaa is citrulline
<220> FEATURE:
<221> NAME/KEY: MISC_FEATURE
<222> LOCATION: (8)..(8)
<223> OTHER INFORMATION: Xaa can be Lys or D-Lys
<220> FEATURE:
<221> NAME/KEY: MISC_FEATURE
<222> LOCATION: (12)..(12)
<223> OTHER INFORMATION: Xaa is citrulline

<400> SEQUENCE: 11

Arg Arg Xaa Cys Tyr Xaa Lys Xaa Pro Tyr Arg Xaa Cys Arg
1               5                   10

<210> SEQ ID NO 12
<211> LENGTH: 14
<212> TYPE: PRT
```

<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is naphthyl-alanine
<220> FEATURE:
<221> NAME/KEY: MISC_FEATURE
<222> LOCATION: (8)..(8)
<223> OTHER INFORMATION: Xaa is D-Citrulline
<220> FEATURE:
<221> NAME/KEY: MISC_FEATURE
<222> LOCATION: (12)..(12)
<223> OTHER INFORMATION: Xaa is citrulline

<400> SEQUENCE: 12

Arg Arg Xaa Cys Tyr Arg Lys Xaa Pro Tyr Arg Xaa Cys Arg
1               5                   10

<210> SEQ ID NO 13
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is naphthyl-alanine
<220> FEATURE:
<221> NAME/KEY: MISC_FEATURE
<222> LOCATION: (6)..(6)
<223> OTHER INFORMATION: Xaa is citrulline
<220> FEATURE:
<221> NAME/KEY: MISC_FEATURE
<222> LOCATION: (8)..(8)
<223> OTHER INFORMATION: Xaa is D-citrulline
<220> FEATURE:
<221> NAME/KEY: MISC_FEATURE
<222> LOCATION: (12)..(12)
<223> OTHER INFORMATION: Xaa is citrulline

<400> SEQUENCE: 13

Arg Arg Xaa Cys Tyr Xaa Lys Xaa Pro Tyr Arg Xaa Cys Arg
1               5                   10

<210> SEQ ID NO 14
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is naphthyl-alanine
<220> FEATURE:
<221> NAME/KEY: MISC_FEATURE
<222> LOCATION: (6)..(6)
<223> OTHER INFORMATION: Xaa is citrulline
<220> FEATURE:
<221> NAME/KEY: MISC_FEATURE
<222> LOCATION: (8)..(8)
<223> OTHER INFORMATION: Xaa can be Lys or D-Lys
<220> FEATURE:
<221> NAME/KEY: MISC_FEATURE
<222> LOCATION: (11)..(11)
<223> OTHER INFORMATION: Xaa is citrulline
<220> FEATURE:
<221> NAME/KEY: MISC_FEATURE
<222> LOCATION: (12)..(12)
<223> OTHER INFORMATION: Xaa is citrulline

<400> SEQUENCE: 14

Arg Arg Xaa Cys Tyr Xaa Lys Xaa Pro Tyr Xaa Xaa Cys Arg
1               5                   10

<210> SEQ ID NO 15
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is citrulline
<220> FEATURE:
<221> NAME/KEY: MISC_FEATURE
<222> LOCATION: (3)..(3)
<223> OTHER INFORMATION: Xaa is naphthyl-alanine
<220> FEATURE:
<221> NAME/KEY: MISC_FEATURE
<222> LOCATION: (6)..(6)
<223> OTHER INFORMATION: Xaa is citrulline
<220> FEATURE:
<221> NAME/KEY: MISC_FEATURE
<222> LOCATION: (8)..(8)
<223> OTHER INFORMATION: Xaa can be Lys or D-Lys
<220> FEATURE:
<221> NAME/KEY: MISC_FEATURE
<222> LOCATION: (12)..(12)
<223> OTHER INFORMATION: Xaa is citrulline

<400> SEQUENCE: 15

Xaa Arg Xaa Cys Tyr Xaa Lys Xaa Pro Tyr Arg Xaa Cys Arg
1               5                   10

<210> SEQ ID NO 16
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is citrulline
<220> FEATURE:
<221> NAME/KEY: MISC_FEATURE
<222> LOCATION: (3)..(3)
<223> OTHER INFORMATION: Xaa is naphthyl-alanine
<220> FEATURE:
<221> NAME/KEY: MISC_FEATURE
<222> LOCATION: (8)..(8)
<223> OTHER INFORMATION: Xaa is D-citrulline
<220> FEATURE:
<221> NAME/KEY: MISC_FEATURE
<222> LOCATION: (12)..(12)
<223> OTHER INFORMATION: Xaa is citrulline

<400> SEQUENCE: 16

Xaa Arg Xaa Cys Tyr Arg Lys Xaa Pro Tyr Arg Xaa Cys Arg
1               5                   10

<210> SEQ ID NO 17
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is naphthyl-alanine
<220> FEATURE:
<221> NAME/KEY: MISC_FEATURE
<222> LOCATION: (8)..(8)
<223> OTHER INFORMATION: Xaa is D-citrulline

```
<220> FEATURE:
<221> NAME/KEY: MISC_FEATURE
<222> LOCATION: (11)..(11)
<223> OTHER INFORMATION: Xaa is citrulline
<220> FEATURE:
<221> NAME/KEY: MISC_FEATURE
<222> LOCATION: (12)..(12)
<223> OTHER INFORMATION: Xaa is citrulline

<400> SEQUENCE: 17

Arg Arg Xaa Cys Tyr Arg Lys Xaa Pro Tyr Xaa Xaa Cys Arg
1               5                   10

<210> SEQ ID NO 18
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is citrulline
<220> FEATURE:
<221> NAME/KEY: MISC_FEATURE
<222> LOCATION: (3)..(3)
<223> OTHER INFORMATION: Xaa is naphthyl-alanine
<220> FEATURE:
<221> NAME/KEY: MISC_FEATURE
<222> LOCATION: (8)..(8)
<223> OTHER INFORMATION: Xaa is D-lysine
<220> FEATURE:
<221> NAME/KEY: MISC_FEATURE
<222> LOCATION: (11)..(11)
<223> OTHER INFORMATION: Xaa is citrulline
<220> FEATURE:
<221> NAME/KEY: MISC_FEATURE
<222> LOCATION: (12)..(12)
<223> OTHER INFORMATION: Xaa is citrulline

<400> SEQUENCE: 18

Xaa Arg Xaa Cys Tyr Arg Lys Xaa Pro Tyr Xaa Xaa Cys Arg
1               5                   10

<210> SEQ ID NO 19
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is naphthyl-alanine
<220> FEATURE:
<221> NAME/KEY: MISC_FEATURE
<222> LOCATION: (6)..(6)
<223> OTHER INFORMATION: Xaa is citrulline
<220> FEATURE:
<221> NAME/KEY: MISC_FEATURE
<222> LOCATION: (8)..(8)
<223> OTHER INFORMATION: Xaa is D-citrulline
<220> FEATURE:
<221> NAME/KEY: MISC_FEATURE
<222> LOCATION: (12)..(12)
<223> OTHER INFORMATION: Xaa is citrulline

<400> SEQUENCE: 19

Arg Arg Xaa Cys Tyr Xaa Lys Xaa Pro Tyr Xaa Cys Arg
1               5                   10

<210> SEQ ID NO 20
<211> LENGTH: 14
<212> TYPE: PRT
```

```
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is naphthyl-alanine
<220> FEATURE:
<221> NAME/KEY: MISC_FEATURE
<222> LOCATION: (6)..(6)
<223> OTHER INFORMATION: Xaa is citrulline
<220> FEATURE:
<221> NAME/KEY: MISC_FEATURE
<222> LOCATION: (8)..(8)
<223> OTHER INFORMATION: Xaa can be Lys or D-Lys
<220> FEATURE:
<221> NAME/KEY: MISC_FEATURE
<222> LOCATION: (11)..(11)
<223> OTHER INFORMATION: Xaa is citrulline
<220> FEATURE:
<221> NAME/KEY: MISC_FEATURE
<222> LOCATION: (12)..(12)
<223> OTHER INFORMATION: Xaa is citrulline

<400> SEQUENCE: 20

Arg Arg Xaa Cys Tyr Xaa Lys Xaa Pro Tyr Xaa Xaa Cys Arg
1               5                   10

<210> SEQ ID NO 21
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is citrulline
<220> FEATURE:
<221> NAME/KEY: MISC_FEATURE
<222> LOCATION: (3)..(3)
<223> OTHER INFORMATION: Xaa is naphthyl-alanine
<220> FEATURE:
<221> NAME/KEY: MISC_FEATURE
<222> LOCATION: (6)..(6)
<223> OTHER INFORMATION: Xaa is citrulline
<220> FEATURE:
<221> NAME/KEY: MISC_FEATURE
<222> LOCATION: (8)..(8)
<223> OTHER INFORMATION: Xaa can be Lys or D-Lys
<220> FEATURE:
<221> NAME/KEY: MISC_FEATURE
<222> LOCATION: (12)..(12)
<223> OTHER INFORMATION: Xaa is citrulline

<400> SEQUENCE: 21

Xaa Arg Xaa Cys Tyr Xaa Lys Xaa Pro Tyr Arg Xaa Cys Arg
1               5                   10

<210> SEQ ID NO 22
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is citrulline
<220> FEATURE:
<221> NAME/KEY: MISC_FEATURE
<222> LOCATION: (3)..(3)
<223> OTHER INFORMATION: Xaa is naphthyl-alanine
<220> FEATURE:
<221> NAME/KEY: MISC_FEATURE
<222> LOCATION: (8)..(8)
```

<223> OTHER INFORMATION: Xaa is D-citrulline
<220> FEATURE:
<221> NAME/KEY: MISC_FEATURE
<222> LOCATION: (12)..(12)
<223> OTHER INFORMATION: Xaa is citrulline

<400> SEQUENCE: 22

Xaa Arg Xaa Cys Tyr Arg Lys Xaa Pro Tyr Arg Xaa Cys Arg
1               5                   10

<210> SEQ ID NO 23
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is naphthyl-alanine
<220> FEATURE:
<221> NAME/KEY: MISC_FEATURE
<222> LOCATION: (8)..(8)
<223> OTHER INFORMATION: Xaa is D-citrulline
<220> FEATURE:
<221> NAME/KEY: MISC_FEATURE
<222> LOCATION: (11)..(11)
<223> OTHER INFORMATION: Xaa is citrulline
<220> FEATURE:
<221> NAME/KEY: MISC_FEATURE
<222> LOCATION: (12)..(12)
<223> OTHER INFORMATION: Xaa is citrulline

<400> SEQUENCE: 23

Arg Arg Xaa Cys Tyr Arg Lys Xaa Pro Tyr Xaa Xaa Cys Arg
1               5                   10

<210> SEQ ID NO 24
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (1)..(1)
<223> OTHER INFORMATION: Xaa is citrulline
<220> FEATURE:
<221> NAME/KEY: MISC_FEATURE
<222> LOCATION: (3)..(3)
<223> OTHER INFORMATION: Xaa is naphthyl-alanine
<220> FEATURE:
<221> NAME/KEY: MISC_FEATURE
<222> LOCATION: (8)..(8)
<223> OTHER INFORMATION: Xaa can be Lys or D-Lys
<220> FEATURE:
<221> NAME/KEY: MISC_FEATURE
<222> LOCATION: (11)..(11)
<223> OTHER INFORMATION: Xaa is citrulline
<220> FEATURE:
<221> NAME/KEY: MISC_FEATURE
<222> LOCATION: (12)..(12)
<223> OTHER INFORMATION: Xaa is citrulline

<400> SEQUENCE: 24

Xaa Arg Xaa Cys Tyr Arg Lys Xaa Pro Tyr Xaa Xaa Cys Arg
1               5                   10

<210> SEQ ID NO 25
<211> LENGTH: 14
<212> TYPE: PRT
<213> ORGANISM: Artificial Sequence
<220> FEATURE:
<223> OTHER INFORMATION: Synthetic

```
<220> FEATURE:
<221> NAME/KEY: MISC_FEATURE
<222> LOCATION: (3)..(3)
<223> OTHER INFORMATION: Xaa is naphthyl-alanine
<220> FEATURE:
<221> NAME/KEY: MISC_FEATURE
<222> LOCATION: (8)..(8)
<223> OTHER INFORMATION: Xaa can be Lys or D-Lys
<220> FEATURE:
<221> NAME/KEY: MISC_FEATURE
<222> LOCATION: (12)..(12)
<223> OTHER INFORMATION: Xaa is citrulline

<400> SEQUENCE: 25

Glu Arg Xaa Cys Tyr Arg Lys Xaa Pro Tyr Arg Xaa Cys Arg
1               5                   10

<210> SEQ ID NO 26
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (8)..(8)
<223> OTHER INFORMATION: Xaa can be Lys or D-Lys
<220> FEATURE:
<221> NAME/KEY: MISC_FEATURE
<222> LOCATION: (3)..(3)
<223> OTHER INFORMATION: Xaa is naphthyl-alanine
<220> FEATURE:
<221> NAME/KEY: MISC_FEATURE
<222> LOCATION: (12)..(12)
<223> OTHER INFORMATION: Xaa is citrulline

<400> SEQUENCE: 26

Arg Glu Xaa Cys Tyr Arg Lys Xaa Pro Tyr Arg Xaa Cys Arg
1               5                   10

<210> SEQ ID NO 27
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is naphthyl-alanine
<220> FEATURE:
<221> NAME/KEY: MISC_FEATURE
<222> LOCATION: (8)..(8)
<223> OTHER INFORMATION: Xaa can be Lys or D-Lys
<220> FEATURE:
<221> NAME/KEY: MISC_FEATURE
<222> LOCATION: (12)..(12)
<223> OTHER INFORMATION: Xaa is citrulline

<400> SEQUENCE: 27

Arg Arg Xaa Cys Tyr Glu Lys Xaa Pro Tyr Arg Xaa Cys Arg
1               5                   10

<210> SEQ ID NO 28
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is naphthyl-alanine
<220> FEATURE:
```

```
<221> NAME/KEY: MISC_FEATURE
<222> LOCATION: (8)..(8)
<223> OTHER INFORMATION: Xaa can be Lys or D-Lys
<220> FEATURE:
<221> NAME/KEY: MISC_FEATURE
<222> LOCATION: (12)..(12)
<223> OTHER INFORMATION: Xaa is citrulline

<400> SEQUENCE: 28

Arg Arg Xaa Cys Tyr Arg Glu Lys Pro Tyr Arg Xaa Cys Arg
1               5                   10

<210> SEQ ID NO 29
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is naphthyl-alanine
<220> FEATURE:
<221> NAME/KEY: MISC_FEATURE
<222> LOCATION: (8)..(8)
<223> OTHER INFORMATION: Xaa can be Glu or D-Glu
<220> FEATURE:
<221> NAME/KEY: MISC_FEATURE
<222> LOCATION: (12)..(12)
<223> OTHER INFORMATION: Xaa is citrulline

<400> SEQUENCE: 29

Arg Arg Xaa Cys Tyr Arg Lys Xaa Pro Tyr Arg Xaa Cys Arg
1               5                   10

<210> SEQ ID NO 30
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is naphthyl-alanine
<220> FEATURE:
<221> NAME/KEY: MISC_FEATURE
<222> LOCATION: (8)..(8)
<223> OTHER INFORMATION: Xaa can be Lys or D-Lys
<220> FEATURE:
<221> NAME/KEY: MISC_FEATURE
<222> LOCATION: (12)..(12)
<223> OTHER INFORMATION: Xaa is citrulline

<400> SEQUENCE: 30

Arg Arg Xaa Cys Tyr Arg Lys Xaa Pro Tyr Glu Xaa Cys Arg
1               5                   10

<210> SEQ ID NO 31
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is naphthyl-alanine
<220> FEATURE:
<221> NAME/KEY: MISC_FEATURE
<222> LOCATION: (8)..(8)
<223> OTHER INFORMATION: Xaa can be Lys or D-Lys
<220> FEATURE:
<221> NAME/KEY: MISC_FEATURE
```

```
<222> LOCATION: (12)..(12)
<223> OTHER INFORMATION: Xaa is citrulline

<400> SEQUENCE: 31

Arg Arg Xaa Cys Tyr Arg Lys Xaa Pro Tyr Arg Xaa Cys Glu
1               5                   10

<210> SEQ ID NO 32
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is naphthyl-alanine
<220> FEATURE:
<221> NAME/KEY: MISC_FEATURE
<222> LOCATION: (6)..(6)
<223> OTHER INFORMATION: Xaa is citrulline
<220> FEATURE:
<221> NAME/KEY: MISC_FEATURE
<222> LOCATION: (8)..(8)
<223> OTHER INFORMATION: Xaa can be Glu or D-Glu
<220> FEATURE:
<221> NAME/KEY: MISC_FEATURE
<222> LOCATION: (12)..(12)
<223> OTHER INFORMATION: Xaa is citrulline

<400> SEQUENCE: 32

Arg Arg Xaa Cys Tyr Xaa Lys Xaa Pro Tyr Arg Xaa Cys Arg
1               5                   10

<210> SEQ ID NO 33
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is naphthyl-alanine
<220> FEATURE:
<221> NAME/KEY: MISC_FEATURE
<222> LOCATION: (6)..(6)
<223> OTHER INFORMATION: Xaa is D-Glu
<220> FEATURE:
<221> NAME/KEY: MISC_FEATURE
<222> LOCATION: (8)..(8)
<223> OTHER INFORMATION: Xaa is D-citrulline
<220> FEATURE:
<221> NAME/KEY: MISC_FEATURE
<222> LOCATION: (12)..(12)
<223> OTHER INFORMATION: Xaa is citrulline

<400> SEQUENCE: 33

Arg Arg Xaa Cys Tyr Xaa Lys Xaa Pro Tyr Arg Xaa Cys Arg
1               5                   10

<210> SEQ ID NO 34
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is naphthyl-alanine
<220> FEATURE:
<221> NAME/KEY: MISC_FEATURE
<222> LOCATION: (6)..(6)
```

-continued

<223> OTHER INFORMATION: Xaa can be Glu or D-Glu
<220> FEATURE:
<221> NAME/KEY: MISC_FEATURE
<222> LOCATION: (8)..(8)
<223> OTHER INFORMATION: Xaa can be Glu or D-Glu
<220> FEATURE:
<221> NAME/KEY: MISC_FEATURE
<222> LOCATION: (12)..(12)
<223> OTHER INFORMATION: Xaa is citrulline

<400> SEQUENCE: 34

Arg Arg Xaa Cys Tyr Xaa Lys Xaa Pro Tyr Arg Xaa Cys Arg
1               5                   10

<210> SEQ ID NO 35
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is naphthyl-alanine
<220> FEATURE:
<221> NAME/KEY: MISC_FEATURE
<222> LOCATION: (6)..(6)
<223> OTHER INFORMATION: Xaa is citrulline
<220> FEATURE:
<221> NAME/KEY: MISC_FEATURE
<222> LOCATION: (8)..(8)
<223> OTHER INFORMATION: Xaa can be Glu or D-Glu
<220> FEATURE:
<221> NAME/KEY: MISC_FEATURE
<222> LOCATION: (12)..(12)
<223> OTHER INFORMATION: Xaa is citrulline

<400> SEQUENCE: 35

Glu Arg Xaa Cys Tyr Xaa Lys Xaa Pro Tyr Arg Xaa Cys Arg
1               5                   10

<210> SEQ ID NO 36
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is naphthyl-alanine
<220> FEATURE:
<221> NAME/KEY: MISC_FEATURE
<222> LOCATION: (6)..(6)
<223> OTHER INFORMATION: Xaa is citrulline
<220> FEATURE:
<221> NAME/KEY: MISC_FEATURE
<222> LOCATION: (8)..(8)
<223> OTHER INFORMATION: Xaa can be Glu or D-Glu
<220> FEATURE:
<221> NAME/KEY: MISC_FEATURE
<222> LOCATION: (10)..(10)
<223> OTHER INFORMATION: Xaa is Glu or D-Glu
<220> FEATURE:
<221> NAME/KEY: MISC_FEATURE
<222> LOCATION: (12)..(12)
<223> OTHER INFORMATION: Xaa is citrulline

<400> SEQUENCE: 36

Arg Arg Xaa Cys Tyr Xaa Lys Xaa Pro Xaa Arg Xaa Cys Arg
1               5                   10

<210> SEQ ID NO 37
<211> LENGTH: 14

```
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is naphthyl-alanine
<220> FEATURE:
<221> NAME/KEY: MISC_FEATURE
<222> LOCATION: (6)..(6)
<223> OTHER INFORMATION: Xaa is citrulline
<220> FEATURE:
<221> NAME/KEY: MISC_FEATURE
<222> LOCATION: (8)..(8)
<223> OTHER INFORMATION: Xaa can be Glu or D-Glu
<220> FEATURE:
<221> NAME/KEY: MISC_FEATURE
<222> LOCATION: (12)..(12)
<223> OTHER INFORMATION: Xaa can be Glu or D-Glu

<400> SEQUENCE: 37

Arg Arg Xaa Cys Tyr Xaa Lys Xaa Pro Tyr Arg Xaa Cys Arg
1               5                   10

<210> SEQ ID NO 38
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is naphthyl-alanine
<220> FEATURE:
<221> NAME/KEY: MISC_FEATURE
<222> LOCATION: (6)..(6)
<223> OTHER INFORMATION: Xaa is citrulline
<220> FEATURE:
<221> NAME/KEY: MISC_FEATURE
<222> LOCATION: (8)..(8)
<223> OTHER INFORMATION: Xaa can be Glu or D-Glu
<220> FEATURE:
<221> NAME/KEY: MISC_FEATURE
<222> LOCATION: (12)..(12)
<223> OTHER INFORMATION: Xaa is citrulline

<400> SEQUENCE: 38

Glu Arg Xaa Cys Tyr Xaa Lys Xaa Pro Tyr Arg Xaa Cys Arg
1               5                   10

<210> SEQ ID NO 39
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is naphthyl-alanine
<220> FEATURE:
<221> NAME/KEY: MISC_FEATURE
<222> LOCATION: (6)..(6)
<223> OTHER INFORMATION: Xaa is citrulline
<220> FEATURE:
<221> NAME/KEY: MISC_FEATURE
<222> LOCATION: (8)..(8)
<223> OTHER INFORMATION: Xaa can be Glu or D-Glu
<220> FEATURE:
<221> NAME/KEY: MISC_FEATURE
<222> LOCATION: (10)..(10)
<223> OTHER INFORMATION: Xaa can be Glu or D-Glu
<220> FEATURE:
<221> NAME/KEY: MISC_FEATURE
```

```
<222> LOCATION: (12)..(12)
<223> OTHER INFORMATION: Xaa is citrulline

<400> SEQUENCE: 39

Arg Arg Xaa Cys Tyr Xaa Lys Xaa Pro Xaa Arg Xaa Cys Arg
1               5                   10

<210> SEQ ID NO 40
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is naphthyl-alanine
<220> FEATURE:
<221> NAME/KEY: MISC_FEATURE
<222> LOCATION: (6)..(6)
<223> OTHER INFORMATION: Xaa is citrulline
<220> FEATURE:
<221> NAME/KEY: MISC_FEATURE
<222> LOCATION: (8)..(8)
<223> OTHER INFORMATION: Xaa can be Glu or D-Glu
<220> FEATURE:
<221> NAME/KEY: MISC_FEATURE
<222> LOCATION: (12)..(12)
<223> OTHER INFORMATION: Xaa can be Glu or D-Glu

<400> SEQUENCE: 40

Arg Arg Xaa Cys Tyr Xaa Lys Xaa Pro Tyr Arg Xaa Cys Arg
1               5                   10

<210> SEQ ID NO 41
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is naphthyl-alanine
<220> FEATURE:
<221> NAME/KEY: MISC_FEATURE
<222> LOCATION: (6)..(6)
<223> OTHER INFORMATION: Xaa is citrulline
<220> FEATURE:
<221> NAME/KEY: MISC_FEATURE
<222> LOCATION: (8)..(8)
<223> OTHER INFORMATION: Xaa can be Glu or D-Glu
<220> FEATURE:
<221> NAME/KEY: MISC_FEATURE
<222> LOCATION: (12)..(12)
<223> OTHER INFORMATION: Xaa is citrulline

<400> SEQUENCE: 41

Arg Arg Xaa Cys Tyr Xaa Lys Xaa Pro Tyr Arg Xaa Cys Arg
1               5                   10

<210> SEQ ID NO 42
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is naphthyl-alanine
<220> FEATURE:
<221> NAME/KEY: MISC_FEATURE
<222> LOCATION: (6)..(6)
```

```
<223> OTHER INFORMATION: Xaa is citrulline
<220> FEATURE:
<221> NAME/KEY: MISC_FEATURE
<222> LOCATION: (8)..(8)
<223> OTHER INFORMATION: Xaa can be Glu or D-Glu
<220> FEATURE:
<221> NAME/KEY: MISC_FEATURE
<222> LOCATION: (12)..(12)
<223> OTHER INFORMATION: Xaa is citrulline

<400> SEQUENCE: 42

Arg Arg Xaa Cys Tyr Xaa Lys Xaa Pro Tyr Arg Xaa Cys Arg
 1               5                  10

<210> SEQ ID NO 43
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is naphthyl-alanine
<220> FEATURE:
<221> NAME/KEY: MISC_FEATURE
<222> LOCATION: (6)..(6)
<223> OTHER INFORMATION: Xaa is citrulline
<220> FEATURE:
<221> NAME/KEY: MISC_FEATURE
<222> LOCATION: (8)..(8)
<223> OTHER INFORMATION: Xaa can be Glu or D-Glu
<220> FEATURE:
<221> NAME/KEY: MISC_FEATURE
<222> LOCATION: (12)..(12)
<223> OTHER INFORMATION: Xaa is citrulline

<400> SEQUENCE: 43

Arg Arg Xaa Cys Tyr Xaa Lys Xaa Pro Tyr Arg Xaa Cys Arg
 1               5                  10

<210> SEQ ID NO 44
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa is naphthyl-alanine
<220> FEATURE:
<221> NAME/KEY: MISC_FEATURE
<222> LOCATION: (5)..(5)
<223> OTHER INFORMATION: Xaa is citrulline
<220> FEATURE:
<221> NAME/KEY: MISC_FEATURE
<222> LOCATION: (7)..(7)
<223> OTHER INFORMATION: Xaa can be Glu or D-Glu
<220> FEATURE:
<221> NAME/KEY: MISC_FEATURE
<222> LOCATION: (11)..(11)
<223> OTHER INFORMATION: Xaa is citrulline

<400> SEQUENCE: 44

Arg Xaa Cys Tyr Xaa Lys Xaa Pro Tyr Arg Xaa Cys Arg
 1               5                  10

<210> SEQ ID NO 45
<211> LENGTH: 14
<212> TYPE: PRT
<213> ORGANISM: Artificial Sequence
<220> FEATURE:
<223> OTHER INFORMATION: Synthetic
```

```
<220> FEATURE:
<221> NAME/KEY: MISC_FEATURE
<222> LOCATION: (3)..(3)
<223> OTHER INFORMATION: Xaa is naphthyl-alanine
<220> FEATURE:
<221> NAME/KEY: MISC_FEATURE
<222> LOCATION: (6)..(6)
<223> OTHER INFORMATION: Xaa is citrulline
<220> FEATURE:
<221> NAME/KEY: MISC_FEATURE
<222> LOCATION: (8)..(8)
<223> OTHER INFORMATION: Xaa can be Glu or D-Glu
<220> FEATURE:
<221> NAME/KEY: MISC_FEATURE
<222> LOCATION: (12)..(12)
<223> OTHER INFORMATION: Xaa is citrulline

<400> SEQUENCE: 45

Arg Arg Xaa Cys Tyr Xaa Lys Xaa Pro Tyr Arg Xaa Cys Arg
1               5                   10

<210> SEQ ID NO 46
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is naphthyl-alanine
<220> FEATURE:
<221> NAME/KEY: MISC_FEATURE
<222> LOCATION: (6)..(6)
<223> OTHER INFORMATION: Xaa is citrulline
<220> FEATURE:
<221> NAME/KEY: MISC_FEATURE
<222> LOCATION: (8)..(8)
<223> OTHER INFORMATION: Xaa can be Glu or D-Glu
<220> FEATURE:
<221> NAME/KEY: MISC_FEATURE
<222> LOCATION: (12)..(12)
<223> OTHER INFORMATION: Xaa is citrulline

<400> SEQUENCE: 46

Arg Arg Xaa Cys Tyr Xaa Lys Xaa Pro Tyr Arg Xaa Cys Arg
1               5                   10

<210> SEQ ID NO 47
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa is naphthyl-alanine
<220> FEATURE:
<221> NAME/KEY: MISC_FEATURE
<222> LOCATION: (5)..(5)
<223> OTHER INFORMATION: Xaa is citrulline
<220> FEATURE:
<221> NAME/KEY: MISC_FEATURE
<222> LOCATION: (7)..(7)
<223> OTHER INFORMATION: Xaa can be Glu or D-Glu
<220> FEATURE:
<221> NAME/KEY: MISC_FEATURE
<222> LOCATION: (11)..(11)
<223> OTHER INFORMATION: Xaa is citrulline

<400> SEQUENCE: 47

Arg Xaa Cys Tyr Xaa Lys Xaa Pro Tyr Arg Xaa Cys Arg
1               5                   10
```

```
<210> SEQ ID NO 48
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa is naphthyl-alanine
<220> FEATURE:
<221> NAME/KEY: MISC_FEATURE
<222> LOCATION: (5)..(5)
<223> OTHER INFORMATION: Xaa is citrulline
<220> FEATURE:
<221> NAME/KEY: MISC_FEATURE
<222> LOCATION: (7)..(7)
<223> OTHER INFORMATION: Xaa can be Glu or D-Glu
<220> FEATURE:
<221> NAME/KEY: MISC_FEATURE
<222> LOCATION: (11)..(11)
<223> OTHER INFORMATION: Xaa is citrulline

<400> SEQUENCE: 48

Arg Xaa Cys Tyr Xaa Lys Xaa Pro Tyr Arg Xaa Cys Arg
1               5                   10

<210> SEQ ID NO 49
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa is naphthyl-alanine
<220> FEATURE:
<221> NAME/KEY: MISC_FEATURE
<222> LOCATION: (5)..(5)
<223> OTHER INFORMATION: Xaa is citrulline
<220> FEATURE:
<221> NAME/KEY: MISC_FEATURE
<222> LOCATION: (7)..(7)
<223> OTHER INFORMATION: Xaa can be Glu or D-Glu
<220> FEATURE:
<221> NAME/KEY: MISC_FEATURE
<222> LOCATION: (11)..(11)
<223> OTHER INFORMATION: Xaa is citrulline

<400> SEQUENCE: 49

Arg Xaa Cys Tyr Xaa Lys Xaa Pro Tyr Arg Xaa Cys Arg
1               5                   10

<210> SEQ ID NO 50
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa is naphthyl-alanine
<220> FEATURE:
<221> NAME/KEY: MISC_FEATURE
<222> LOCATION: (5)..(5)
<223> OTHER INFORMATION: Xaa is citrulline
<220> FEATURE:
<221> NAME/KEY: MISC_FEATURE
<222> LOCATION: (7)..(7)
<223> OTHER INFORMATION: Xaa can be Glu or D-Glu
<220> FEATURE:
<221> NAME/KEY: MISC_FEATURE
<222> LOCATION: (11)..(11)
```

<223> OTHER INFORMATION: Xaa is citrulline

<400> SEQUENCE: 50

Arg Xaa Cys Tyr Xaa Lys Xaa Pro Tyr Arg Xaa Cys Arg
1               5                   10

<210> SEQ ID NO 51
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa is naphthyl-alanine
<220> FEATURE:
<221> NAME/KEY: MISC_FEATURE
<222> LOCATION: (5)..(5)
<223> OTHER INFORMATION: Xaa is citrulline
<220> FEATURE:
<221> NAME/KEY: MISC_FEATURE
<222> LOCATION: (7)..(7)
<223> OTHER INFORMATION: Xaa can be Glu or D-Glu
<220> FEATURE:
<221> NAME/KEY: MISC_FEATURE
<222> LOCATION: (11)..(11)
<223> OTHER INFORMATION: Xaa is citrulline

<400> SEQUENCE: 51

Arg Xaa Cys Tyr Xaa Lys Xaa Pro Tyr Arg Xaa Cys Arg
1               5                   10

<210> SEQ ID NO 52
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa is naphthyl-alanine
<220> FEATURE:
<221> NAME/KEY: MISC_FEATURE
<222> LOCATION: (5)..(5)
<223> OTHER INFORMATION: Xaa is citrulline
<220> FEATURE:
<221> NAME/KEY: MISC_FEATURE
<222> LOCATION: (7)..(7)
<223> OTHER INFORMATION: Xaa can be Glu or D-Glu
<220> FEATURE:
<221> NAME/KEY: MISC_FEATURE
<222> LOCATION: (11)..(11)
<223> OTHER INFORMATION: Xaa is citrulline

<400> SEQUENCE: 52

Arg Xaa Cys Tyr Xaa Lys Xaa Pro Tyr Arg Xaa Cys Arg
1               5                   10

<210> SEQ ID NO 53
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa is naphthyl-alanine
<220> FEATURE:
<221> NAME/KEY: MISC_FEATURE
<222> LOCATION: (5)..(5)
<223> OTHER INFORMATION: Xaa is citrulline

```
<220> FEATURE:
<221> NAME/KEY: MISC_FEATURE
<222> LOCATION: (7)..(7)
<223> OTHER INFORMATION: Xaa can be Glu or D-Glu
<220> FEATURE:
<221> NAME/KEY: MISC_FEATURE
<222> LOCATION: (11)..(11)
<223> OTHER INFORMATION: Xaa is citrulline

<400> SEQUENCE: 53

Arg Xaa Cys Tyr Xaa Lys Xaa Pro Tyr Arg Xaa Cys Arg
1               5                   10

<210> SEQ ID NO 54
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<220> FEATURE:
<221> NAME/KEY: MISC_FEATURE
<222> LOCATION: (2)..(2)
<223> OTHER INFORMATION: Xaa is naphthyl-alanine
<220> FEATURE:
<221> NAME/KEY: MISC_FEATURE
<222> LOCATION: (5)..(5)
<223> OTHER INFORMATION: Xaa is citrulline
<220> FEATURE:
<221> NAME/KEY: MISC_FEATURE
<222> LOCATION: (7)..(7)
<223> OTHER INFORMATION: Glu can be Dglu
<220> FEATURE:
<221> NAME/KEY: MISC_FEATURE
<222> LOCATION: (11)..(11)
<223> OTHER INFORMATION: Xaa is citrulline

<400> SEQUENCE: 54

Arg Xaa Cys Tyr Xaa Lys Xaa Pro Tyr Arg Xaa Cys Arg
1               5                   10

<210> SEQ ID NO 55
<211> LENGTH: 13
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (2)..(2)
<223> OTHER INFORMATION: Xaa is naphthyl-alanine
<220> FEATURE:
<221> NAME/KEY: MISC_FEATURE
<222> LOCATION: (5)..(5)
<223> OTHER INFORMATION: Xaa is citrulline
<220> FEATURE:
<221> NAME/KEY: MISC_FEATURE
<222> LOCATION: (7)..(7)
<223> OTHER INFORMATION: Glu can be Dglu
<220> FEATURE:
<221> NAME/KEY: MISC_FEATURE
<222> LOCATION: (11)..(11)
<223> OTHER INFORMATION: Xaa is citrulline

<400> SEQUENCE: 55

Arg Xaa Cys Tyr Xaa Lys Xaa Pro Tyr Arg Xaa Cys Arg
1               5                   10

<210> SEQ ID NO 56
<211> LENGTH: 13
<212> TYPE: PRT
<213> ORGANISM: Artificial Sequence
<220> FEATURE:
```

-continued

```
<223> OTHER INFORMATION: Synthetic
<220> FEATURE:
<221> NAME/KEY: MISC_FEATURE
<222> LOCATION: (2)..(2)
<223> OTHER INFORMATION: Xaa is naphthyl-alanine
<220> FEATURE:
<221> NAME/KEY: MISC_FEATURE
<222> LOCATION: (5)..(5)
<223> OTHER INFORMATION: Xaa is citrulline
<220> FEATURE:
<221> NAME/KEY: MISC_FEATURE
<222> LOCATION: (7)..(7)
<223> OTHER INFORMATION: Glu can be Dglu
<220> FEATURE:
<221> NAME/KEY: MISC_FEATURE
<222> LOCATION: (11)..(11)
<223> OTHER INFORMATION: Xaa is citrulline

<400> SEQUENCE: 56

Arg Xaa Cys Tyr Xaa Lys Xaa Pro Tyr Arg Xaa Cys Arg
1               5                   10

<210> SEQ ID NO 57
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is naphthyl-alanine
<220> FEATURE:
<221> NAME/KEY: MISC_FEATURE
<222> LOCATION: (6)..(6)
<223> OTHER INFORMATION: Xaa is citrulline
<220> FEATURE:
<221> NAME/KEY: MISC_FEATURE
<222> LOCATION: (8)..(8)
<223> OTHER INFORMATION: Xaa is D-citrulline
<220> FEATURE:
<221> NAME/KEY: MISC_FEATURE
<222> LOCATION: (12)..(12)
<223> OTHER INFORMATION: Xaa is citrulline

<400> SEQUENCE: 57

Arg Arg Xaa Cys Tyr Xaa Lys Xaa Pro Tyr Arg Xaa Cys Arg
1               5                   10

<210> SEQ ID NO 58
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is naphthyl-alanine
<220> FEATURE:
<221> NAME/KEY: MISC_FEATURE
<222> LOCATION: (6)..(6)
<223> OTHER INFORMATION: Xaa is citrulline
<220> FEATURE:
<221> NAME/KEY: MISC_FEATURE
<222> LOCATION: (8)..(8)
<223> OTHER INFORMATION: Xaa is D-citrulline
<220> FEATURE:
<221> NAME/KEY: MISC_FEATURE
<222> LOCATION: (12)..(12)
<223> OTHER INFORMATION: Xaa is citrulline

<400> SEQUENCE: 58

Arg Arg Xaa Cys Tyr Xaa Lys Xaa Pro Tyr Arg Xaa Cys Arg
1               5                   10
```

```
<210> SEQ ID NO 59
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is naphthyl-alanine
<220> FEATURE:
<221> NAME/KEY: MISC_FEATURE
<222> LOCATION: (8)..(8)
<223> OTHER INFORMATION: Xaa can be Lys or D-Lys
<220> FEATURE:
<221> NAME/KEY: MISC_FEATURE
<222> LOCATION: (12)..(12)
<223> OTHER INFORMATION: Xaa is citrulline

<400> SEQUENCE: 59

Arg Arg Xaa Cys Tyr Arg Lys Xaa Pro Tyr Arg Xaa Cys Arg
1               5                   10

<210> SEQ ID NO 60
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is naphthyl-alanine
<220> FEATURE:
<221> NAME/KEY: MISC_FEATURE
<222> LOCATION: (6)..(6)
<223> OTHER INFORMATION: Xaa is citrulline
<220> FEATURE:
<221> NAME/KEY: MISC_FEATURE
<222> LOCATION: (8)..(8)
<223> OTHER INFORMATION: Xaa can be Lys or D-Lys
<220> FEATURE:
<221> NAME/KEY: MISC_FEATURE
<222> LOCATION: (12)..(12)
<223> OTHER INFORMATION: Xaa is citrulline

<400> SEQUENCE: 60

Arg Arg Xaa Cys Tyr Xaa Arg Xaa Pro Tyr Arg Xaa Cys Arg
1               5                   10

<210> SEQ ID NO 61
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is naphthyl-alanine
<220> FEATURE:
<221> NAME/KEY: MISC_FEATURE
<222> LOCATION: (6)..(6)
<223> OTHER INFORMATION: Xaa is citrulline
<220> FEATURE:
<221> NAME/KEY: MISC_FEATURE
<222> LOCATION: (8)..(8)
<223> OTHER INFORMATION: Xaa can be Lys or D-Lys
<220> FEATURE:
<221> NAME/KEY: MISC_FEATURE
<222> LOCATION: (12)..(12)
<223> OTHER INFORMATION: Xaa is citrulline

<400> SEQUENCE: 61
```

Arg Arg Xaa Cys Tyr Xaa Arg Xaa Pro Tyr Arg Xaa Cys Arg
1               5                   10

<210> SEQ ID NO 62
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is naphthyl-alanine
<220> FEATURE:
<221> NAME/KEY: MISC_FEATURE
<222> LOCATION: (6)..(6)
<223> OTHER INFORMATION: Xaa is citrulline
<220> FEATURE:
<221> NAME/KEY: MISC_FEATURE
<222> LOCATION: (8)..(8)
<223> OTHER INFORMATION: Xaa can be Lys or D-Lys
<220> FEATURE:
<221> NAME/KEY: MISC_FEATURE
<222> LOCATION: (12)..(12)
<223> OTHER INFORMATION: Xaa is citrulline

<400> SEQUENCE: 62

Arg Arg Xaa Cys Tyr Xaa Lys Xaa Pro Tyr Arg Xaa Cys Arg
1               5                   10

<210> SEQ ID NO 63
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is naphthyl-alanine
<220> FEATURE:
<221> NAME/KEY: MISC_FEATURE
<222> LOCATION: (8)..(8)
<223> OTHER INFORMATION: Xaa is D-citrulline
<220> FEATURE:
<221> NAME/KEY: MISC_FEATURE
<222> LOCATION: (12)..(12)
<223> OTHER INFORMATION: Xaa is citrulline

<400> SEQUENCE: 63

Arg Arg Xaa Cys Tyr Arg Lys Xaa Pro Tyr Arg Xaa Cys Arg
1               5                   10

<210> SEQ ID NO 64
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is naphthyl-alanine
<220> FEATURE:
<221> NAME/KEY: MISC_FEATURE
<222> LOCATION: (6)..(6)
<223> OTHER INFORMATION: Xaa is citrulline
<220> FEATURE:
<221> NAME/KEY: MISC_FEATURE
<222> LOCATION: (8)..(8)
<223> OTHER INFORMATION: Xaa can be Lys or D-Lys
<220> FEATURE:
<221> NAME/KEY: MISC_FEATURE
<222> LOCATION: (12)..(12)

```
<223> OTHER INFORMATION: Xaa is citrulline

<400> SEQUENCE: 64

Arg Arg Xaa Cys Tyr Xaa Lys Xaa Pro Tyr Arg Xaa Cys Arg
1               5                   10

<210> SEQ ID NO 65
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is naphthyl-alanine
<220> FEATURE:
<221> NAME/KEY: MISC_FEATURE
<222> LOCATION: (6)..(6)
<223> OTHER INFORMATION: Xaa is citrulline
<220> FEATURE:
<221> NAME/KEY: MISC_FEATURE
<222> LOCATION: (8)..(8)
<223> OTHER INFORMATION: Xaa can be Glu or D-Glu
<220> FEATURE:
<221> NAME/KEY: MISC_FEATURE
<222> LOCATION: (12)..(12)
<223> OTHER INFORMATION: Xaa is citrulline

<400> SEQUENCE: 65

Arg Arg Xaa Cys Tyr Xaa Lys Xaa Pro Tyr Arg Xaa Cys Arg
1               5                   10

<210> SEQ ID NO 66
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is naphthyl-alanine
<220> FEATURE:
<221> NAME/KEY: MISC_FEATURE
<222> LOCATION: (6)..(6)
<223> OTHER INFORMATION: Xaa is citrulline
<220> FEATURE:
<221> NAME/KEY: MISC_FEATURE
<222> LOCATION: (8)..(8)
<223> OTHER INFORMATION: Xaa can be Glu or D-Glu
<220> FEATURE:
<221> NAME/KEY: MISC_FEATURE
<222> LOCATION: (12)..(12)
<223> OTHER INFORMATION: Xaa is citrulline

<400> SEQUENCE: 66

Arg Arg Xaa Cys Tyr Xaa Lys Xaa Pro Tyr Arg Xaa Cys Arg
1               5                   10

<210> SEQ ID NO 67
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is naphthyl-alanine
<220> FEATURE:
<221> NAME/KEY: MISC_FEATURE
<222> LOCATION: (6)..(6)
<223> OTHER INFORMATION: Xaa is citrulline
```

```
<220> FEATURE:
<221> NAME/KEY: MISC_FEATURE
<222> LOCATION: (8)..(8)
<223> OTHER INFORMATION: Xaa can be Glu or D-Glu
<220> FEATURE:
<221> NAME/KEY: MISC_FEATURE
<222> LOCATION: (12)..(12)
<223> OTHER INFORMATION: Xaa is citrulline

<400> SEQUENCE: 67

Arg Arg Xaa Cys Tyr Xaa Lys Xaa Pro Tyr Arg Xaa Cys Arg
1               5                   10

<210> SEQ ID NO 68
<211> LENGTH: 14
<212> TYPE: PRT
<213> ORGANISM: Artificial Sequence
<220> FEATURE:
<223> OTHER INFORMATION: Synthetic
<220> FEATURE:
<221> NAME/KEY: MISC_FEATURE
<222> LOCATION: (3)..(3)
<223> OTHER INFORMATION: Xaa is naphthyl-alanine
<220> FEATURE:
<221> NAME/KEY: MISC_FEATURE
<222> LOCATION: (6)..(6)
<223> OTHER INFORMATION: Xaa is citrulline
<220> FEATURE:
<221> NAME/KEY: MISC_FEATURE
<222> LOCATION: (8)..(8)
<223> OTHER INFORMATION: Xaa can be Glu or D-Glu
<220> FEATURE:
<221> NAME/KEY: MISC_FEATURE
<222> LOCATION: (12)..(12)
<223> OTHER INFORMATION: Xaa is citrulline

<400> SEQUENCE: 68

Arg Arg Xaa Cys Tyr Xaa Lys Xaa Pro Tyr Arg Xaa Cys Arg
1               5                   10
```

CXCR4 ANTAGONIST AND USE THEREOF

CROSS REFERENCE TO RELATED APPLICATIONS

The present application is a divisional of U.S. patent application Ser. No. 12/172,007, filed on Jul. 11, 2008, which in turn is a divisional of U.S. patent application Ser. No. 10/525,838, filed on Oct. 14, 2005, now U.S. Pat. No. 7,423,007, which in turn is a 35 U.S.C. §371 National Phase Entry Application from PCT/JP2003/010753, filed on Aug. 26, 2003, which claims priority under 35 U.S.C. §119 to Japanese Patent Application No. 2002247843, filed on Aug. 27, 2002, the contents of each of which are incorporated herein in their entireties.

TECHNICAL FIELD

The present invention relates to compounds having CXCR4 antagonistic action, and to preventive and/or therapeutic medicines containing such compounds for cancers and chronic rheumatoid arthritis.

BACKGROUND ART

Many hormones and neurotransmitters regulate vital functions through specific receptors existing in cell membranes.

Many of these receptors conduct intracellular signaling through the activation of coupled guanine nucleotide-binding protein (as may be hereafter abbreviated to "G-protein"). Also, these receptors are collectively called G-protein-coupled receptors (GPCR) or 7 trans-membrane receptors (7TMR), as they have common structures having seven transcytomembrane domains.

As one of such G-protein-coupled receptors, a human receptor protein coded by CXCR4 gene is known [Journal of biological chemistry, Vol. 273, 4754 (1998)].

Also, CXCL12/SDF-1α, which is a physiologically active peptide functioning as a ligand of the above-mentioned CXCR4, is known [Science, Vol. 261, 600-603 (1993)].

Certain peptidic compounds having antagonistic action against CXCR4 are disclosed and their anti-HIV activity is described in Fujii, International Publication WO02/20561 Mar. 14, 2003.

Cancer metastasis is one of the critical factors affecting the life expectancy of patients. It is reported that the expression of CXCR4 is enhanced in breast cancer cells, etc., and that the expression of CXCL12/SDF-1α which is a ligand of CXCR4 is enhanced in cancer-metastasized organs (lymph nodes, lungs, livers and bones) [Nature, Vol. 410, 50-56 (2001)]. Also, in chronic rheumatoid arthritis, the infiltration of CD4 positive memmory T-cells into articular cavity fluids affects the progression of the conditions. It is reported that in CD4 positive T-cells in articular cavity fluids of patients suffering from chronic rheumatoid arthritis, the expression of CXCR4 genes is enhanced, and that the expression of CXCL12/SDF-1α genes is enhanced in articular synovial membrane tissues [Journal of Immunology, Vol. 165, 6590-98 (2000)].

The present invention aims at providing novel means using CXCR4 antagonistic compounds for the prevention and/or therapy of cancers and chronic rheumatoid arthritis. Also, the present invention provides novel compounds, in particular, various oligopeptides with common structures, which have preventive and/or therapeutic activity for cancers and chronic rheumatoid arthritis.

DISCLOSURE OF THE INVENTION

The inventors of the present invention were dedicated to studying possibilities of solving the above-mentioned problem, and as a result, have discovered that CXCR4 antagonistic compounds previously considered effective as chemotherapeutics for AIDS are effective for the prevention and/or therapy of cancers, including metastatic cancers, and chronic rheumatoid arthritis, and have completed the present invention through further research efforts.

That is, the present invention relates to the followings:

(1) Preventive and/or therapeutic medicines for cancers and chronic rheumatoid arthritis, containing a peptide indicated by the following formula (Ia) or a salt thereof:

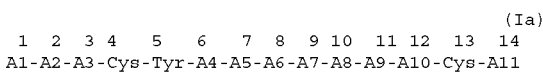

In this formula:

A1 is an arginine, lysine, ornithine, citrulline, alanine or glutamic acid residue which may be derivatized at N-terminal, or A1 is deleted;

A2 represents an arginine or glutamic acid residue if A1 is an arginine, lysine, ornithine, citrulline, alanine or glutamic acid residue which may be derivatized at N-terminal, or A2 represents an arginine or glutamic acid residue which may be derivatized at N-terminal if A1 is deleted;

A3 represents an aromatic amino acid residue;

A4, A5 and A9 each independently represents an arginine, lysine, ornithine, citrulline, alanine or glutamic acid residue;

A6 represents a proline, glycine, ornithine, lysine, alanine, citrulline, arginine or glutamic acid residue;

A7 represents a proline, glycine, ornithine, lysine, alanine, citrulline or arginine residue;

A8 represents a tyrosine, phenylalanine, alanine, naphthylalanine, citrulline or glutamic acid residue;

A10 represents a citrulline, glutamic acid, arginine or lysine residue;

A11 represents an arginine, glutamic acid, lysine or citrulline residue which may be derivatized at C-terminal;

In the above formula, Cys represents a cysteine residue, Tyr represents a tyrosine residue, the cysteine residue of the 4-position or the 13-position can be the combination by disulfide bond, and the amino acid can be either L or D form.

(2) Preventive and/or therapeutic medicines stated in (1).

In the above formula (Ia):

A1 is an arginine, citrulline, alanine or glutamic acid residue which may be derivatized at N-terminal, or A1 is deleted;

A2 represents an arginine or glutamic acid residue if A1 is an arginine, citrulline, alanine or glutamic acid residue which may be derivatized at N-terminal, or A2 represents an arginine or glutamic acid residue which may be derivatized at N-terminal if A1 is deleted;

A4 represents an arginine, citrulline, alanine or glutamic acid residue;

A5 represents an arginine, citrulline, alanine, lysine or glutamic acid residue;

A6 represents a lysine, alanine, citrulline or glutamic acid residue;

A7 represents a proline or alanine residue;

A8 represents a tyrosine, alanine or glutamic acid residue;

A9 represents an arginine, citrulline or glutamic acid residue;

A10 represents a citrulline or glutamic acid residue;

A11 represents an arginine or glutamic acid residue which may be derivatized at C-terminal (3) Peptide represented by the following formula (Ib) or a salt thereof:

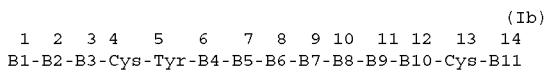

(Ib)

1 2 3 4 5 6 7 8 9 10 11 12 13 14
B1-B2-B3-Cys-Tyr-B4-B5-B6-B7-B8-B9-B10-Cys-B11

In this formula:

B1 is a glutamic acid residue which may be derivatized at N-terminal, or B1 is deleted;

B2 represents an arginine or glutamic acid residue if B1 is a glutamic acid residue which may be derivatized at N-terminal, or B2 represents an arginine or glutamic acid residue which may be derivatized at N-terminal if B1 is deleted;

B3 represents an aromatic amino acid residue;

B4, B5 and B9 each independently represents an arginine, lysine, ornithine, citrulline, alanine or glutamic acid residue;

B6 represents a proline, glycine, ornithine, lysine, alanine, citrulline, arginine or glutamic acid residue;

B7 represents a proline, glycine, ornithine, lysine, alanine, citrulline or arginine residue;

B8 represents a tyrosine, phenylalanine, alanine, naphthylalanine, citrulline or glutamic acid residue;

B10 represents a citrulline, glutamic acid, arginine or lysine residue;

B11 represents an arginine, glutamic acid, lysine or citrulline residue which may be derivatized at C-terminal;

In the above formula, Cys represents a cysteine residue, Tyr represents a tyrosine residue, the cysteine residue of the 4-position or the 13-position can be the combination by disulfide bond, and the amino acid can be either L or D form.

(4) Peptide or its salt stated in (3).

B1 is a glutamic acid residue which may be derivatized at N-terminal (5) Peptide indicated by the following formula (Ic) or a salt thereof:

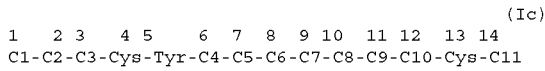

(Ic)

1 2 3 4 5 6 7 8 9 10 11 12 13 14
C1-C2-C3-Cys-Tyr-C4-C5-C6-C7-C8-C9-C10-Cys-C11

In this formula:

C1 is an ariginine, lysine, ornithin, citrulline, alanine or glutamic acid residue which may be derivatized at N-terminal, or C1 is deleted;

C2 represents a glutamic acid residue if C1 is an ariginine, lysine, ornithine, citrulline, alanine or glutamic acid residue which may be derivatized at N-terminal, or C2 represents a glutamic acid residue which may be derivatized at N-terminal if C1 is deleted;

C3 represents an aromatic amino acid residue;

C4, C5 and C9 each independently represents an arginine, lysine, ornithine, citrulline, alanine or glutamic acid residue;

C6 represents a proline, glycine, ornithine, lysine, alanine, citrulline, arginine or glutamic acid residue;

C7 represents a proline, glycine, ornithine, lysine, alanine, citrulline or arginine residue;

C8 represents a tyrosine, phenylalanine, alanine, naphthylalanine, citrulline or glutamic acid residue;

C10 represents a citrulline, glutamic acid, arginine or lysine residue;

C11 represents an arginine, glutamic acid, lysine or citrulline residue which may be derivatized at C-terminal;

In the above formula, Cys represents a cysteine residue, Tyr represents a tyrosine residue, the cysteine residue of the 4-position or the 13-position can be the combination by disulfide bond, and the amino acid can be either L or D form.

(6) Peptide represented by the following formula (Id) or a salt thereof:

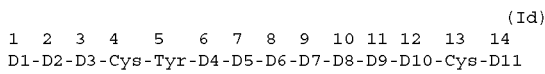

(Id)

1 2 3 4 5 6 7 8 9 10 11 12 13 14
D1-D2-D3-Cys-Tyr-D4-D5-D6-D7-D8-D9-D10-Cys-D11

In this formula:

D1 is an arginine, lysine, ornithine, citrulline, alanine or glutamic acid residue which may be derivatized at N-terminal, or D1 is deleted;

D2 represents an arginine or glutamic acid residue if D1 is an arginine, lysine, ornithine, citrulline, alanine or glutamic acid residue which may be derivatized at N-terminal, or D2 represents an arginine or glutamic acid residue which may be derivatized at N-terminal if D1 is deleted;

D3 represents an aromatic amino acid residue;

D4 represents a glutamic acid residue;

D5 and D9 each independently represents an arginine, lysine, ornithine, citrulline, alanine or glutamic acid residue;

D6 represents a proline, glycine, ornithine, lysine, alanine, citrulline, arginine or glutamic acid residue;

D7 represents a proline, glycine, ornithine, lysine, alanine, citrulline or arginine residue;

D8 represents a tyrosine, phenylalanine, alanine, naphthylalanine, citrulline or glutamic acid residue;

D10 represents a citrulline, glutamic acid, arginine or lysine residue;

D11 represents an arginine, glutamic acid, lysine or citrulline residue which may be derivatized at C-terminal;

In the above formula, Cys represents a cysteine residue, Tyr represents a tyrosine residue, the cysteine residue of the 4-position or the 13-position can be the combination by disulfide bond, and the amino acid can be either L or D form.

(7) Peptide indicated by the following formula (Ie) or a salt thereof:

(Ie)

1 2 3 4 5 6 7 8 9 10 11 12 13 14
E1-E2-E3-Cys-Tyr-E4-E5-E6-E7-E8-E9-E10-Cys-E11

In this formula:

E1 is an arginine, lysine, ornithine, citrulline, alanine or glutamic acid residue which may be derivatized at N-terminal, or E1 is deleted;

E2 represents an arginine or glutamic acid residue if E1 is an arginine, lysine, ornithine, citrulline, alanine or glutamic acid residue which may be derivatized at N-terminal, or E2 represents an arginine or glutamic acid residue which may be derivatized at N-terminal if E1 is deleted;

E3 represents an aromatic amino acid residue;

E4 and E9 each independently represents an arginine, lysine, ornithine, citrulline, alanine or glutamic acid residue;

E5 represents an arginine or glutamic acid residue;

E6 represents a proline, glycine, ornithine, lysine, alanine, citrulline, arginine or glutamic acid residue;

E7 represents a proline, glycine, ornithine, lysine, alanine, citrulline or arginine residue;

E8 represents a tyrosine, phenylalanine, alanine, naphthylalanine, citrulline or glutamic acid residue;

E10 represents a citrulline, glutamic acid, arginine or lysine residue;

E11 represents an arginine, glutamic acid, lysine or citrulline residue which may be derivatized at C-terminal;

In the above formula, Cys represents a cysteine residue, Tyr represents a tyrosine residue, the cysteine residue of the 4-position or the 13-position can be the combination by disulfide bond, and the amino acid can be either L or D form.

(8) Peptide or its salt stated in (7).
E5 represents a glutamic acid residue.
(9) Peptide represented by the following formula (If) or a salt thereof:

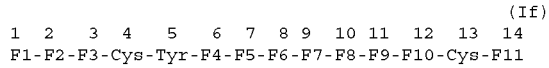
```
 1  2  3  4  5  6  7  8  9 10 11 12 13 14
F1-F2-F3-Cys-Tyr-F4-F5-F6-F7-F8-F9-F10-Cys-F11
```

In this formula:

F1 is an arginine, lysine, ornithine, citrulline, alanine or glutamic acid residue which may be derivatized at N-terminal, or F1 is deleted;

F2 represents an arginine or glutamic acid residue if F1 is an arginine, lysine, ornithine, citrulline, alanine or glutamic acid residue which may be derivatized at N-terminal, or F2 represents an arginine or glutamic acid residue which may be derivatized at N-terminal if F1 is deleted;

F3 represents an aromatic amino acid residue;

F4, F5 and F9 each independently represents an arginine, lysine, ornithine, citrulline, alanine or glutamic acid residue;

F6 represents a glutamic acid residue;

F7 represents a proline, glycine, ornithine, lysine, alanine, citrulline or arginine residue;

F8 represents a tyrosine, phenylalanine, alanine, naphthylalanine, citrulline or glutamic acid residue;

F10 represents a citrulline, glutamic acid, arginine or lysine residue;

F11 represents an arginine, glutamic acid, lysine or citrulline residue which may be derivatized at C-terminal;

In the above formula, Cys represents a cysteine residue, Tyr represents a tyrosine residue, the cysteine residue of the 4-position or the 13-position can be the combination by disulfide bond, and the amino acid can be either L or D form.

(10) Peptide represented by the following formula (Ig) or a salt thereof:

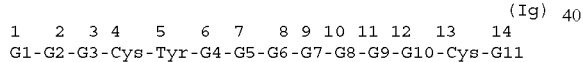
```
 1  2  3  4  5  6  7  8  9 10 11 12 13 14
G1-G2-G3-Cys-Tyr-G4-G5-G6-G7-G8-G9-G10-Cys-G11
```

In this formula:

G1 is an arginine, lysine, ornithine, citrulline, alanine or glutamic acid residue which may be derivatized at N-terminal, or G1 is deleted;

G2 represents an arginine or glutamic acid residue if G1 is an arginine, lysine, ornithine, citrulline, alanine or glutamic acid residue which may be derivatized at N-terminal, or G2 represents an arginine or glutamic acid residue which may be derivatized at N-terminal if G1 is deleted;

G3 represents an aromatic amino acid residue;

G4, G5 and G9 each independently represents an arginine, lysine, ornithine, citrulline, alanine or glutamic acid residue;

G6 represents a proline, glycine, ornithine, lysine, alanine, citrulline, arginine or glutamic acid residue;

G7 represents a proline, glycine, ornithine, lysine, alanine, citrulline or arginine residue;

G8 represents a glutamic acid residue;

G10 represents a citrulline, glutamic acid, arginine or lysine residue;

G11 represents an arginine, glutamic acid, lysine or citrulline residue which may be derivatized at C-terminal;

In the above formula, Cys represents a cysteine residue, Tyr represents a tyrosine residue, the cysteine residue of the 4-position or the 13-position can be the combination by disulfide bond, and the amino acid can be either L or D form.

(11) Peptide represented by the following formula (Ih) or a salt thereof:

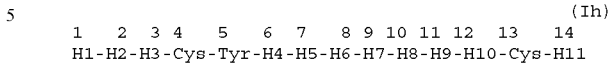
```
 1  2  3  4  5  6  7  8  9 10 11 12 13 14
H1-H2-H3-Cys-Tyr-H4-H5-H6-H7-H8-H9-H10-Cys-H11
```

In this formula:

H1 is an arginine, lysine, ornithine, citrulline, alanine or glutamic acid residue which may be derivatized at N-terminal, or H1 is deleted;

H2 represents an arginine or glutamic acid residue if H1 is an arginine, lysine, ornithine, citrulline, alanine or glutamic acid residue which may be derivatized at N-terminal, or H2 represents an arginine or glutamic acid residue which may be derivatized at N-terminal if H1 is deleted;

H3 represents an aromatic amino acid residue;

H4 and H5 each independently represents an arginine, lysine, ornithine, citrulline, alanine or glutamic acid residue;

H6 represents a proline, glycine, ornithine, lysine, alanine, citrulline, arginine or glutamic acid residue;

H7 represents a proline, glycine, ornithine, lysine, alanine, citrulline or arginine residue;

H8 represents a tyrosine, phenylalanine, alanine, naphthylalanine, citrulline or glutamic acid residue;

H9 represents a glutamic acid residue;

H10 represents a citrulline, glutamic acid, arginine or lysine residue;

H11 represents an arginine, glutamic acid, lysine or citrulline residue which may be derivatized at C-terminal;

In the above formula, Cys represents a cysteine residue, Tyr represents a tyrosine residue, the cysteine residue of the 4-position or the 13-position can be the combination by disulfide bond, and the amino acid can be either L or D form.

(12) Peptide represented by the following formula (Ii) or a salt thereof:

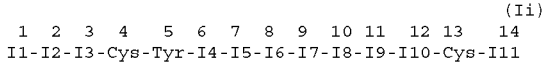
```
 1  2  3  4  5  6  7  8  9 10 11 12 13 14
I1-I2-I3-Cys-Tyr-I4-I5-I6-I7-I8-I9-I10-Cys-I11
```

In this formula:

I1 is an arginine, lysine, ornithine, citrulline, alanine or glutamic acid residue which may be derivatized at N-terminal, or I1 is deleted;

I2 represents an arginine or glutamic acid residue if I1 is an arginine, lysine, ornithine, citrulline, alanine or glutamic acid residue which may be derivatized at N-terminal, or I2 represents an arginine or glutamic acid residue which may be derivatized at N-terminal if I1 is deleted;

I3 represents an aromatic amino acid residue;

I4, I5 and I9 each independently represents an arginine, lysine, ornithine, citrulline, alanine or glutamic acid residue;

I6 represents a proline, glycine, ornithine, lysine, alanine, citrulline, arginine or glutamic acid residue;

I7 represents a proline, glycine, ornithine, lysine, alanine, citrulline or arginine residue;

I8 represents a tyrosine, phenylalanine, alanine, naphthylalanine, citrulline or glutamic acid residue;

I10 represents a glutamic acid, arginine or lysine residue;

I11 represents an arginine, glutamic acid, lysine or citrulline residue which may be derivatized at C-terminal;

In the above formula, Cys represents a cysteine residue, Tyr represents a tyrosine residue, the cysteine residue of the 4-position or the 13-position can be the combination by disulfide bond, and the amino acid can be either L or D form.

(13) Peptide represented by the following formula (Ij) or a salt thereof:

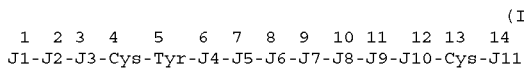

(Ij)

```
 1  2  3  4   5   6  7  8  9 10 11  12 13 14
J1-J2-J3-Cys-Tyr-J4-J5-J6-J7-J8-J9-J10-Cys-J11
```

In this formula:

J1 is an arginine, lysine, ornithine, citrulline, alanine or glutamic acid residue which may be derivatized at N-terminal, or J1 is deleted;

J2 represents an arginine or glutamic acid residue if J1 is an arginine, lysine, ornithine, citrulline, alanine or glutamic acid residue which may be derivatized at N-terminal, or J2 represents an arginine or glutamic acid residue which may be derivatized at N-terminal if J1 is deleted;

J3 represents an aromatic amino acid residue;

J4, J5 and J9 each independently represents an arginine, lysine, ornithine, citrulline, alanine or glutamic acid residue;

J6 represents a proline, glycine, ornithine, lysine, alanine, citrulline, arginine or glutamic acid residue;

J7 represents a proline, glycine, ornithine, lysine, alanine, citrulline or arginine residue;

J8 represents a tyrosine, phenylalanine, alanine, naphthylalanine, citrulline or glutamic acid residue;

J10 represents a citrulline, glutamic acid, arginine or lysine residue;

J11 represents a glutamic acid, lysine or citrulline residue which may be derivatized at C-terminal;

In the above formula, Cys represents a cysteine residue, Tyr represents a tyrosine residue, the cysteine residue of the 4-position or the 13-position can be the combination by disulfide bond, and the amino acid can be either L or D form.

(14) Peptide indicated in any of the following items (1)-(58) or a salt thereof:

| | | |
|---|---|---|
| (1) | Ac-Arg-Arg-Nal-Cys-Tyr-Cit-Lys-DLys-Pro-Tyr-Arg-Cit-Cys-Arg-OH; | [SEQ ID NO: 11] |
| (2) | Ac-Arg-Arg-Nal-Cys-Tyr-Arg-Lys-DCit-Pro-Tyr-Arg-Cit-Cys-Arg-OH; | [SEQ ID NO: 12] |
| (3) | Ac-Arg-Arg-Nal-Cys-Tyr-Cit-Lys-DCit-Pro-Tyr-Arg-Cit-Cys-Arg-OH; | [SEQ ID NO: 13] |
| (4) | Ac-Arg-Arg-Nal-Cys-Tyr-Cit-Lys-DLys-Pro-Tyr-Cit-Cit-Cys-Arg-OH; | [SEQ ID NO: 14] |
| (5) | Ac-Cit-Arg-Nal-Cys-Tyr-Cit-Lys-DLys-Pro-Tyr-Arg-Cit-Cys-Arg-OH; | [SEQ ID NO: 15] |
| (6) | Ac-Cit-Arg-Nal-Cys-Tyr-Arg-Lys-DCit-Pro-Tyr-Arg-Cit-Cys-Arg-OH; | [SEQ ID NO: 16] |
| (7) | Ac-Arg-Arg-Nal-Cys-Tyr-Arg-Lys-DCit-Pro-Tyr-Cit-Cit-Cys-Arg-OH; | [SEQ ID NO: 17] |
| (8) | Ac-Cit-Arg-Nal-Cys-Tyr-Arg-Lys-DLys-Pro-Tyr-Cit-Cit-Cys-Arg-OH; | [SEQ ID NO: 18] |
| (9) | Ac-Arg-Arg-Nal-Cys-Tyr-Cit-Lys-DCit-Pro-Tyr-Arg-Cit-Cys-Arg-NH$_2$; | [SEQ ID NO: 19] |
| (10) | Ac-Arg-Arg-Nal-Cys-Tyr-Cit-Lys-DLys-Pro-Tyr-Cit-Cit-Cys-Arg-NH$_2$; | [SEQ ID NO: 20] |
| (11) | Ac-Cit-Arg-Nal-Cys-Tyr-Cit-Lys-DLys-Pro-Tyr-Arg-Cit-Cys-Arg-NH$_2$; | [SEQ ID NO: 21] |
| (12) | Ac-Cit-Arg-Nal-Cys-Tyr-Arg-Lys-DCit-Pro-Tyr-Arg-Cit-Cys-Arg-NH$_2$; | [SEQ ID NO: 22] |
| (13) | Ac-Arg-Arg-Nal-Cys-Tyr-Arg-Lys-DCit-Pro-Tyr-Cit-Cit-Cys-Arg-NH$_2$; | [SEQ ID NO: 23] |
| (14) | Ac-Cit-Arg-Nal-Cys-Tyr-Arg-Lys-DLys-Pro-Tyr-Cit-Cit-Cys-Arg-NH$_2$; | [SEQ ID NO: 24] |
| (15) | H-DGlu-Arg-Nal-Cys-Tyr-Arg-Lys-DLys-Pro-Tyr-Arg-Cit-Cys-Arg-OH; | [SEQ ID NO: 25] |
| (16) | H-Arg-Glu-Nal-Cys-Tyr-Arg-Lys-DLys-Pro-Tyr-Arg-Cit-Cys-Arg-OH; | [SEQ ID NO: 26] |
| (17) | H-Arg-Arg-Nal-Cys-Tyr-Glu-Lys-DLys-Pro-Tyr-Arg-Cit-Cys-Arg-OH; | [SEQ ID NO: 27] |
| (18) | H-Arg-Arg-Nal-Cys-Tyr-Arg-Glu-DLys-Pro-Tyr-Arg-Cit-Cys-Arg-OH; | [SEQ ID NO: 28] |
| (19) | H-Arg-Arg-Nal-Cys-Tyr-Arg-Lys-DGlu-Pro-Tyr-Arg-Cit-Cys-Arg-OH; | [SEQ ID NO: 29] |
| (20) | H-Arg-Arg-Nal-Cys-Tyr-Arg-Lys-DLys-Pro-Tyr-Glu-Cit-Cys-Arg-OH; | [SEQ ID NO: 30] |
| (21) | H-Arg-Arg-Nal-Cys-Tyr-Arg-Lys-DLys-Pro-Tyr-Arg-Cit-Cys-Glu-OH; | [SEQ ID NO: 31] |
| (22) | H-Arg-Arg-Nal-Cys-Tyr-Cit-Lys-DGlu-Pro-Tyr-Arg-Cit-Cys-Arg-NH$_2$; | [SEQ ID NO: 32] |
| (23) | H-Arg-Arg-Nal-Cys-Tyr-DGlu-Lys-DCit-Pro-Tyr-Arg-Cit-Cys-Arg-NH$_2$; | [SEQ ID NO: 33] |
| (24) | H-Arg-Arg-Nal-Cys-Tyr-DGlu-Lys-DGlu-Pro-Tyr-Arg-Cit-Cys-Arg-NH$_2$; | [SEQ ID NO: 34] |
| (25) | H-DGlu-Arg-Nal-Cys-Tyr-Cit-Lys-DGlu-Pro-Tyr-Arg-Cit-Cys-Arg-NH$_2$; | [SEQ ID NO: 35] |
| (26) | H-Arg-Arg-Nal-Cys-Tyr-Cit-Lys-DGlu-Pro-DGlu-Arg-Cit-Cys-Arg-NH$_2$; | [SEQ ID NO: 36] |
| (27) | H-Arg-Arg-Nal-Cys-Tyr-Cit-Lys-DGlu-Pro-Tyr-Arg-DGlu-Cys-Arg-NH$_2$; | [SEQ ID NO: 37] |
| (28) | Ac-DGlu-Arg-Nal-Cys-Tyr-Cit-Lys-DGlu-Pro-Tyr-Arg-Cit-Cys-Arg-NH$_2$; | [SEQ ID NO: 38] |

-continued

| | | |
|---|---|---|
| (29) | Ac-Arg-Arg-Nal-Cys-Tyr-Cit-Lys-DGlu-Pro-DGlu-Arg-Cit-Cys-Arg-NH$_2$; | [SEQ ID NO: 39] |
| (30) | Ac-Arg-Arg-Nal-Cys-Tyr-Cit-Lys-DGlu-Pro-Tyr-Arg-DGlu-Cys-Arg-NH$_2$; | [SEQ ID NO: 40] |
| (31) | Ac-Arg-Arg-Nal-Cys-Tyr-Cit-Lys-DGlu-Pro-Tyr-Arg-Cit-Cys-Arg-NH$_2$; | [SEQ ID NO: 41] |
| (32) | guanyl-Arg-Arg-Nal-Cys-Tyr-Cit-Lys-DGlu-Pro-Tyr-Arg-Cit-Cys-Arg-NH$_2$; | [SEQ ID NO: 42] |
| (33) | TMguanyl-Arg-Arg-Nal-Cys-Tyr-Cit-Lys-DGlu-Pro-Tyr-Arg-Cit-Cys-Arg-NH$_2$; | [SEQ ID NO: 43] |
| (34) | TMguanyl-Arg-Nal-Cys-Tyr-Cit-Lys-DGlu-Pro-Tyr-Arg-Cit-Cys-Arg-NH$_2$; | [SEQ ID NO: 44] |
| (35) | 4F-benzoyl-Arg-Arg-Nal-Cys-Tyr-Cit-Lys-DGlu-Pro-Tyr-Arg-Cit-Cys-Arg-NH$_2$; | [SEQ ID NO: 45] |
| (36) | 2F-benzoyl-Arg-Arg-Nal-Cys-Tyr-Cit-Lys-DGlu-Pro-Tyr-Arg-Cit-Cys-Arg-NH$_2$; | [SEQ ID NO: 46] |
| (37) | APA-Arg-Nal-Cys-Tyr-Cit-Lys-DGlu-Pro-Tyr-Arg-Cit-Cys-Arg-NH$_2$; | [SEQ ID NO: 47] |
| (38) | desamino-R-Arg-Nal-Cys-Tyr-Cit-Lys-DGlu-Pro-Tyr-Arg-Cit-Cys-Arg-NH$_2$; | [SEQ ID NO: 48] |
| (39) | guanyl-Arg-Nal-Cys-Tyr-Cit-Lys-DGlu-Pro-Tyr-Arg-Cit-Cys-Arg-NH$_2$; | [SEQ ID NO: 49] |
| (40) | succinyl-Arg-Nal-Cys-Tyr-Cit-Lys-DGlu-Pro-Tyr-Arg-Cit-Cys-Arg-NH$_2$; | [SEQ ID NO: 50] |
| (41) | glutaryl-Arg-Nal-Cys-Tyr-Cit-Lys-DGlu-Pro-Tyr-Arg-Cit-Cys-Arg-NH$_2$; | [SEQ ID NO: 51] |
| (42) | deaminoTMG-APA-Arg-Nal-Cys-Tyr-Cit-Lys-DGlu-Pro-Tyr-Arg-Cit-Cys-Arg-NH$_2$; | [SEQ ID NO: 52] |
| (43) | nelfinaviryl-succinyl-Arg-Nal-Cys-Tyr-Cit-Lys-DGlu-Pro-Tyr-Arg-Cit-Cys-Arg-NH$_2$; | [SEQ ID NO: 53] |
| (44) | AZT-glutaryl-Arg-Nal-Cys-Tyr-Cit-Lys-DGlu-Pro-Tyr-Arg-Cit-Cys-Arg-NH$_2$; | [SEQ ID NO: 54] |
| (45) | R-CH2-Arg-Nal-Cys-Tyr-Cit-Lys-DGlu-Pro-Tyr-Arg-Cit-Cys-Arg-NH$_2$; | [SEQ ID NO: 55] |
| (46) | H-Arg-Nal-Cys-Tyr-Cit-Lys-DGlu-Pro-Tyr-Arg-Cit-Cys-Arg-NH$_2$; | [SEQ ID NO: 56] |
| (47) | TMguanyl-Arg-Arg-Nal-Cys-Tyr-Cit-Lys-DCit-Pro-Tyr-Arg-Cit-Cys-Arg-NH$_2$; | [SEQ ID NO: 57] |
| (48) | ACA-Arg-Arg-Nal-Cys-Tyr-Cit-Lys-DCit-Pro-Tyr-Arg-Cit-Cys-Arg-NH$_2$; | [SEQ ID NO: 58] |
| (49) | ACA-Arg-Arg-Nal-Cys-Tyr-Arg-Lys-DLys-Pro-Tyr-Arg-Cit-Cys-Arg-OH; | [SEQ ID NO: 59] |
| (50) | H-Arg-Arg-Nal-Cys-Tyr-Cit-Arg-DLys-Pro-Tyr-Arg-Cit-Cys-Arg-NH$_2$; | [SEQ ID NO: 60] |
| (51) | Ac-Arg-Arg-Nal-Cys-Tyr-Cit-Arg-DLys-Pro-Tyr-Arg-Cit-Cys-Arg-NH$_2$; | [SEQ ID NO: 61] |
| (52) | Ac-Arg-Arg-Nal-Cys-Tyr-Cit-Lys-DLys-Pro-Tyr-Arg-Cit-Cys-Arg-NH$_2$; | [SEQ ID NO: 62] |
| (53) | Ac-Arg-Arg-Nal-Cys-Tyr-Arg-Lys-DCit-Pro-Tyr-Arg-Cit-Cys-Arg-NH$_2$; | [SEQ ID NO: 63] |
| (54) | 4F-benzoyl-Arg-Arg-Nal-Cys-Tyr-Cit-Lys-DLys-Pro-Tyr-Arg-Cit-Cys-Arg-NH$_2$ | [SEQ ID NO: 64] |
| (55) | 4F-benzoyl-Arg-Arg-Nal-Cys-Tyr-Cit-Lys-DGlu-Pro-Tyr-Arg-Cit-Cys-Arg-NHMe | [SEQ ID NO: 65] |
| (56) | 4F-benzoyl-Arg-Arg-Nal-Cys-Tyr-Cit-Lys-DGlu-Pro-Tyr-Arg-Cit-Cys-Arg-NHEt | [SEQ ID NO: 66] |
| (57) | 4F-benzoyl-Arg-Arg-Nal-Cys-Tyr-Cit-Lys-DGlu-Pro-Tyr-Arg-Cit-Cys-Arg-NHiPr | [SEQ ID NO: 67] |
| (58) | 4F-benzoyl-Arg-Arg-Nal-Cys-Tyr-Cit-Lys-DGlu-Pro-Tyr-Arg-Cit-Cys-Arg-tyramine | [SEQ ID NO: 68] |

In each sequence, the symbol put in the left part of N-terminal amino acid shows derivatization or non-derivatization of amino group; H shows non-derivatization, Ac shows acetyl group, guanyl shows guanyl group, succinyl shows succinyl group, glutaryl shows glutaryl group, TMguanyl shows tetramethyl guanyl group, 2F-beozoyl shows 2-fluorobenzoyl group, 4F-benzoyl shows 4-fluorobenzoly group, APA shows 5-amino-pentanoyl group, ACA shows 6-amino-hexanoyl group, desamino-R shows 2-desamino-arginyl group, deaminoTMG-APA shows the following formula (II),

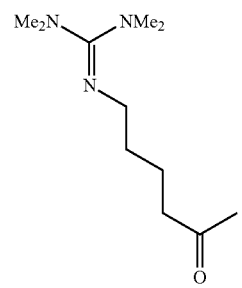

(II)

nelfinaviryl-succinyl shows the following formula (III)

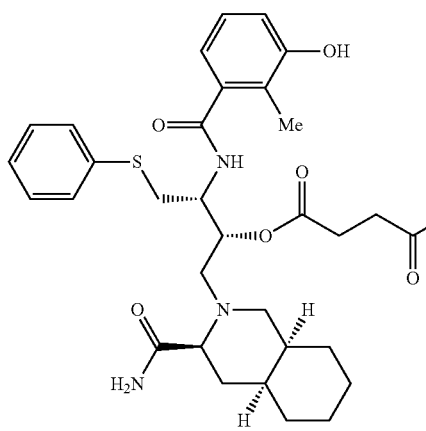

AZT-glutaryl shows the following formula (IV)

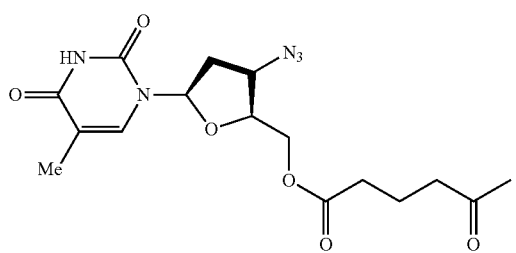

R—CH2 shows the following formula (V)

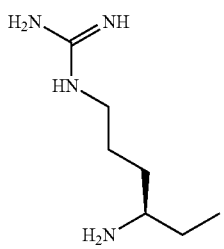

Arg shows L-arginine residue, NaI show L-3-2(2-naphtyl) alanine residue, Cys shows L-cysteine residue, Tyr shows L-tyrosine residue, Cit shows L-citrulline residue, Lys shows L-lysine residue, DLys shows D-lysine residue, Pro shows L-proline residue, DCit shows D-citrulline residue, DGlu shows D-glutamic acid residue, Glu shows L-glutamic acid residue, 2 cysteine residues are combined by intramolecular disulfide bond, the symbol attached to the right part of C-terminal amino acid shows derivatization or non-derivatization of carboxyl group, OH shows non-derivatization, $NH_2$ shows amidation by amino group, NHMe shows amidation by methyamino group, NHEt shows amidation by ethylamino group, NHiPr shows amidation by isopropylamino group, tyramine shows amidation by p-hydroxy phenyl ethylamino group.

(15) Pharmaceutical products containing any of the peptides stated in any of (3) to (14) or any salt of the peptide.

(16) CXCR4 antagonists belonging to the pharmaceutical products stated in (15).

(17) Preventive and/or therapeutic medicines for cancers or chronic rheumatoid arthritis belonging to the pharmaceutical products stated in (15).

(18) Medicines stated in (17) usable for breast cancer or pancreas cancer.

(19) Preventive and/or therapeutic methods for cancers or chronic rheumatoid arthritis by administration to mammalians of effective doses of a peptide stated in any of (3) to (14) or a salt thereof

(20) Use of a peptide stated in any of (3) to (14) or a salt thereof for the manufacturing of preventive and/or therapeutic medicines for cancers or chronic rheumatoid arthritis.

(21) Preventive and/or therapeutic methods for cancers or chronic rheumatoid arthritis by administration to mammalians of effective doses of a peptide represented by the following formula (Ia) or a salt thereof:

```
                                                    (Ia)
1 2 3   4   5    6    7   8   9 10    11 12  13   14
A1-A2-A3-Cys-Tyr-A4-A5-A6-A7-A8-A9-A10-Cys-A11
```

In this formula:

A1 is an arginine, lysine, ornithine, citrulline, alanine or glutamic acid residue which may be derivatized at N-terminal, or A1 is deleted;

A2 represents an arginine or glutamic acid residue if A1 are an arginine, lysine, ornithine, citrulline, alanine or glutamic acid residue which may be derivatized at N-terminal, or A2 represents an arginine or glutamic acid residue which may be derivatized at N-terminal if A1 is deleted;

A3 represents an aromatic amino acid residue;

A4, A5 and A9 each independently represents an arginine, lysine, ornithine, citrulline, alanine or glutamic acid residue;

A6 represents a proline, glycine, ornithine, lysine, alanine, citrulline, arginine or glutamic acid residue;

A7 represents a proline, glycine, ornithine, lysine, alanine, citrulline or arginine residue;

A8 represents a tyrosine, phenylalanine, alanine, naphthylalanine, citrulline or glutamic acid residue;

A10 represents a citrulline, glutamic acid, arginine or lysine residue;

A11 represents an arginine, glutamic acid, lysine or citrulline residue which may be derivatized at C-terminal;

In the above formula, Cys represents a cysteine residue, Tyr represents a tyrosine residue, the cysteine residue of the 4-position or the 13-position can be the combination by disulfide bond, and the amino acid can be either L or D form.

(22) Use of a peptide represented by the following formula (Ia) or a salt thereof for the manufacturing of preventive and/or therapeutic medicines for cancers or chronic rheumatoid arthritis:

```
                                                    (Ia)
1 2 3   4   5    6    7   8   9 10    11 12  13   14
A1-A2-A3-Cys-Tyr-A4-A5-A6-A7-A8-A9-A10-Cys-A11
```

In this formula:

A1 is an arginine, lysine, ornithine, citrulline, alanine or glutamic acid residue which may be derivatized at N-terminal, or A1 is deleted;

A2 represents an arginine or glutamic acid residue if A1 is an arginine, lysine, ornithine, citrulline, alanine or glutamic acid residue which may be derivatized at N-terminal, or A2 represents an arginine or glutamic acid residue which may be derivatized at N-terminal if A1 is deleted;

A3 represents an aromatic amino acid residue;

A4, A5 and A9 each independently represents an arginine, lysine, ornithine, citrulline, alanine or glutamic acid residue;

A6 represents a proline, glycine, ornithine, lysine, alanine, citrulline, arginine or glutamic acid residue;

A7 represents a proline, glycine, ornithine, lysine, alanine, citrulline or arginine residue;

A8 represents a tyrosine, phenylalanine, alanine, naphthylalanine, citrulline or glutamic acid residue;

A10 represents a citrulline, glutamic acid, arginine or lysine residue;

A11 represents an arginine, glutamic acid, lysine or citrulline residue which may be derivatized at C-terminal;

In the above formula, Cys represents a cysteine residue, Tyr represents a tyrosine residue, the cysteine residue of the 4-position or the 13-position can be the combination by disulfide bond, and the amino acid can be either L or D form.

The peptidic compounds of the present invention have potent CXCR4 antagonistic activity, and show therapeutic effects for cancers and chronic rheumatoid arthritis by inhibiting the interaction of CXCR4 and CXCL12/SDF-1.

BRIEF DESCRIPTION OF THE DRAWINGS

FIG. 5A displays the lungs of the control group (saline administration group).

FIG. 5B is the pictures of the lungs of 4Fbenzoyl-TN-14003 administration group.

FIG. 9A shows fluctuations in body weight [vertical axis: body weight gain (g) (mean value±standard margin of error, n=8), horizontal axis: post-booster days];

FIG. 9B shows fluctuations of the incidence of the disease [vertical axis: incidence (%) (n=8), horizontal axis: post-booster days];

FIG. 9C shows fluctuations of arthritis score [vertical axis: arthritis score (mean value±standard margin of error, n=8), horizontal axis: post-booster days];

FIG. 9D shows fluctuations of ankle thickness [vertical axis: ankle thickness (mm) (mean value±standard margin of error, n=8), horizontal axis: post-booster days]. □: normal mouse group, ■: drug non-administration (control) group, Δ: indomethacin administration group, ▲: ethotrexate administration group, ●: FK506 administration group;

FIG. 9E shows each drug's effect on hindlimb swelling 2 weeks after the booster [vertical axis: hindlimb weight (mg) (average amount±standard margin of error, n=8)]; and FIG. 9F shows each drug's effect on anti-bovine II collagen IgG2a antibody value 2 weeks after the booster [vertical axis: antibody value (A450) (mean value±standard margin of error, n=8)] [from the left, it shows normal mouse group, drug non-administration (control) group, indomethacin (IND) administration group, methotrexate (MTX) administration group, FK506 administration group]. ## is $P \leq 0.01$ (comparison with normal mice group; t-test), * and ** respectively show $P \leq 0.05$ and $P \leq 0.01$ (comparison with drug non-administration group; Dunnett's test).

FIG. 10A shows fluctuations of the body weight [vertical axis: body weight (g) (mean value±standard margin of error), horizontal axis: post-booster days], FIG. 10B shows fluctuations of the disease incidence [vertical axis: incidence (%), horizontal axis: post-booster days], FIG. 10C shows fluctuations of arthritis score [vertical axis: arthritis score (mean value±standard margin of error), horizontal axis: post-booster days], FIG. 10D shows the fluctuations of ankle thickness [vertical axis: ankle thickness (mm) (mean value±standard margin of error), horizontal axis: post-booster days]. □: normal mice group (n=8), ■: drug non-administration (control) group (n=12), △: 4Fbenzoyl-TN-14003 administration group (n=11), FIG. 10E shows the effects of 4Fbenzoyl-TN-14003 on hindlimb swelling 2 weeks after the booster [vertical axis: hindlimb weight (mg) (mean value±standard margin of error)], and FIG. 10F shows the effects of 4Fbenzoyl-TN-14003 on the anti-bovine II collagen IgG2a antibody value 2 weeks after the booster [vertical axis: antibody value (A450) (mean value±standard margin of error)]. From the left, it shows normal mouse group (n=8), drug non-administration (control) group (n=12), 4Fbenzoyl-TN-14003 administration group (n=11)]. ## shows $P \leq 0.01$ (comparison with normal mice group; t-test), and ** shows $P \leq 0.01$ (comparison with drug non-administration group; t-test).

BEST MODE FOR CARRYING OUT THE INVENTION

Figure 1:
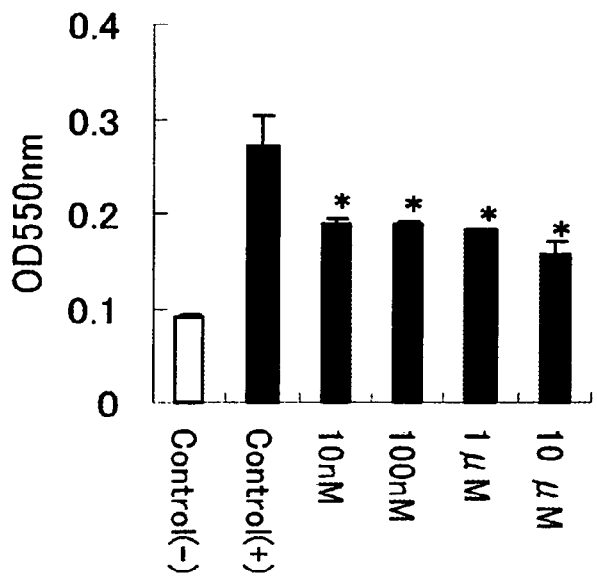
FIG. 1 shows the inhibitory activity of TE-14005 against the migration of breast cancer cells induced by CXCL12. The vertical axis shows the migration of cells (absorption of light: OD550 nm). From the left, it shows the result (mean value±standard deviation, n=2) obtained respectively when CXCL12 was not added (negative control), when CXCL12 was added (positive control), when CXCL12 and TE-14005 10 nM were added, when CXCL12 and TE-14005 100 nM were added, when CXCL12 and TE-14005 1 μM were added, and when CXCL12 and TE-14005 10 μM were added. * indicates the significance of each TE-14005 added group compared with the positive control group (Williams' test, $p \leq 0.025$).

The peptides described in this specification have N-terminal (amino-terminal) at the left extremity and C-terminal (carboxyl-terminal at the right extremity in accordance with the customary practice of peptide notations.

In this specification and drawings, the representations of amino acids, etc. by brevity codes are made by the use of the codes prescribed by IUPAC-IUB Commission on Biochemical Nomenclature or by the codes customarily used in the relevant art. Examples of such codes are shown as below. If an optical isomer exists with respect to an amino acid, it represents L form unless otherwise expressly specified.

Gly or G: glycine
Ala or A: alanine
Val or V: valine
Leu or L: leucine
Ile or I: isoleucine
Ser or S: serine
Thr or T: threonine
Cys or C: cysteine
Met or M: methionine
Glu or E: glutamic acid
Asp or D: aspartic acid
Lys or K: lysine
Arg or R: arginine
His or H: histidine
Phe or F: phenylalanine
Tyr or Y: tyrosine
Trp or W: tryptophan
Pro or P: proline
Asn or N: asparagine
Gln or Q: glutamine
pGlu: pyroglutamic acid
NaI: 3-(2-naphthyl) alanine
Cit: citrulline
DLys: D-lysine
DCit: D-citrulline
DGlu: D-glutamic acid
Me: methyl group
Et: ethyl group
Bu: butyl group
Ph: phenyl group The substituents, protective group and reagents often used in this specification are indicated by the following codes.

BHA: benzhydrylamine
pMBHA: p-methylbenzhydrylamine
Tos: p-toluenesulphonyl
CHO: formyl
HONB: N-hydroxy-5-norbornene-2,3-dicarboximide
OcHex: cyclohexyl ester
Bzl: benzyl
C12-Bzl: dichloro-benzyl
Bom: benzyloxymethyl
Z: benzyloxycarbonyl
Br—Z: 2-bromobenzyloxycarbonyl
Boc: t-butyloxycarbonyl
DCM: dichloromethane
HOBt: 1-hydroxybenzotriazole
DCC: N,N'-dicyclohexylcarbodiimide
TFA: trifluoroacetic acid
DIEA: diisopropylethylamine
Fmoc: N-9-fluorenylmethoxycarbony
DNP: dinitrophenyl
Bum: tertiarybutoxymethyl
Trt: trityl
Ac: acetyl
Guanyl: guanyl
Succinyl: succinyl
glutaryl: glutaryl
TMguanyl: tetramethylguanyl
2F-benzoyl: 2-fluorobenzoyl
4F-benzoyl: 4-fluorobenzoyl
APA: 5-aminopentanoyl
ACA: 6-aminohexanoyl
desamino-Arg: 2-desamino-arginyl
deamino TMG-APA: the following formula (II)

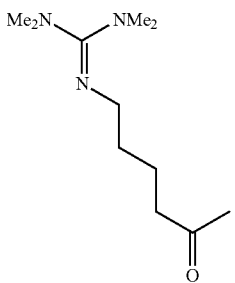

nelfinaviryl-succinyl: the following formula (III)

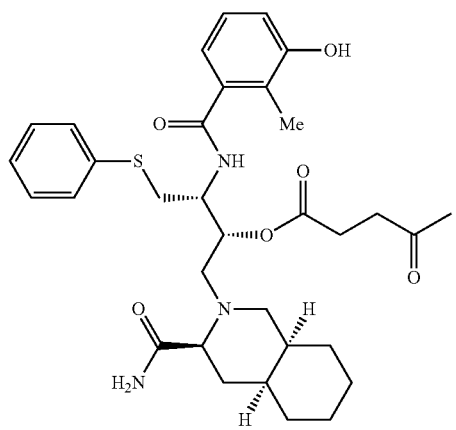

AZT-glutaryl: the following formula (IV)

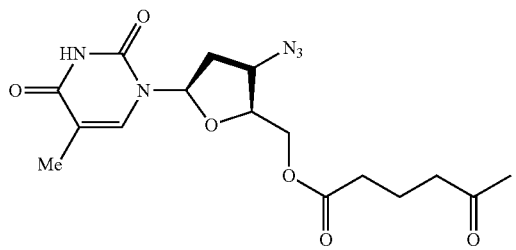

R—CH2: the following formula (V)

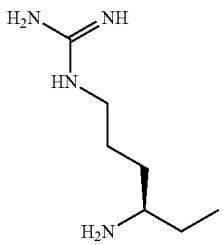

In amino acids of N-terminal peptide, [H—] indicates that terminalamino group is not derivatized, and in amino acids of C-terminal peptide, [—OH] indicates that terminal carboxyl group is not derivatized.

The present invention provides preventive and/or therapeutic medicines containing CXCR4 antagonistic compounds for cancers and chronic rheumatoid arthritis. The "CXCR4 antagonistic compounds" show anti-cancer activity antagonistically inhibiting the interaction of CXCR4 and its physiological ligand CXCL12/SDF-1α (e.g. migration inhibitory activity, invasion inhibitory activity, and anti-metastasis activity, etc.) or anti-chronic rheumatoid arthritis activity (e.g. migration inhibitory activity), and more particularly, they include the peptide represented by the following formula (Ia), an amide thereof, an ester thereof or a salt thereof (hereinafter as may be collectively referred to as "peptide(s) of the present invention"):

(Ia)
```
 1  2  3   4   5   6   7  8  9 10   11 12  13  14
A1-A2-A3-Cys-Tyr-A4-A5-A6-A7-A8-A9-A10-Cys-A11
```

In this formula:

A1 is an arginine, lysine, ornithine, citrulline, alanine or glutamic acid residue which may be derivatized at N-terminal, or A1 is deleted;

A2 represents an arginine or glutamic acid residue if A1 is an arginine, lysine, ornithine, citrulline, alanine or glutamic acid residue which may be derivatized at N-terminal, or A2 represents an arginine or glutamic acid residue which may be derivatized at N-terminal if A1 is deleted;

A3 represents an aromatic amino acid residue;

A4, A5 and A9 each independently represents an arginine, lysine, ornithine, citrulline, alanine or glutamic acid residue;

A6 represents a proline, glycine, ornithine, lysine, alanine, citrulline, arginine or glutamic acid residue;

A7 represents a proline, glycine, ornithine, lysine, alanine, citrulline or arginine residue;

A8 represents a tyrosine, phenylalanine, alanine, naphthylalanine, citrulline or glutamic acid residue;

A10 represents a citrulline, glutamic acid, arginine or lysine residue;

A11 represents an arginine, glutamic acid, lysine or citrulline residue which may be derivatized at C-terminal;

In the above formula, Cys represents a cysteine residue, Tyr represents a tyrosine residue, the cysteine residue of the 4-position or the 13-position can be the combination by disulfide bond, and the amino acid can be either L or D form.

A1 in the above-mentioned formula (Ia) represents an arginine, lysine, ornithine, citrulline, alanine or glutamic acid residue (either L or D form) which may be derivatized at N-terminal, or A1 is deleted, or it is preferable that A1 is an arginine, citrulline, alanine or D-glutamic acid residue, or A1 is deleted.

Examples of "peptides derivatized at N-terminal" include, but are not limited to, those protected by formyl group; acyl group, e.g., acetyl group, propionyl group, butyryl group, pentanoyl group, C2-6alkanoyl group such as hexanoyl group, benzoyl group, arylcarbonyl group such as substituted benzoyl group (e.g.: 2-fluorobenzoyl, 3-fluorobenzoyl group, 4-fluorobenzoyl group, 2-bromobenzoyl group, 3-bromobenzoyl group, 4-bromobenzoyl group, 2-nitrobenzoyl group, 3-nitrobezoyl group, 4-nirtobenzoyl group), succinyl group, glutaryl group; nicotinyl group; isonicotinyl group; alkylsulfonyl group (e.g.: methanesulfonyl group, ethanesulfonyl group, propanesulfonyl group, camphorsulfonyl group); arylsulfonyl group (e.g.: p-toluenesulfonyl group, 4-fluorobenzenesulfonyl group, mesitylenesulfonyl group, 4-aminobenzenesulfonyl group, dansyl group, 4-bromobenzenesulfonyl group) etc. Or, the amino acid group of N-terminal may be deleted.

A2 in the above-mentioned formula (Ia) represents an arginine or glutamic acid residue (either L or D form) if A1 is an arginine, lysine, ornithine, citrulline, alanine or glutamic acid residue (either L or D form) which may be derivatized at N-terminal, or A2 represents an arginine or glutamic acid residue (either L or D form) which may be derivatized at N-terminal if A1 is deleted, or it is preferable that A2 is an arginine or glutamic acid residue if A1 is an arginine, citrulline, alanine or glutamic acid residue which may be derivatized at N-terminal, or A2 is an arginine or glutamic acid residue which may be derivatized at N-terminal if A1 is deleted.

Examples of "peptides derivatized at N-terminal" include, but are not limited to, the same ones as those mentioned in A1.

A3 in the above-mentioned formula (Ia) represents an aromatic amino acid residue (e.g., phenylalanine, tryptophan, 3-(2-naphthyl)alanine, tyrosine, 4-fluorophenylalanine, 3-(1-naphthyl)alanine (either L or D form), or preferably, A3 represents phenylalanine, tryptophan or 3-(2-naphthyl)alanine.

A4 in the above-mentioned formula (Ia) represents an arginine, lysine, ornithine, citrulline, alanine or glutamic acid residue (either L or D form), or it is preferable that A4 is an arginine, citrulline, alanine or L- or D-glutamic acid residue.

A5 in the above-mentioned formula (Ia) represents an arginine, lysine, ornithine, citrulline, alanine or glutamic acid residue, or it is preferable that A5 is an arginine, citrulline, alanine, lysine or glutamic acid residue.

A6 in the above-mentioned formula (Ia) represents a proline, glycine, ornithine, lysine, alanine, citrulline, arginine or glutamic acid residue (either L or D form), or it is preferable that A6 is a D-lysine, D-alanine, D-citrulline or D-glutamic acid residue.

A7 in the above-mentioned formula (Ia) represents a proline, glycine, ornithine, lysine, alanine, citrulline or arginine residue (either L or D form), or it is preferable that A7 is a proline or alanine residue.

A8 in the above-mentioned formula (Ia) represents a tyrosine, phenylalanine, alanine, naphthylalanine, citrulline or glutamic acid residue (either L or D form), or it is preferable that A8 is a tyrosine, alanine or D-glutamic acid residue.

A9 in the above-mentioned formula (Ia) represents an arginine, lysine, ornithine, citrulline, alanine or glutamic acid residue (either L or D form), or it is preferable that A9 is an arginine, citrulline or glutamic acid residue.

A10 in the above-mentioned formula (Ia) represents a citrulline, glutamic acid, arginine or lysine residue (either L or D form), or it is preferable that A10 is a citrulline or D-glutamic acid residue.

A11 in the above-mentioned formula (Ia) represents an arginine, glutamic acid, lysine or citrulline residue (either L or D form) which may be derivatized at C-terminal, or it is preferable that A11 is an arginine or glutamic acid residue which may be derivatized at C-terminal.

"Derivatization at C-terminal" includes, without limitation, amidation (—$CONH_2$, —CONHR, —CONRR') and esterification (—COOR). Herein, R and R' in amides and esters include, for example, C1-6 alkyl group such as methyl, ethyl, n-propyl, isopropyl, or n-butyl, C3-8 cycloalkyl group such as cyclopentyl, cyclohexyl, C6-12 aryl group such as phenyl and α-naphthyl, phenyl-C1-2 alkyl group such as benzyl, phenethyl or C7-14 aralkyl group such as C1-2 alkyl group such as α-naphthyl methyl group, and additionally, pivaloyloxymethyl group which is generally used as an oral bioavailable ester.

If a peptide of the present invention has carboxy groups (or carboxylates) at side-chain terminals other than C-terminal, the peptide having amidated or esterificated carboxy groups at side-chain terminals is included in the peptides of the present invention. As the amides and esters in this case, for example, the amides and esters exemplified in A11 are similarly used. Also, the peptides of the present invention include peptides in which substituents (e.g.—OH, —SH, amino group, imidazole group, indole group, guanidino group, etc.) on the intramolecular amino acid side chains are protected by suitable protective group (e.g. C1-6 acyl group, C2-6 alkanoyl such as formyl group, acetyl group, etc.), or complex peptides such as glycopeptides combined with sugar chain in the above-mentioned peptides.

Salts of the peptides of the present invention include physiologically acceptable salts of acids or bases and particularly, physiologically acceptable acid addition salts are preferable. Such salts are exemplified by salts of inorganic acids (e.g. hydrochloric acid, phosphoric acid, hydrobromic acid, sulfuric acid), or salts of organic acids (e.g. acetic acid, formic acid, propionic acid, fumaric acid, maleic acid, succinic acid, tartaric acid, citric acid, malic acid, oxalic acid, benzoic acid, methanesulfonic acid, benzenesulfonic acid).

A peptide of the present invention is a new peptide if any one of A1 to A11 indicated in the above-mentioned formula (Ia) is the following:

(i) If A1 is a glutamic acid residue or is deleted (i.e. the same as the above-mentioned formula (Ib));

(ii) If any one of A2, A4, A6, A8 and A9 is a glutamic acid residue (i.e. the same as any of the above-mentioned formula (Ic) to (Ig)):

(iii) If A5 is an arginine or glutamic acid residue (i.e. the same as the above-mentioned formula (Ih)):

(iv) If A10 is a glutamic acid, arginine or lysine residue (i.e. the same as the above-mentioned formula (II)):

(v) If A11 is a glutamic acid, lysine or citrulline residue (i.e. the same as the above-mentioned formula (ID).

The above-mentioned amino acid residues may be either L or D form.

As the peptides of the present invention, preferably the peptides having the amino acid sequences of the following (1) to (58) (in each sequence, two cysteine residues are coupled by the disulfide bond) are exemplified.

[SEQ ID NO: 11]
(1) Ac-Arg-Arg-Nal-Cys-Tyr-Cit-Lys-DLys-Pro-Tyr-Arg-Cit-Cys-Arg-OH (AcTC14003)

[SEQ ID NO: 12]
(2) Ac-Arg-Arg-Nal-Cys-Tyr-Arg-Lys-DCit-Pro-Tyr-Arg-Cit-Cys-Arg-OH (AcTC14005)

[SEQ ID NO: 13]
(3) Ac-Arg-Arg-Nal-Cys-Tyr-Cit-Lys-DCit-Pro-Tyr-Arg-Cit-Cys-Arg-OH (AcTC14011)

[SEQ ID NO: 14]
(4) Ac-Arg-Arg-Nal-Cys-Tyr-Cit-Lys-DLys-Pro-Tyr-Cit-Cit-Cys-Arg-OH (AcTC14013)

[SEQ ID NO: 15]
(5) Ac-Cit-Arg-Nal-Cys-Tyr-Cit-Lys-DLys-Pro-Tyr-Arg-Cit-Cys-Arg-OH (AcTC14015)

[SEQ ID NO: 16]
(6) Ac-Cit-Arg-Nal-Cys-Tyr-Arg-Lys-DCit-Pro-Tyr-Arg-Cit-Cys-Arg-OH (AcTC14017)

-continued

[SEQ ID NO: 17]
(7) Ac-Arg-Arg-Nal-Cys-Tyr-Arg-Lys-DCit-Pro-Tyr-Cit-Cit-Cys-Arg-OH (AcTC14019)

[SEQ ID NO: 18]
(8) Ac-Cit-Arg-Nal-Cys-Tyr-Arg-Lys-DLys-Pro-Tyr-Cit-Cit-Cys-Arg-OH (AcTC14021)

[SEQ ID NO: 19]
(9) Ac-Arg-Arg-Nal-Cys-Tyr-Cit-Lys-DCit-Pro-Tyr-Arg-Cit-Cys-Arg-NH$_2$ (AcTC14012)

[SEQ ID NO: 20]
(10) Ac-Arg-Arg-Nal-Cys-Tyr-Cit-Lys-DLys-Pro-Tyr-Cit-Cit-Cys-Arg-NH$_2$ (AcTC14014)

[SEQ ID NO: 21]
(11) Ac-Cit-Arg-Nal-Cys-Tyr-Cit-Lys-DLys-Pro-Tyr-Arg-Cit-Cys-Arg-NH$_2$ (AcTC14016)

[SEQ ID NO: 22]
(12) Ac-Cit-Arg-Nal-Cys-Tyr-Arg-Lys-DCit-Pro-Tyr-Arg-Cit-Cys-Arg-NH$_2$ (AcTC14018)

[SEQ ID NO: 23]
(13) Ac-Arg-Arg-Nal-Cys-Tyr-Arg-Lys-DCit-Pro-Tyr-Cit-Cit-Cys-Arg-NH$_2$ (AcTC14020)

[SEQ ID NO: 24]
(14) Ac-Cit-Arg-Nal-Cys-Tyr-Arg-Lys-DLys-Pro-Tyr-Cit-Cit-Cys-Arg-NH$_2$ (AcTC14022)

[SEQ ID NO: 25]
(15) H-DGlu-Arg-Nal-Cys-Tyr-Arg-Lys-DLys-Pro-Tyr-Arg-Cit-Cys-Arg-OH (TE14001)

[SEQ ID NO: 26]
(16) H-Arg-Glu-Nal-Cys-Tyr-Arg-Lys-DLys-Pro-Tyr-Arg-Cit-Cys-Arg-OH (TE14002)

[SEQ ID NO: 27]
(17) H-Arg-Arg-Nal-Cys-Tyr-Glu-Lys-DLys-Pro-Tyr-Arg-Cit-Cys-Arg-OH (TE14003)

[SEQ ID NO: 28]
(18) H-Arg-Arg-Nal-Cys-Tyr-Arg-Glu-DLys-Pro-Tyr-Arg-Cit-Cys-Arg-OH (TE14004)

[SEQ ID NO: 29]
(19) H-Arg-Arg-Nal-Cys-Tyr-Arg-Lys-DGlu-Pro-Tyr-Arg-Cit-Cys-Arg-OH (TE14005)

[SEQ ID NO: 30]
(20) H-Arg-Arg-Nal-Cys-Tyr-Arg-Lys-DLys-Pro-Tyr-Glu-Cit-Cys-Arg-OH (TE14006)

[SEQ ID NO: 31]
(21) H-Arg-Arg-Nal-Cys-Tyr-Arg-Lys-DLys-Pro-Tyr-Arg-Cit-Cys-Glu-OH (TE14007)

[SEQ ID NO: 32]
(22) H-Arg-Arg-Nal-Cys-Tyr-Cit-Lys-DGlu-Pro-Tyr-Arg-Cit-Cys-Arg-NH$_2$ (TE14011)

[SEQ ID NO: 33]
(23) H-Arg-Arg-Nal-Cys-Tyr-DGlu-Lys-DCit-Pro-Tyr-Arg-Cit-Cys-Arg-NH$_2$ (TE14012)

[SEQ ID NO: 34]
(24) H-Arg-Arg-Nal-Cys-Tyr-DGlu-Lys-DGlu-Pro-Tyr-Arg-Cit-Cys-Arg-NH$_2$ (TE14013)

[SEQ ID NO: 35]
(25) H-DGlu-Arg-Nal-Cys-Tyr-Cit-Lys-DGlu-Pro-Tyr-Arg-Cit-Cys-Arg-NH$_2$ (TE14014)

[SEQ ID NO: 36]
(26) H-Arg-Arg-Nal-Cys-Tyr-Cit-Lys-DGlu-Pro-DGlu-Arg-Cit-Cys-Arg-NH$_2$ (TE14015)

[SEQ ID NO: 37]
(27) H-Arg-Arg-Nal-Cys-Tyr-Cit-Lys-DGlu-Pro-Tyr-Arg-DGlu-Cys-Arg-NH$_2$ (TE14016)

[SEQ ID NO: 38]
(28) Ac-DGlu-Arg-Nal-Cys-Tyr-Cit-Lys-DGlu-Pro-Tyr-Arg-Cit-Cys-Arg-NH$_2$ (AcTE14014)

[SEQ ID NO: 39]
(29) Ac-Arg-Arg-Nal-Cys-Tyr-Cit-Lys-DGlu-Pro-DGlu-Arg-Cit-Cys-Arg-NH$_2$ (AcTE14015)

[SEQ ID NO: 40]
(30) Ac-Arg-Arg-Nal-Cys-Tyr-Cit-Lys-DGlu-Pro-Tyr-Arg-DGlu-Cys-Arg-NH$_2$ (AcTE14016)

[SEQ ID NO: 41]
(31) Ac-Arg-Arg-Nal-Cys-Tyr-Cit-Lys-DGlu-Pro-Tyr-Arg-Cit-Cys-Arg-NH$_2$ (TF1: AcTE14011)

[SEQ ID NO: 42]
(32) guanyl-Arg-Arg-Nal-Cys-Tyr-Cit-Lys-DGlu-Pro-Tyr-Arg-Cit-Cys-Arg-NH$_2$ (TF2: guanyl-TE14011)

[SEQ ID NO: 43]
(33) TMguanyl-Arg-Arg-Nal-Cys-Tyr-Cit-Lys-DGlu-Pro-Tyr-Arg-Cit-Cys-Arg-NH$_2$ (TF3: TMguanyl-TE14011)

[SEQ ID NO: 44]
(34) TMguanyl-Nal-Cys-Tyr-Cit-Lys-DGlu-Pro-Tyr-Arg-Cit-Cys-Arg-NH$_2$ (TF4: TMguanyl-TE14011 (2-14))

[SEQ ID NO: 45]
(35) 4F-benzoyl-Arg-Arg-Nal-Cys-Tyr-Cit-Lys-DGlu-Pro-Tyr-Arg-Cit-Cys-Arg-NH$_2$ (TF5: 4F-benzoyl-TE14011)

[SEQ ID NO: 46]
(36) 2F-benzoyl-Arg-Arg-Nal-Cys-Tyr-Cit-Lys-DGlu-Pro-Tyr-Arg-Cit-Cys-Arg-NH$_2$ (TF6: 2F-benzoyl-TE14011)

[SEQ ID NO: 47]
(37) APA-Arg-Nal-Cys-Tyr-Cit-Lys-DGlu-Pro-Tyr-Arg-Cit-Cys-Arg-NH$_2$ (TF7: APA-TE14011 (2-14))

[SEQ ID NO: 48]
(38) desamino-R-Arg-Nal-Cys-Tyr-Cit-Lys-DGlu-Pro-Tyr-Arg-Cit-Cys-Arg-NH$_2$ (TF8: desamino-R-TE14011 (2-14))

[SEQ ID NO: 49]
(39) guanyl-Arg-Nal-Cys-Tyr-Cit-Lys-DGlu-Pro-Tyr-Arg-Cit-Cys-Arg-NH$_2$ (TF9: guanyl-TE14011 (2-14))

[SEQ ID NO: 50]
(40) succinyl-Arg-Nal-Cys-Tyr-Cit-Lys-DGlu-Pro-Tyr-Arg-Cit-Cys-Arg-NH$_2$ (TF10: succinyl-TE14011 (2-14))

[SEQ ID NO: 51]
(41) glutaryl-Arg-Nal-Cys-Tyr-Cit-Lys-DGlu-Pro-Tyr-Arg-Cit-Cys-Arg-NH$_2$ (TF11: glutaryl-TE14011 (2-14))

[SEQ ID NO: 52]
(42) deaminoTMG-APA-Arg-Nal-Cys-Tyr-Cit-Lys-DGlu-Pro-Tyr-Arg-Cit-Cys-Arg-NH$_2$ (TF12: deaminoTMG-APA-TE14011 (2-14))

[SEQ ID NO: 53]
(43) nelfinaviryl-succinyl-Arg-Nal-Cys-Tyr-Cit-Lys-DGlu-Pro-Tyr-Arg-Cit-Cys-Arg-NH$_2$ (TF13: nelfinaviryl-succinyl-TE14011 (2-14))

[SEQ ID NO: 54]
(44) AZT-glutaryl-Arg-Nal-Cys-Tyr-Cit-Lys-DGlu-Pro-Tyr-Arg-Cit-Cys-Arg-NH$_2$ (TF14: AZT-glutaryl-TE14011 (2-14))

[SEQ ID NO: 55]
(45) R-CH2-Arg-Nal-Cys-Tyr-Cit-Lys-DGlu-Pro-Tyr-Arg-Cit-Cys-Arg-NH$_2$ (TF15: H-Arg-CH2NH-RTE14011 (2-14))

[SEQ ID NO: 56]
(46) H-Arg-Nal-Cys-Tyr-Cit-Lys-DGlu-Pro-Tyr-Arg-Cit-Cys-Arg-NH$_2$ (TF17: TE14011 (2-14))

[SEQ ID NO: 57]
(47) TMguanyl-Arg-Arg-Nal-Cys-Tyr-Cit-Lys-DCit-Pro-Tyr-Arg-Cit-Cys-Arg-NH$_2$ (TF18: TMguanyl-TC14012)

[SEQ ID NO: 58]
(48) ACA-Arg-Arg-Nal-Cys-Tyr-Cit-Lys-DCit-Pro-Tyr-Arg-Cit-Cys-Arg-NH$_2$ (TF19: ACA-TC14012)

[SEQ ID NO: 59]
(49) ACA-Arg-Arg-Nal-Cys-Tyr-Arg-Lys-DLys-Pro-Tyr-Arg-Cit-Cys-Arg-OH (TF20: ACA-T140)

[SEQ ID NO: 60]
(50) H-Arg-Arg-Nal-Cys-Tyr-Cit-Arg-DLys-Pro-Tyr-Arg-Cit-Cys-Arg-NH$_2$ (TZ14011)

[SEQ ID NO: 61]
(51) Ac-Arg-Arg-Nal-Cys-Tyr-Cit-Arg-DLys-Pro-Tyr-Arg-Cit-Cys-Arg-NH$_2$ (AcTZ14011)

[SEQ ID NO: 62]
(52) Ac-Arg-Arg-Nal-Cys-Tyr-Cit-Lys-DLys-Pro-Tyr-Arg-Cit-Cys-Arg-NH$_2$ (AcTN14003)

[SEQ ID NO: 63]
(53) Ac-Arg-Arg-Nal-Cys-Tyr-Arg-Lys-DCit-Pro-Tyr-Arg-Cit-Cys-Arg-NH$_2$ (AcTN14005)

[SEQ ID NO: 64]
(54) 4F-benzoyl-Arg-Arg-Nal-Cys-Tyr-Cit-Lys-DLys-Pro-Tyr-Arg-Cit-Cys-Arg-NH$_2$ (4F-benzoyl-TN14003)

[SEQ ID NO: 65]
(55) 4F-benzoyl-Arg-Arg-Nal-Cys-Tyr-Cit-Lys-DGlu-Pro-Tyr-Arg-Cit-Cys-Arg-NHMe (4F-benzoyl-TN14011-Me)

[SEQ ID NO: 66]
(56) 4F-benzoyl-Arg-Arg-Nal-Cys-Tyr-Cit-Lys-DGlu-Pro-Tyr-Arg-Cit-Cys-Arg-NHEt (4F-benzoyl-TN14011-Et)

[SEQ ID NO: 67]
(57) 4F-benzoyl-Arg-Arg-Nal-Cys-Tyr-Cit-Lys-DGlu-Pro-Tyr-Arg-Cit-Cys-Arg-NHiPr (4F-benzoyl-TN14011-iPr)

[SEQ ID NO: 68]
(58) 4F-benzoyl-Arg-Arg-Nal-Cys-Tyr-Cit-Lys-DGlu-Pro-Tyr-Arg-Cit-Cys-Arg-tyramine (4F-benzoyl-TN14011-tyramine)

A peptide of the present invention includes a peptide or its amide, ester or salt containing the amino acid sequence which is the substantially same amino acid sequence as the sequence of any of the above-mentioned peptides. Here, "the substantially same amino acid sequence" means the amino acid sequence qualitatively identical in the activity of the peptide (e.g. the inhibitory activity on the interaction of a ligand and a receptor) or the anti-cancer activity of the peptide (e.g. migration inhibitory activity, invasion inhibitory activity and anti-metastasis activity) or the anti-rheumatoid arthritis activity (e.g. migration inhibitory activity) or the like. Accordingly, quantitative variances are acceptable to some extent (e.g. about 0.01 to 100 times, preferably 0.5 to 20 times, or more preferably 0.5 to 2 times). Therefore, one or more of the amino acids in the amino acid sequences indicated in any of the above-mentioned formula (Ia) to (Ij) and (1) to (58) can have variances, so far as they have any of the above-mentioned properties. That is to say, in the present invention, any peptide (variant peptide) resulting from the variance in the amino acid sequence such as substitution, deletion or insertion (addition) etc. which brings about any serious (significant) change (i.e. a qualitatively different change, or a qualitatively identical but quantitatively significantly different change) in the physiological property or chemical property of the original (non-variant) peptide is deemed as substantially same as the original (non-variant) peptide having no such variance, and, the amino acid sequence of such variant peptide is deemed as substantially same as the amino acid sequence of the original (non-variant) peptide.

It is a well-known fact that generally, the change such as substitution, deletion or insertion (addition) of an amino acid in a peptide sequence often does not make a great (notable) change to physiological property or chemical property of such peptide. Such substitution is exemplified by the substitution of a certain amino acid by another amino acid of similar nature (property), and generally, it is considered that if the substitution is made between amino acids having greater similarity in their properties, so much smaller the changes caused by such substitution is in the properties of pre-substituted peptides.

Amino acids are classified, using the similarity of their properties as to one of the criteria, into the following classes, for example: (i) nonpolar (hydrophobic) amino acids (examples: alanine, leucine, isoleucine, valine, proline, phenylalanine, tryptophan, methionine, etc.); (ii) polar (neutral) amino acids (examples: glycine, serine, threonine, cysteine, tyrosine, asparagine, glutamine, etc.); (iii) (basic) amino acids carrying positive electric charge (examples: arginine, lysine, histidine, etc.); (iv)) (acidic) amino acids carrying negative electric charge (examples: asparatic acid, glutamic acid, etc.), and accordingly, amino acid substitution within each class can be conservative with regard to the property of a peptide (namely, substitution generating "substantially same" amino acid sequences).

In other words, "substantially same amino acid sequences" may include:

(i) amino acid sequences wherein 1 or more, preferably 1 to 10, more preferably 1 to 5 amino acids were substituted by other amino acids in the amino acid sequences indicated in the above-mentioned formula (Ia) to (Ij) and (1) to (58);

(ii) amino acid sequences wherein 1 to 7, preferably 1 to 5, more preferably 1 to 3 amino acids were deleted in the amino acid sequences indicated in the above-mentioned formula (Ia) to (Ij) and (1) to (58);

(iii) amino acid sequences wherein 1 to 15, preferably 1 to 10, more preferably 1 to 5 amino acids were added (inserted) in the amino acid sequences indicated in the above-mentioned formula (Ia) to (Ij) and (1) to (58); or (iv) peptides including modifications to constitutive amino acids (particularly, the side chains thereof) among the peptides having the amino acid sequences indicated in above (i), (ii) or (iii), or esters thereof or salts thereof.

A peptide of the present invention, if and when the substitution, deletion, insertion (addition), modification, etc. of above (i) to (iv) is intentionally or incidentally provided in the amino acid sequence thereof, can be varied to a stable peptide against heat or protease or a high-activity peptide having more enhanced inhibitory activity. The peptides of the present invention include also these variant peptides or amides thereof, esters thereof or salts thereof.

Furthermore, among the peptides of the present invention are the peptide consisting of the amino acid sequence indicated in any of the above-mentioned formula (Ia to Ij) and (1) to (58), and the peptide containing the amino acid sequence sharing the homology of about 50 to 99.9% (preferably, 70 to 99.9%, more preferably 90 to 99.9%) with the foregoing amino acid sequence and having the activities of substantially same nature as the peptide consisting of the amino acid sequence indicated in any of the above-mentioned formula (Ia to Ij) and (1) to (58), or amides thereof, esters thereof or salts thereof. Such activities include, for example, inhibitory activities of the peptides such as an inhibitory activity on the binding of a ligand to its receptor, a signaling inhibitory activity. The inhibitory activities of "substantially same nature" mean that the properties such as the inhibitory activity on the ligand binding to the receptor are of the same nature. Therefore, it is acceptable even if non-significant effectiveness levels of the inhibitory activity on the ligand binding to the receptor are found, and it is not matter even if there are differences in molecular weights.

The amides, esters or salts of the peptide having the amino acid sequence indicated in any of the above-mentioned formula (1) to (58) include the same ones as are exemplified for the peptide indicated in the above-mentioned formula (Ia). Preferably, the peptide having the amino acid sequence indicated in any of the above-mentioned formula (1) to (58) is better if the carboxyl group of the C-terminal amino acid residue is amidated.

The peptides of the present invention including the peptide containing the amino acid sequence indicated in any of the above-mentioned formula (1) to (58) can be produced by conventionally known methods of synthesizing peptides. For the syntheses of peptides, either solid phase peptide synthesis or liquid phase synthesis may be utilized. Namely, an expected peptide can be produced by condensing a partial peptide able to constitute a peptide or an amino acid with remaining portions, and if the product has a protecting group, by eliminating the protecting group. As the known condensation methods and elimination of protecting groups, the following examples (1) to (5) are included:

(1) M. Bodanszky and M. A. Ondetti, Peptide Synthesis, Interscience Publishers, New York (1966).

(2) Schroeder and Luebke, The Peptide, Academic Press, New York (1965).

(3) N. Izumiya, et. al., Peptide Synthesis, Basics and Practice, Maruzen, Tokyo (1975).

(4) H. Yajima and S. Sakakibara, Seikagaku-Jikken-Koza I, Protein Chemistry IV, Tokyo Kagakudojin, Tokyo, pp 205 (1977).

(5) H. Yajima, Zoku-Iyakuhin-no-Kaihatsu, Vol. 14, Peptide Synthesis, Hirokawa Publishing Co., Tokyo (1991).

As practical methods for syntheses of peptides, the following examples can be given: Generally, commercially available resins for synthesis of polypeptides can be used. Such resins include, for example, chloromethyl resin, hydroxymethyl resin, benzhydroxylamine resin, aminomethyl resin, 4-hydroxybenzylalcohol resin, 4-methylbenzhydroxylamine resin, PAM resin, 4-hydroxymethylmethylphenylacetoamidomethyl resin, polyacrylamide resin, 4-(2',4'-dimetoxyphenyl-hydroxymethyl)phenoxy resin, 4-2',4'-dimetoxyphenyl-Fmoc aminoethylphenoxy resin, etc. Using such resin, an amino acid with suitably protected α-amino group and side chain functional group is condensed on the resin to the sequence of the expected polypeptide in accordance with conventionally known condensation methods. In the last stage of the reaction, the polypeptide is cleared from the resin and simultaneously various protective groups are removed, and then, by carrying out intramolecular disulfide bond-forming reaction in highly diluted solution, the expected polypeptide or amide thereof is obtained. For the above-mentioned condensation of the protected amino acid, various activated reagents usable for the syntheses of polypeptides can be used, but, it is particularly better to use carboxylmides. Among such carboxylmides are DCC, N,N'-diisopropylcarbodiimide, N-ethyl-N'-(3-dimethylaminopropyl)cabodiimde, etc. For the activation by these, together with racemization inhibitory additives (for example, HOBt, HOOBt), a protected amino acid is added directly to the resin, or after activating the protected amino acid as symmetric acid anhydride or HOBt ester or HOOBt ester, it can be added to ester resin.

Solvents used for the activation of protected amino acids and the condensation with resins can be chosen from among the solvents known to be usable for polypeptide condensation reactions. For example, acid amides such as N,N-dimethylformamide, N,N-dimethylacetoamide and N-methylpyrrolidone, halogenated hydrocarbons such as methylene chloride and chloroform, alcohols such as trifluoroethanol, sulfoxides such as methyl sulfoxide, ethers such as pyridine, dioxane and tetrahydrofuran, nitriles such as acetonitrile and propionitrile, esters such as methyl acetate and ethyl acetate, or appropriated mixtures of the foregoings are used. A solvent used for activation of a protected amino acid or its condensation with resin can be selected from among the solvents known to be usable for condensing reactions of polypeptides. The reaction temperature is appropriately set within the scope known to be applicable to polypeptide bond forming reactions, usually, at −20° C. to 50° C. Activated amino acid derivatives are usually used at 1.5 to 4 times excess. According to the result of tests adopting ninhydrin reaction, if the condensation is insufficient, the repetition of condensation reactions without eliminating protective groups can lead to sufficient condensation. If sufficient condensation is attained by the repetition of reactions, unreacted amino acids can be acetylated by the use of acetic anhydride or acetylimidazole.

The protective group of the amino group used as ingredients include, for example, Z, Boc, tertialypentyloxycarbony, isobornyloxycarbonyl, 4-methoxybenzyloxycabonyl, Cl—Z, Br—Z, adamantyloxycabonyl, trifluoroacetyl, phtaloyl, formyl, 2-nitrophenylsulphenyl, diphenylphosphinothioyl, Fmoc, etc. Carboxyl group can be protected, for example, by alkyl esterification (e.g. straight-chain, branching or circular alkyl esterification of methyl, ethyl, propyl, butyl, tertialbutyl, cyclopentyl, cyclohexyl, cycloheptyl, cyclooctyl, 2-adamantyl, etc.), aralkyl esterification (e.g. benzylester, 4-nitrobenzylester, 4-methoxybenzylester, 4-chlorb enzylester, benzhydryl esterification), phenacylesterification, benzylcarbonylhydrazidation, tertialybutoxycarbonylhydrazidation, tritylhydrazidation, etc. The hydroxyl group of serine can be protected, for example, by esterification or etherification. The groups suitable for this eterification include, for example, groups derivatized from carboxylic acid such as lower alkanoyl group such as acetyl group, aroyl group such as benzoyl group, benzyloxycarbonyl group, ethoxycarbonyl group. The groups suitable for etherification include, for example, benzyl group, tetrahydropiranyl group, tertiarybutyl group, etc. As the protective groups of phenolic OH group of tyrosine, for example, Bzl, Cl2-Bzl, 2-nitrobenzyl, Br—Z, tertiarlybutyl, etc. are used. As the protective groups of imidazole of histidine, for example, Tos, 4-methoxy-2,3,6-trimethylbenzenesulfonyl, DNP, benzyloxymethyl, Bum, Boc, Trt, Fmoc etc. are used.

Ingredients with activated carboxyl groups include, for example, corresponding acid anhydride, azide, active ester [ester of alcohol (e.g. pentachlorophenol, 2,4,5-trichlorophenol, 2,4-dinitrophenol, cyanomethylalcohol, p-nitrophenol, HONB, N-hydroxysuccimide, N-hydroxyphtalimide, HOBO] are used. Ingredients with activated amino group include, for example, corresponding phosphoric amide. As the methods to remove (elimiate) protective groups, for example, catalytic reduction in hydrogen airstream in the presence of a catalyst such as Pd-black or Pd-carbon, acid treatment by anhydrous hydrogen fluoride, methanesulfonic acid, trifluoromethanesulfonic acid, trifluoroacetic acid or a mixture thereof, etc, base treatment by diisopropylethylamine, triethylamine, piperidine, piperadine, etc., and reduction by natrium in liquid ammonia are used. Elimination reaction by the above-mentioned acid treatment is done generally at the temperature of about −20° C. to 40° C., but in the acid treatment, it is effective to add a cation trapping agent such as anisole, phenol, thioanisole, m-cresol, p-cresol, dimethylsulfide, 1,4-butanedithiol, 1,2-ethanedithiol. 2,4-dinitrophenyl group used as the protective group of imidazole of histidine is removed by thiophenol treatment. Formyl group used as the protective group of indole of tryptophan is removed by elimination of protection by the above-mentioned acid treatment in the presence of 1,2-ethanedithiol, 1,4-butanedithiol, etc. and also is removed by alkaline treatment by dilute sodium hydroxide solution, dilute ammonia, etc.

Protection and protective group of functional groups not to be involved in the reaction of ingredients, and elimination of such protective group, and activation of functional groups to be involved in the reaction, etc. can be appropriately selected from among conventionally known groups or conventionally known measures. As alternative methods to obtain amides of polypeptides, there is, for example, a method to manufacture, after amidating and protecting α-carboxyl group of carboxy-terminal amino acid and then extending the peptide chain to the desired chain length on the side of amino group, a polypeptide eliminating the protective group of α-amino group of N-terminal of such peptide chain and a polypeptide eliminating the protective group of carboxyl group of C-terminal, and then these two peptides are condensed in the above-mentioned mixed solvent. The details of the condensation reaction are the same as described above. After purifying the protected polypeptide obtained by the condensation, the desired raw polypeptide can be obtained by eliminating all the protective groups by the above-mentioned method. Having purified this raw polypeptide using various known purification methods, if the main fraction is freeze-dried, an amide type of the desired polypeptide can be obtained. To get an ester type of the polypeptide, for example, make an amino acid ester by condensing α-carboxyl group of carboxy-terminal amino acid with the desired alcohols, and then, the ester type of the desired polypeptide can be obtained in the same way as the amide type of the polypeptide.

After the reaction, the peptides of the present invention can be purified and isolated by combining usual purification methods such as solvent extraction, distillation, column chromatography, liquid chromatography, re-crystallization, etc. If a peptide obtained by the above-mentioned methods is a salt-free type, it can be converted to a suitable salt by known methods, or if such peptide is a salt, it can be converted to a salt-free type by known methods.

Preferably, the new peptides of the present invention having the amino acid sequences indicated in the above-mentioned formula (1) to (58) can be manufactured by the methods described in the below-mentioned practical examples or similar methods. Also, the peptides of the present invention can be manufactured by the methods described in the International Publication No. 02/20561 Pamphlet or similar methods.

In the event that the peptides of the present invention are used as human drugs or veterinary drugs, usual usages may be applied. For example, according to need, they may be used by the oral route in the forms of sugar-coated tablets, capsules, elixirs, micro-capsulated formulations, etc. or by the parenteral route in the injectable forms of sterile solutions made of water or other pharmacologically acceptable liquid, suspensions, etc. For example, the peptides of the present invention can be manufactured as drugs by incorporating physiologically acceptable carriers, flavoring compound, excipients, vehicles, preservatives, stabilizers, binding agents in the unit dosage formulation forms required for the generally accepted pharmaceutical manufacturing. The quantity of any active ingredient in such drugs should be the optimal amount within the instructed scope.

Additives which can be incorporated into tablets, capsules, etc. include, for example, binding agents such as gelatin, cornstarch, tragacanth gum and gum Arabic, diluting agents such as crystalline cellulose, swelling agents such as cornstarch, gelatin and alginic acid, lubricant agents such as magnesium stearate, sweetening agents such as sucrose, lactose or saccharine, and flavoring agents such as peppermint, akamono oil or cherry. If the preparation form is capsules, it can contain a liquid carrier such as oil in addition to the above-mentioned materials. Sterile composition for injection can be formulated in accordance with usual pharmaceutical manufacturing practices, by dissolving or suspending active ingredients or natural vegetable oils such as sesame oil and copra oil in the vehicles such as injection solvents.

As watery solutions for injections, for example, isotonic solutions containing physiological saline, glucose and other adjunctive agents (e.g., D-sorbitol, D-mannitol, sodium chloride, etc.) can be used, and also can be used together with a suitable solubilizing agent such as alcohol (e.g., ethanol), polyalcohol (e.g., propylene glycohol, polyethylene glycohol), nonionic surfactant (e.g., Polysorbate 80™, (HCO-50) etc. Oily solutions include sesame oil, soybean oil, etc. and can be used together with solubilizing agents such as benzyl benzoate and benzylalcohol. They can also be combined with a buffering agent (e.g., phosphate buffer solution, sodium acetate buffer solution), a soothing agent (e.g., benzalkonium chloride, procaine hydrochloride, etc.), a stabilizer (e.g., human serum albumine, polyethylene glycohol, etc.), a preservative (e.g., benzylalcohol, phenol, etc.), an antioxidant, etc. A prepared injection is sterilely filled into an ampoule.

The pharmaceutical preparations manufactured as above are safe and low-toxic, and accordingly, can be administered to, for example, humans and mammals (e.g., mice, rats, guinea pigs, rabbits, sheep, swines, cows, cats, dogs, monkeys, hamadryas, chimpanzees, etc.).

The dose of a peptide of the present invention differs depending on the disease condition, etc. The dose in oral administration is usually about 0.1 to 1000 mg per one time per 60 kg of the body weight, preferably about 1.0 to 500 mg, and more preferably about 1.0 to 200 mg. The single dose in parenteral administration per 60 kg of the body weight differs depending on the administration subject, disease condition, administration method, etc.; for example, in case of injection, usually about 0.01 to 300 mg, preferably about 0.1 to 200 mg, and more preferably about 0.1 to 100 mg per one time may be administered intravenously. For other animals, the dose based on 60 kg of the body weight can be administered.

The peptides of the present invention have an anti-cancer activity, i.e. an activity for inhibiting movement of cancer cells and a cancer metastasis inhibitory activity. That is to say, the peptides of the present invention, as clearly seen in the below-mentioned practical examples, can be used as drugs for prevention and therapy of cancers, especially cancer metastasis, since they have a cancer metastasis inhibitory activity. Accordingly, the peptides of the present invention as anti-cancer drugs are useful for the amelioration, prevention and therapy of oral cancer, throat cancer, lip cancer, lingual cancer, gingival cancer, nasopharyngeal cancer, esophageal cancer, gastric cancer, small intestinal cancer, large intestinal cancer including colorectal cancer, liver cancer, gallbladder cancer, pancreatic cancer, nasal cancer, lung cancer, bone cancer, soft tissue cancer, skin cancer, melanoma, breast cancer, uterine cancer, ovarian cancer, prostate cancer, testicular cancer, penile cancer, bladder cancer, kidney cancer, brain cancer, thyroid cancer, lymphoma, leukemia, etc. Also, the peptides of the present invention have an anti-chronic rheumatoid arthritis activity, i.e., an inhibitory effect on T-cell movement. In other words, the peptides of the present invention, as clearly seen in the below-mentioned practical examples, can be used as drugs for the prevention and therapy of chronic rheumatoid arthritis, since they have an inhibitory action on T-cell movement. Thus, the peptides of the present invention are useful as drugs for the amelioration, prevention and therapy of chronic rheumatoid arthritis.

It is well-known that CXCR4 antagonistic compounds have an anti-viral activity. Accordingly, it would be obvious to the concerned industry that the peptides of the present invention can be used as preventive and therapeutic drugs for viral infectious disease (e.g. AIDS, SARS, etc.).

The use of the peptides of the present invention as anti-cancer drugs can be made concomitantly with other anti-cancer drugs (for example, chemotherapeutic drugs, immunotherapeutic drugs, or drugs inhibiting the activity of cell growth factors and their receptors) etc. (hereafter referred to as "concomitant drugs").

A peptide of the present invention exhibits a beneficial anti-cancer activity whenused in a single preparation form, but, the activity can be further enhanced when used together with one or more of the above-mentioned concomitant drugs (concomitant use of multiple drugs).

As the said "chemotherapeutic drugs", alkylating drugs, antimetabolites, anticancer antibiotics and plant-derived anti-cancer drugs can be exemplified.

Included in the examples of "alkylating drugs" are nitrogen mustard, nitrogen mustard-N-oxide hydrochloride, chlorambutyl, cyclophosphamide, ifosfamide, thiotepa, carboquone, improsulfan tosylte, busulfan, nimustine hydrochloride, mitobronitol, melphalan, dacarbazine, ranimustine, estramustine sodium phosphate, triethylenmelamine, carmustine, lomustine, streptozocin, pipobroman, etoglucide, altretamine, ambamustin, dibrospidium hydrochloride, fotemustin, prednimustin, pumitepa, ribomustin, temozolomide, treosulphan, trophosphamide, zinostatin stimalamer, carboquone, adzelecin, systemstin, bizelesin, platinum complex (carboplatin, cisplatin, miboplatin, nedaplatin, oxaliplatin, etc.).

"Antimetabolites" include, for example, mercaptopurine, 6-mercaptopurine riboside, thioinosine, methotrexate, enocitabine, cytarabine, cytarabine ocfosfate, ancitabine hydrochloride, 5-FU agents (e.g. fluorouracil, tegafur, UFT, doxifluridine, carmofur, galocitabine, emitefur, etc.), aminopterin, calcium leucovorin, tabloid, butocin, calcium folinate, calcium levofolinate, cladribine, emitefur, fludarabine, gemcitabine, hydroxycarbamide, pentostatin, piritrexim, idoxuridine, mitoguzaon, thiazofurin, ambamustin and gemicitabine.

"Anticancer antibiotics" include, for example, antracycline anti-cancer agents (doxorubicine hydrochloride, daunorubicin hydrochloride, aclarubicin hydrochloride, pirarubicin hydrochloride, epirubicin hydrochloride, etc.), actinomycin D, actinomycin C, mitomycin C, chromomycin A3, bleomycin hydrochloride, bleomycin sulfate, pleomycin sulfate, neocarzinostatin, mithramycin, sarcomycin, carzinophilin, mitotane, zorbicin hydrochloride, mitoxantrone hydrochloride and idarubicin hydrochloride.

"Plant-derived anti-cancer agents" include, for example, vinca alkaloid anti-cancer agents (vinblastine sulfate, vincristine sulfate, vindesin sulfate, vinorelbine, etc.), taxan anticancer agents (paclitaxel, docetaxel, etc.), etoposide, etoposide phosphate, teniposide and vinorelbine.

The "cell growth factors" in the said "drugs inhibiting the activity of cell growth factors and their receptors" can be any material that promotes the growth of cells, and include a factor exhibiting its activity at low concentration by the interaction with its receptor in the peptide of less than 20,000 molecular weight. Specifically, they include (1) EGF (epidermal growth factor) or a material having substantially the same activity as EGF (e.g., EGF, HER2 ligand, etc.), (2) insulin or a material having substantially the same activity as insulin [e.g., insulin, IGF (insulin-like growth factor)-1, IGF-2, etc.], (3) FGF (fibroblast growth factor) a material having substantially the same activity as FGF [e.g., acidic FGF, basic FGF, KGF (keratinocyte growth factor), FGF-10, etc.], (4) other cell growth factors [e.g., CSF (colony stimulating factor), EPO (erythropoietin), IL-2 (interleukin-2), NGF (nerve growth factor), PDGF (platelet-derived growth factor), TGFβ (transforming growth factorβ), HGF (hepatocyte growth factor), VEGF (vascular endothelial growth factor), etc.].

The said "receptors of cell growth factors can be any receptor that has binding capacity with the above-mentioned cell growth factors. Specifically, they include EGF receptor, HER2, insulin receptor, IGF receptor, FGF receptor-1 or FGF receptor-2, HGF receptor (c-met), VEG receptor, SCF receptor (c-kit).

The said "drugs inhibiting the activity of cell growth factors" include Herceptin (HER2 anti-body), GLEEVEC (c-met, c-kit, ab1 inhibitor), Iressa (EGF receptor inhibitor) etc.

Besides the above-mentioned drugs, topoisomerase I inhibitor (e.g., irinotecan, topotecan, etc.), topoisomerase II inhibitor (e.g., sobuzoxane, etc.), angiogenesis inhibitor, etc. can be used.

In the case of use of a peptide of the present invention as a preventive and/or therapeutic drug, it may be used concomitantly with other preventive and/or therapeutic drug(s) for rheumatoid arthritis. Drugs of such concomitant use include, for example, anti-inflammatory steroids (e.g., prednisolone, hydrocortisone, methyl-prednisolone, dexamethasone, betamethasone, etc.), nonsteroidal anti-inflammatory and analgesic drugs (e.g., indometacin, diclofenac, loxoprofen, ibuprofen, aspirin, piroxicam, sulindac, etc.) or hyaluronic acid formulations (e.g., sodium hyaluronate, etc.), COX-II inhibitors, etc.

The peptides of the present invention exhibit an effective anti-chronic rheumatoid arthritis activity in the single preparation form, but the effect can be further enhanced by the concomitant use (multi-drug use) together with one or more of the above-mentioned concomitant drugs.

In the concomitant use of the peptides of the present invention and concomitant drugs, the administration time of the peptides of the present invention and a concomitant drug is not limited, and a peptide of the present invention and a concomitant drug can be administered to the subject at the same time or at different times. The dose of a concomitant drug can follow the usual dose clinically adopted, and can be determined appropriately depending on the administration subject, administration route, disease conditions, combination, etc.

The administration mode of a peptide of the present invention and a concomitant drug is not particularly limited, and it is acceptable if a polypeptide of the present invention or a salt thereof and a concomitant drug are combined at the time of administration. Such administration mode may be, for example, (1) the administration of a single preparation formulated by the simultaneous combination of a peptide of the present invention and a concomitant drug, (2) the simultaneous administration by the same administration route of two different drugs—one being a drug formulated using a peptide of the present invention and the other being a concomitant drug, (3) the administration by the same route at different times of two different drugs—one being a drug formulated using a peptide of the present invention and the other being a concomitant drug, (4) the simultaneous administration by different routes of two different drugs—one being a drug formulated using a peptide of the present invention and the other being a concomitant drug, (5) the administration by different routes at different times of two different drugs—one being a drug formulated using a peptide of the present invention and the other being a concomitant drug (for example, the administration of a peptide of the present invention followed by a concomitant drug, or vice versa), etc. These administration modes are hereafter collectively referred to as "concomitant drug(s) of the present invention".

Any concomitant drug of the present invention has low toxicity, and accordingly, can be safely administered orally or parenterally (e.g., local, rectum, vein, etc.) in the form of pharmaceutical compositions prepared by mixing a peptide of the present invention and/or the above-mentioned concomitant drug with a pharmacologically acceptable carrier in accordance with a method known in the art. Such pharmaceutical compositions include, without limitation, tablets (including sugar-coated tablets and film-coated tablets), powders, granules, capsules (including soft capsules), solutions, injections, suppositories, sustained-release formulations, etc. An injection can be administered to the interior or proximal site of a tumor or directly to the lesion by intravenous, intramuscular, subcutaneous, intraorgan, intranasal, intradermal, eye dropping, intracerebral, intrarectal, intravaginal or intraperitoneal administration.

Pharmacogically acceptable carriers identical to those used for the above-mentioned pharmaceutical compositions of the present invention can be used in the manufacturing of the concomitant drugs of the present invention.

The combination ratio of any of the peptides of the present invention and a concomitant drug belonging to the concomitant drugs of the present invention can be determined appropriately depending on the subject to be administered, routes for administration, disease conditions, etc.

The content of a concomitant drug belonging to the concomitant drugs of the present invention varies depending on the drug preparation forms. It is usually about 0.01 to 100% by weight in the whole preparation, or preferably about 0.1 to 50% by weight, or most preferably about 0.5 to 20% by weight.

The content of an additive such as a carrier in the concomitant drugs of the present invention varies depending on the drug preparation forms. It is usually about 1 to 99.9% by weight in the whole preparation, or preferably about 10 to 90% by weight.

The present invention is described in further details by the following practical examples, which, however, will not limit the range of the present invention.

Manufacturing Example 1

Manufacturing of Polypeptide TC14003

[SEQ ID NO: 1]
H-Arg-Arg-Nal-Cys-Tyr-Cit-Lys-DLys-Pro-Tyr-Arg-
Cit-Cys-Arg-OH (TC14003)

1. Synthesis of TC14003 Protected Polypeptide Resin:

After removing Fmoc group from Alko resin attached with the first arginine of the 14-position (Fmoc-Arg(Pbf)-Alko-resin) by 20% piperidine/DMF, Fmoc-Cys(Trt)-OH (2.5 eq) of the 13-position was added, and condensation reaction by DIPCDI-HOBt method was conducted in DMF. The progress of the condensation reaction was monitored by ninhydrin test of Kaiser, E. et al. (Anal. Biochem., 34: 595 (1970)).

2. Introduction of Amino Acids of the 12-Position to 1-Position:

Similarly to the foregoing, Cit, Arg(Pbf), Tyr(t-Bu), Pro, DLys(Boc), Lys(Boc), Cit, Tyr(t-Bu), Cys(Trt), NaI, Arg (Pbf), Arg(Pbf) residues were sequentially introduced into the resin to yield the protected polypeptide resin.

3. Deprotection and Clearage of Polypeptide from the Resin and Purification:

After removing Fmoc group from the protected polypeptide resin by 20% piperidine/DMF treatment, the resulting polypeptide resin was treated by 1 M TMSBr-thioanisole/TFA(trifluoroacetic acid) mixture (in the presence of m-cresol (100 eq), ethanedithiol (300 eq)) at 25° C. for 2 hours. The resin was separated by filtration from the reaction mixture, washed with TFA twice, the mixture of the filtrate and wash solution was subjected to concentration in vacuo, the remaining residue was added with water-cooled dry ether, the resultant precipitation was separated from supernatant liquid by centrifugal sedimentation and decantation. The obtained residue was washed with cold ether, dissolved into 1 N acetic acid, and diluted by distilled water.

4. Cyclization by Air Oxidation:

Diluted water solution of the above-mentioned polypeptide was adjusted to pH7.5 by concentrated ammonia water, and was cyclized by ventilated air oxidation. This water solution was purified by preparative HPLC(COSMOSIL 5C18 AR-II column: acetonitrile-water) and gel filtration chromatography (Sephadex G-15, eluate: 0.1 N AcOH), a polypeptide of a single peak was obtained and freeze-dried. The purity was confirmed by HPLC.

Manufacturing Example 2

Manufacturing of TC14005

[SEQ ID NO: 1]
H-Arg-Arg-Nal-Cys-Tyr-Arg-Lys-DCit-Pro-Tyr-Arg-Cit-Cys-Arg-OH (TC14005)

TC14005 was manufactured by the same method as Manufacturing Example 1. However, DCit replaced DLys(Boc) of the 8-position and Arg(Pbf) replaced Cit of the 6-position respectively during the introduction of the amino acids from the 12-postion through the 1-position.

Manufacturing Example 3

Manufacturing of TC14011

[SEQ ID NO: 1]
H-Arg-Arg-Nal-Cys-Tyr-Cit-Lys-DCit-Pro-Tyr-Arg-Cit-Cys-Arg-OH (TC14011)

TC14011 was manufactured by the same method as Manufacturing Example 1. However, DCit replaced Dlys(Boc) of the 8-position during the introduction of the amino acids from the 12-postion through the 1-position.

Manufacturing Example 4

Manufacturing of TC14013

[SEQ ID NO: 1]
H-Arg-Arg-Nal-Cys-Tyr-Cit-Lys-DLys-Pro-Tyr-Cit-Cit-Cys-Arg-OH (TC14013)

TC14013 was manufactured by the same method as Manufacturing Example 1. However, Cit replaced Arg(Pbf) of the 11-position during the introduction of the amino acids from the 12-postion through the 1-position.

Manufacturing Example 5

Manufacturing of TC14015

[SEQ ID NO: 1]
H-Cit-Arg-Nal-Cys-Tyr-Cit-Lys-DLys-Pro-Tyr-Arg-Cit-Cys-Arg-OH (TC14015)

TC14015 was manufactured by the same method as Manufacturing Example 1. However, Cit replaced Arg(Pbf) of the 1-position during the introduction of the amino acids from the 12-postion through the 1-position.

Manufacturing Example 6

Manufacturing of TC14017

[SEQ ID NO: 1]
H-Cit-Arg-Nal-Cys-Tyr-Arg-Lys-DCit-Pro-Tyr-Arg-Cit-Cys-Arg-OH (TC14017)

TC14017 was manufactured by the same method as Manufacturing Example 1. However, DCit replaced DLys(Boc) of the 8-position, Arg(Pbf) replaced Cit of the 6-position and Cit replaced Arg(Pbf) of the 1-position respectively during the introduction of the amino acids from the 12-postion through the 1-position.

Manufacturing Example 7

Manufacturing of TC14019

[SEQ ID NO: 1]
H-Arg-Arg-Nal-Cys-Tyr-Arg-Lys-DCit-Pro-Tyr-Cit-Cit-Cys-Arg-OH (TC14019)

TC14019 was manufactured by the same method as Manufacturing Example 1. However, Cit replaced Arg(Pbf) of the 11-position, DCit replaced DLys(Boc) of the 8-position, and Arg(Pbf) replaced Cit of the 6-position during the introduction of the amino acids from the 12-postion through the 1-position.

Manufacturing Example 8

Manufacturing of TC14021

[SEQ ID NO: 1]
H-Cit-Arg-Nal-Cys-Tyr-Arg-Lys-DLys-Pro-Tyr-Cit-
Cit-Cys-Arg-OH (TC14021)

TC14021 was manufactured by the same method as Manufacturing Example 1. However, Cit replaced Arg(Pbf) of the 11-position, Arg(Pbf) replaced Cit of the 6-position and Cit replaced Arg(Pbf) of the 1-position respectively during the introduction of the amino acids from the 12-postion through the 1-position.

Manufacturing Example 9

Manufacturing of TC14012

[SEQ ID NO: 1]
H-Arg-Arg-Nal-Cys-Tyr-Cit-Lys-DCit-Pro-Tyr-Arg-
Cit-Cys-Arg-NH$_2$ (TC14012)

1. Synthesis of Tc14012 Protected Polypeptide Resin:

After removing Fmoc group from Fmoc-Rink amide resin by 20% piperidine/DMF, Fmoc-Arg(Pbf)-OH (2.5 eq) corresponding to the 14-position was added, and condensation reaction by DIPCDI-HOBt method was conducted in DMF. The progress of the condensation reaction was monitored by ninhydrin test of Kaiser, E. et al. (Anal. Biochem., 34: 595 (1970)).

2. Introduction of Amino Acids of the 13-Position to 1 Position:

Similarly to the foregoing, Cys(Trt), Cit, Arg(Pbf), Tyr(t-Bu), Pro, DCit, Lys(Boc), Cit, Tyr(t-Bu), Cys(Trt), NaI, Arg(Pbf), Arg(Pbf) residues were sequentially introduced into the Rink amide resin, and the protected polypeptide resin was obtained.

3. Deprotection and Clearage of Polypeptide from the Resin and Purification:

After removing Fmoc group from the protected polypeptide resin by 20% piperidine/DMF treatment, the resulting polypeptide resin was treated by 1 M TMSBr-thioanisole/TFA(trifluoroacetic acid) mixture (in the presence of m-cresol (100 eq), ethanedithiol (300 eq)) at 25° C. for 3 hours. The resin was separated by filtration from the reaction mixture, washed by TFA twice, the mixture of the filtrate and the wash solution was subjected to concentration in vacuo, the remaining residue was added with water-cooled dry ether, the resulting precipitation was separated from supernatant liquid by centrifugal sedimentation and decantation. The obtained residue was washed with cold ether, dissolved into 1 N acetic acid, and diluted by distilled water.

4. Cyclization by Air Oxidation:

Diluted water solution of the above-mentioned polypeptide was adjusted to pH 7.5 by concentrated ammonia water, and was cyclized by ventilated air oxidation. This water solution was purified by preparative HPLC(COSMOSIL 5C18 AR-II column: acetonitrile-water) and gel filtration chromatography (Sephadex G-15, eluate: 0.1 N AcOH), a polypeptide of a single peak was obtained and freeze-dried. The purity was confirmed by HPLC.

Manufacturing Example 10

Manufacturing of TC14014

[SEQ ID NO: 1]
H-Arg-Arg-Nal-Cys-Tyr-Cit-Lys-DLys-Pro-Tyr-Cit-
Cit-Cys-Arg-NH$_2$ (TC14014)

TC14014 was manufactured by the same method as Manufacturing Example 9. However, Cit replaced Arg(Pbf) of the 11-position and DLys(Boc) replaced DCit of the 8-position respectively during the introduction of the amino acids from the 13-postion through the 1-position.

Manufacturing Example 11

Manufacturing of TC14016

[SEQ ID NO: 1]
H-Cit-Arg-Nal-Cys-Tyr-Cit-Lys-DLys-Pro-Tyr-Arg-
Cit-Cys-Arg-NH$_2$ (TC14016)

TC14016 was manufactured by the same method as Manufacturing Example 9. However, Dlys(Boc) replaced DCit of the 8-position and Cit replaced Arg(Pbf) of the 1-position respectively during the introduction of the amino acids from the 13-postion through the 1-position.

Manufacturing Example 12

Manufacturing of TC14018

[SEQ ID NO: 1]
H-Cit-Arg-Nal-Cys-Tyr-Arg-Lys-DCit-Pro-Tyr-Arg-
Cit-Cys-Arg-NH$_2$ (TC14018)

TC14018 was manufactured by the same method as Manufacturing Example 9. However, Arg(Pbf) replaced Cit of the 6-position and Cit replaced Arg(Pbf) of the 1-position respectively during the introduction of the amino acids from the 13-postion through the 1-position.

Manufacturing Example 13

Manufacturing of TC14020

[SEQ ID NO: 1]
H-Arg-Arg-Nal-Cys-Tyr-Arg-Lys-DCit-Pro-Tyr-Cit-
Cit-Cys-Arg-NH$_2$ (TC14020)

TC14020 was manufactured by the same method as Manufacturing Example 9. However, Cit replaced Arg(Pbf) of the 11-position and Arg(Pbf) replaced Cit of the 6-position respectively during the introduction of the amino acids from the 13-postion through the 1-position.

Manufacturing Example 14

Manufacturing of TC14022

[SEQ ID NO: 1]
H-Cit-Arg-Nal-Cys-Tyr-Arg-Lys-DLys-Pro-Tyr-Cit-
Cit-Cys-Arg-NH$_2$ (TC14022)

TC14022 was manufactured by the same method as Manufacturing Example 9. However, Cit replaced Arg(Pbf) of the 11-position, DLys(Boc) replaced DCit of the 8-position, Arg(Pbf) replaced Cit of the 6-position and Cit replaced Arg(Pbf) of the 1-position respectively during the introduction of the amino acids from the 13-postion through the 1-position.

Manufacturing Example 15

Manufacturing of TA14001, TA14005-TA14009, TC14001 and TC14004

```
(TA14001)
                                                  [SEQ ID NO: 1]
H-Ala-Arg-Nal-Cys-Tyr-Arg-Lys-DLys-Pro-Tyr-Arg-Cit-Cys-Arg-OH (TA14005)
                                                  [SEQ ID NO: 1]
H-Arg-Arg-Nal-Cys-Tyr-Ala-Lys-DLys-Pro-Tyr-Arg-Cit-Cys-Arg-OH (TA14006)
                                                  [SEQ ID NO: 1]
H-Arg-Arg-Nal-Cys-Tyr-Arg-Ala-DLys-Pro-Tyr-Arg-Cit-Cys-Arg-OH (TA14007)
                                                  [SEQ ID NO: 1]
H-Arg-Arg-Nal-Cys-Tyr-Arg-Lys-DAla-Pro-Tyr-Arg-Cit-Cys-Arg-OH (TA14008)
                                                  [SEQ ID NO: 1]
H-Arg-Arg-Nal-Cys-Tyr-Arg-Lys-DLys-Ala-Tyr-Arg-Cit-Cys-Arg-OH (TA14009)
                                                  [SEQ ID NO: 1]
H-Arg-Arg-Nal-Cys-Tyr-Arg-Lys-DLys-Pro-Ala-Arg-Cit-Cys-Arg-OH (TC14001)
                                                  [SEQ ID NO: 1]
H-Cit-Arg-Nal-Cys-Tyr-Arg-Lys-DLys-Pro-Tyr-Arg-Cit-Cys-Arg-OH (TC14004)
                                                  [SEQ ID NO: 1]
H-Arg-Arg-Nal-Cys-Tyr-Arg-Cit-DLys-Pro-Tyr-Arg-Cit-Cys-Arg-NH$_2$
```

The above-listed TA14001, TA14005-TA14009, TC14001 and TC14004 can be manufactured by the same method as Manufacturing Example 1 or 9 with replacements of amino acids.

Manufacturing Example 16

Manufacturing of AcTC14003, AcTC14005, AcTC14011-AcTC14022

```
(AcTC14003)
                                                   [SEQ ID NO: 11]
Ac-Arg-Arg-Nal-Cys-Tyr-Cit-Lys-DLys-Pro-Tyr-Arg-Cit-Cys-Arg-OH (AcTC14005)
                                                   [SEQ ID NO: 12]
Ac-Arg-Arg-Nal-Cys-Tyr-Arg-Lys-DCit-Pro-Tyr-Arg-Cit-Cys-Arg-OH (AcTC14011)
                                                   [SEQ ID NO: 13]
Ac-Arg-Arg-Nal-Cys-Tyr-Cit-Lys-DCit-Pro-Tyr-Arg-Cit-Cys-Arg-OH (AcTC14013)
                                                   [SEQ ID NO: 14]
Ac-Arg-Arg-Nal-Cys-Tyr-Cit-Lys-DLys-Pro-Tyr-Cit-Cit-Cys-Arg-OH (AcTC14015)
                                                   [SEQ ID NO: 15]
Ac-Cit-Arg-Nal-Cys-Tyr-Cit-Lys-DLys-Pro-Tyr-Arg-Cit-Cys-Arg-OH (AcTC14017)
                                                   [SEQ ID NO: 16]
Ac-Cit-Arg-Nal-Cys-Tyr-Arg-Lys-DCit-Pro-Tyr-Arg-Cit-Cys-Arg-OH (AcTC14019)
```

-continued

[SEQ ID NO: 17]
Ac-Arg-Arg-Nal-Cys-Tyr-Arg-Lys-DCit-Pro-Tyr-Cit-Cit-Cys-Arg-OH (AcTC14021)

[SEQ ID NO: 18]
Ac-Cit-Arg-Nal-Cys-Tyr-Arg-Lys-DLys-Pro-Tyr-Cit-Cit-Cys-Arg-OH (AcTC14012)

[SEQ ID NO: 19]
Ac-Arg-Arg-Nal-Cys-Tyr-Cit-Lys-DCit-Pro-Tyr-Arg-Cit-Cys-Arg-NH$_2$ (AcTC14014)

[SEQ ID NO: 20]
Ac-Arg-Arg-Nal-Cys-Tyr-Cit-Lys-DLys-Pro-Tyr-Cit-Cit-Cys-Arg-NH$_2$ (AcTC14016)

[SEQ ID NO: 21]
Ac-Cit-Arg-Nal-Cys-Tyr-Cit-Lys-DLys-Pro-Tyr-Arg-Cit-Cys-Arg-NH$_2$ (AcTC14018)

[SEQ ID NO: 22]
Ac-Cit-Arg-Nal-Cys-Tyr-Arg-Lys-DCit-Pro-Tyr-Arg-Cit-Cys-Arg-NH$_2$ (AcTC14020)

[SEQ ID NO: 23]
Ac-Arg-Arg-Nal-Cys-Tyr-Arg-Lys-DCit-Pro-Tyr-Cit-Cit-Cys-Arg-NH$_2$ (AcTC14022)

[SEQ ID NO: 24]
Ac-Cit-Arg-Nal-Cys-Tyr-Arg-Lys-DLys-Pro-Tyr-Cit-Cit-Cys-Arg-NH$_2$

Acetylated TC14003, TC14005, TC14011-TC14022 were manufactured by the same method as Manufacturing Example 1 to 14. However, after removing Fmoc group from the protected polypeptide resin by 20% piperidine/DMF treatment, the resulting polypeptide resin was acetylated by acetic anhydride (100 eq)-pyridine (100 eq)/DMF treatment, and treated by 1M TMSBr-thioanisole/TFA(trifluoroacetic acid) mixture (in the presence of m-cresol (100 eq), ethanedithiol (300 eq)) at 25° C. for 2 hours (in case of C-terminal being carboxylic acid) or for 3 hours (in case of C-terminal being amide).

Manufacturing Example 17

Manufacturing of Polypeptide TE14005

(TE14005)
[SEQ ID NO: 29]
H-Arg-Arg-Nal-Cys-Tyr-Arg-Lys-DGlu-Pro-Tyr-Arg-Cit-Cys-Arg-OH

1. Synthesis of TE14005 Protected Polypeptide Resin:

After removing Fmoc group from Fmoc-Arg(Pbf)-Alko resin (0.74 mmol/g) 270 mg (0.2 mmol) attached with the first arginine of the 14-position by 20% piperidine/DMF, Fmoc-Cys(Trt)-OH (2.5 eq) corresponding to the 13-position was added, and condensation reaction by DIPCDI-HOBt method was conducted in DMF. The progress of the condensation reaction was monitored by ninhydrin test of Kaiser, E. et al. (Anal. Biochem., 34: 595 (1970)).

2. Introduction of Amino Acids of the 12-Position to 1 Position:

Similarly to the foregoing, Cit, Arg(Pbf), Tyr(t-Bu), Pro, DGlu(0-t-Bu), Lys(Boc), Arg(Pbf), Tyr(t-Bu), Cys(Trt), NaI, Arg(Pbf), Arg(Pbf) residue was sequentially introduced into the resin, and protected polypeptide resin was obtained.

3. Deprotection and Clearage of Polypeptide from Resin and Purification:

After removing Fmoc group from the protected polypeptide resin (200 mg) by 20% piperidine/DMF treatment, the resulting polypeptide resin was treated by 10 mL of 1 M TMSBr-thioanisole/TFA(trifluoroacetic acid) mixture (in the presence of m-cresol(100 eq), ethandithiol (300 eq)) at 25° C. for 2 hours. The resin was separated by filtration from the reaction mixture, was washed with TFA 1 mL twice, the mixture of the filtrate and the wash solution was subjected to concentration in vacuo, the remaining residue was added with 30 mL of water-cooled dry ether, the resultant sediment was separated from supernatant liquid by centrifugal sedimentation and decantation. The obtained residue was cleansed by cold ether, dissolved into 50 mL of 1 N acetic acid, and diluted to 250 mL by distilled water.

4. Cyclization by Air Oxidation:

Diluted water solution of the above-mentioned polypeptide was adjusted to pH 7.5 by concentrated ammonia water, and was cyclized by ventilated air oxidation. This water solution was purified by preparative HPLC(COSMOSIL 5C18 AR-II column: acetonitrile water) and gel filtration chromatography (Sephadex G-15, eluate: 0.1 N AcOH), a polypeptide of a single peak was obtained and freeze-dried. The purity was confirmed by HPLC.

Yield: 24.1 mg (7 AcOh salt) (21.3%)

$[\alpha]D23.6=-5.36$ (c1.12, H2O)

Ionspray mass spectrum (IS-MS): C89H136N32O2O52

Calculated Value: 2038.38 Actual Measurement Value: 2038

(triple stage quadrupole mass spectrometry API-IIIE (Sciex))

Manufacturing Example 18

Manufacturing of Polypeptide TE14001

(TE14001)
[SEQ ID NO: 25]
H-DGlu-Arg-Nal-Cys-Tyr-Arg-Lys-DLys-Pro-Tyr-Arg-Cit-Cys-Arg-OH

TE14001 was manufactured by the same method as Manufacturing Example 17. However, DLys(Boc) replaced DGlu (O-t-Bu) of the 8-position, and DGlu(O-t-Bu) replaced Arg (Pbf) of the 1-position respectively during the introduction of the amino acids from the 12-postion through the 1-position.

Manufacturing Example 19

Manufacturing of Polypeptide TE14002

(TE14002)
[SEQ ID NO: 26]
H-Arg-Glu-Nal-Cys-Tyr-Arg-Lys-DLys-Pro-Tyr-Arg-

Cit-Cys-Arg-OH

TE14002 was manufactured by the same method as Manufacturing Example 17. However, DLys(Boc) replaced DGlu (O-t-Bu) of the 8-position, and Glu(O-t-Bu) replaced Arg (Pbf) of the 2-position respectively during the introduction of the amino acids from the 12-postion through the 1-position.

Manufacturing Example 20

Manufacturing of Polypeptide TC14003

(TE14003)
[SEQ ID NO: 27]
H-Arg-Arg-Nal-Cys-Tyr-Glu-Lys-DLys-Pro-Tyr-Arg-

Cit-Cys-Arg-OH

TE14003 was manufactured by the same method as Manufacturing Example 17. However, DLys(Boc) replaced DGlu (O-t-Bu) of the 8-position, and DGlu(O-t-Bu) replaced Arg (Pbf) of the 6-position respectively during the introduction of the amino acids from the 12-postion through the 1-position.

Manufacturing Example 21

Manufacturing of Polypeptide TE14004

(TE14004)
[SEQ ID NO: 28]
H-Arg-Arg-Nal-Cys-Tyr-Arg-Glu-DLys-Pro-Tyr-Arg-

Cit-Cys-Arg-OH

TE14004 was manufactured by the same method as Manufacturing Example 17.
However, Dlys(Boc) replaced DGlu(O-t-Bu) of the 8-position, and DGlu(O-t-Bu) replaced Lys(Boc) of the 7-position respectively during the introduction of the amino acids from the 12-postion through the 1-position.

Manufacturing Example 22

Manufacturing of Polypeptide TE14006

(TE14006)
[SEQ ID NO: 30]
H-Arg-Arg-Nal-Cys-Tyr-Arg-Lys-DLys-Pro-Tyr-Glu-

Cit-Cys-Arg-OH

TE14006 was manufactured by the same method as Manufacturing Example 17.
However, DLys (Boc) replaced DGlu(O-t-Bu) of the 8-position, and DGlu(O-t-Bu) replaced Arg(Pbf) of the 11-position respectively during the introduction of the amino acids from the 12-postion through the 1-position.

Manufacturing Example 23

Manufacturing of Polypeptide TE14007

(TE14007)
[SEQ ID NO: 31]
H-Arg-Arg-Nal-Cys-Tyr-Arg-Lys-DLys-Pro-Tyr-Arg-

Cit-Cys-Glu-OH

TE14007 was manufactured by the same method as Manufacturing Example 17. However, instead of Fmoc-Arg(Pbf)-Alko resin attached with the first arginine of the 14-position, Fmoc-Glu(O-t-Bu)-Alko resin attached with glutamic acid of the 14-position was used, and also, DLys(Boc) replaced DGlu (O-t-Bu) of the 8-position during the introduction of the amino acids from the 12-postion through the 1-position.

Manufacturing Example 24

Manufacturing of Polypeptide TE14011>

(TE14011)
[SEQ ID NO: 32]
H-Arg-Arg-Nal-Cys-Tyr-Cit-Lys-DGlu-Pro-Tyr-Arg-

Cit-Cys-Arg-NH$_2$

1. Synthesis of TE14011 Protected Polypeptide Resin:
After removing Fmoc group from Fmoc-Rink amide resin by 20% piperidine/DMF, Fmoc-Arg(Pbf)-OH (2.5 eq) corresponding to the 14-position was added, and condensation reaction by DIPCDI-HOBt method was conducted in DMF. The progress of the condensation reaction was monitored by ninhydrin test of Kaiser, E. et al. (Anal. Biochem. 34: 595 (1970)).

2. Introduction of Amino Acids of the 13-Position to the 1-Position:
Similarly to the foregoing, Cys(Trt), Cit, Arg(Pbf), Tyr(t-Bu), Pro, DGlu(O-t-Bu), Lys(Boc), Cit, Tyr(t-Bu), Cys(Trt), Nal, Arg(Pbf), Arg(Pbf) residue was sequentially introduced into the Rink amide resin, and the protected polypeptide resin was obtained.

3. Deprotection and Cleavage of Polypeptide from Resin and Purification:
After removing Fmoc group from the protected polypeptide resin by 20% piperidine/DMF treatment, the resulting polypeptide resin was treated by 1M TMSBr-thioanisole/TFA(trifluoroacetic acid) mixture (in the presence of m-cresol (100 eq), ethanedithiol (300 eq)) at 25° C. for 3 hours. The resin was separated by filtration from the reaction mixture, washed with TFA twice, the mixture of the filtrate and the wash solution was subjected to concentration in vacuo, the remaining residue was added with water-cooled dry ether, the resulting precipitation was separated from supernatant liquid by centrifugal sedimentation and decantation. The obtained residue was cleansed by cold ether, dissolved into 1 N acetic acid, and diluted by distilled water.

4. Cyclization by Air Oxidation:

Diluted water solution of the above-mentioned polypeptide was adjusted to pH 7.5 by concentrated ammonia water, and was cyclized by ventilated air oxidation. This water solution was purified by preparative HPLC(COSMOSIL 5C18 AR-II column: acetonitrile water) and gel filtration chromatography (Sephadex G-15, eluate: 0.1N AcOH), a polypeptide of a single peak was obtained and freeze-dried. The purity was confirmed by HPLC.

Manufacturing Example 25

Manufacturing of Polypeptide TE14012

(TE14012) [SEQ ID NO: 33]
H-Arg-Arg-Nal-Cys-Tyr-DGlu-Lys-DCit-Pro-Tyr-Arg-
Cit-Cys-Arg-NH$_2$

TE14012 was manufactured by the same method as Manufacturing Example 24. However, DCit replaced DGlu(O-t-Bu) of the 8-position, and DGlu(O-t-Bu) replaced Cit of the 6-position respectively during the introduction of the amino acids from the 13-postion through the 1-position.

Manufacturing Example 26

Manufacturing of Polypeptide TE14013

(TE14013) [SEQ ID NO: 34]
H-Arg-Arg-Nal-Cys-Tyr-DGlu-Lys-DGlu-Pro-Tyr-Arg-
Cit-Cys-Arg-NH$_2$

TE14013 was manufactured by the same method as Manufacturing Example 24.

However, DGlu(O-t-Bu) replaced Cit of the 6-position during the introduction of the amino acids from the 13-postion through the 1-position.

Manufacturing Example 27

Manufacturing of Polypeptide TE14014

(TE14014) [SEQ ID NO: 35]
H-DGlu-Arg-Nal-Cys-Tyr-Cit-Lys-DGlu-Pro-Tyr-Arg-
Cit-Cys-Arg-NH$_2$

TE14014 was manufactured by the same method as Manufacturing Example 24. However, DGlu(O-t-Bu) replaced Arg (Pbf) of the 1-position during the introduction of the amino acids from the 13-postion through the 1-position.

Manufacturing Example 28

Manufacturing of Polypeptide TE14015

(TE14015) [SEQ ID NO: 36]
H-Arg-Arg-Nal-Cys-Tyr-Cit-Lys-DGlu-Pro-DGlu-Arg-
Cit-Cys-Arg-NH$_2$

TE14015 was manufactured by the same method as Manufacturing Example 24. However, DGlu(O-t-Bu) replaced Tyr (t-Bu) of the 10-position during the introduction of the amino acids from the 13-postion through the 1-position.

Manufacturing Example 29

Manufacturing of Polypeptide TE14016

(TE14016) [SEQ ID NO: 37]
H-Arg-Arg-Nal-Cys-Tyr-Cit-Lys-DGlu-Pro-Tyr-Arg-
DGlu-Cys-Arg-NH$_2$

TE14016 was manufactured by the same method as Manufacturing Example 24. However, DGlu(O-t-Bu) replaced Cit of the 12-position during the introduction of the amino acids from the 13-postion through the 1-position.

Manufacturing Example 30

Manufacturing of Polypeptide AcTE14014-AcTE14016

(AcTE14014) [SEQ ID NO: 38]
Ac-DGlu-Arg-Nal-Cys-Tyr-Cit-Lys-DGlu-Pro-Tyr-Arg-
Cit-Cys-Arg-NH$_2$ (AcTE14015) [SEQ ID NO: 39]
Ac-Arg-Arg-Nal-Cys-Tyr-Cit-Lys-DGlu-Pro-DGlu-Arg-
Cit-Cys-Arg-NH$_2$ (AcTE14016) [SEQ ID NO: 40]
Ac-Arg-Arg-Nal-Cys-Tyr-Cit-Lys-DGlu-Pro-Tyr-Arg-
DGlu-Cys-Arg-NH$_2$

Acetylated TE14014-TE14016 were manufactured by the same method as Manufacturing Example 27-29. However, after removing Fmoc group from the protected polypeptide resin by 20% piperidine/DMF treatment, the resulting polypeptide resin was acetylated by acetic anhydride (100 eq)-pyridine (100 eq)/DMF treatment, and treated by 1 M TMSBr-thioanisole/TFA(trifluoroacetic acid) mixture (in the presence of m-cresol (100 eq), ethanedithiol (300 eq)) at 25° C. for 3 hours.

Manufacturing Example 31

Manufacturing of Polypeptide TF1

(TF1: AcTE14011) [SEQ ID NO: 41]
Ac-Arg-Arg-Nal-Cys-Tyr-Cit-Lys-DGlu-Pro-Tyr-Arg-
Cit-Cys-Arg-NH$_2$

TF1 was manufactured by the same method as Manufacturing Example 24.

However, after removing Fmoc group from the protected polypeptide resin by 20% piperidine/DMF treatment, the resulting polypeptide resin was acetylated by acetic anhydride (100 eq)-pyridine (100 eq)/DMF treatment, and treated by 1 M TMSBr-thioanisole/TFA(trifluoroacetic acid) mixture (in the presence of m-cresol (100 eq), ethanedithiol (300 eq)) at 25° C. for 2 hours (in case of C-terminal being carboxylic acid) or for 3 hours (in case of C-terminal being amide).

Manufacturing Example 32

Manufacturing of Polypeptide TF2

(TF2: guanyl-TE14011)
[SEQ ID NO: 42]
guanyl-Arg-Arg-Nal-Cys-Tyr-Cit-Lys-DGlu-Pro-Tyr-Arg-Cit-Cys-Arg-NH$_2$ TF2 was manufactured by the same method as Manufacturing Example 24.

However, after removing Fmoc group from the protected polypeptide resin by 20% piperidine/DMF treatment, the resulting polypeptide resin was guanylated by 1H-pyrazole-1-carboxamidine (5 eq)-N,N-diisopropylethylamine (10 eq)/DMF treatment, and treated by 1M TMSBr-thioanisole/TFA (trifluoroacetic acid) mixture (in the presence of m-cresol (100 eq), ethandithiol (300 eq)) at 25° C. for 3 hours.

Manufacturing Example 33

Manufacturing of Polypeptide TF3

(TF3: TMguanyl-TE14011)
[SEQ ID NO: 43]
TMguanyl-Arg-Arg-Nal-Cys-Tyr-Cit-Lys-DGlu-Pro-Tyr-Arg-Cit-Cys-Arg-NH$_2$ TF3 was manufactured by the same method as Manufacturing Example 24.

However, after removing Fmoc group from the protected polypeptide resin by 20% piperidine/DMF treatment, the resulting polypeptide resin was tetramethylguanylated by 2-(1H-benzotriazole-1-yl)-1,1,3,3-tetramethyluronium tetrafluoroborate (5 eq)/DMF treatment, and treated with 1 M TMSBr-thioanisole/TFA(trifluoroacetic acid) mixture (in the presence of m-cresol (100 eq), ethanedithiol (300 eq)) at 25° C. for 3 hours.

Manufacturing Example 34

Manufacturing of Polypeptide TF4

(TF4: TMguanyl-TE14011 (2-14))
[SEQ ID NO: 44]
TMguanyl-Arg-Nal-Cys-Tyr-Cit-Lys-DGlu-Pro-Tyr-Arg-Cit-Cys-Arg-NH$_2$ TF4 was manufactured by the same method as Manufacturing Example 24. However, arginine of the 1-position was not condensed.

Manufacturing Example 35

Manufacturing of Polypeptide TF5

(TF5: 4F-benzoyl-TE14011)
[SEQ ID NO: 45]
4F-benzoyl-Arg-Arg-Nal-Cys-Tyr-Cit-Lys-DGlu-Pro-Tyr-Arg-Cit-Cys-Arg-NH$_2$ TF5 was manufactured by the same method as Manufacturing Example 24. However, after removing Fmoc group from the protected polypeptide resin by 20% piperidine/DMF treatment, the resulting polypeptide resin was condensed with 4-fluorobenzoic acid (2.5 eq) by DIPCDI-HOBt method, and treated with 1 M TMSBr-thioanisole/TFA(trifluoroacetic acid) mixture (in the presence of m-cresol (100 eq), ethanedithiol (300 eq)) at 25° C. for 3 hours.

Manufacturing Example 36

Manufacturing of Polypeptide TF6

(TF6: 2F-benzoyl-TE14011)
[SEQ ID NO: 46]
2F-benzoyl-Arg-Arg-Nal-Cys-Tyr-Cit-Lys-DGlu-Pro-Tyr-Arg-Cit-Cys-Arg-NH$_2$ TF6 was manufactured by the same method as Manufacturing Example 24.

However, after removing Fmoc group from the polypeptide resin protected by protecting group by 20% piperidine/DMF treatment, the resulting polypeptide resin was condensed with 2-fluorobenzoic acid (2.5 eq) by DIPCDI-HOBt method, and treated with 1M TMSBr-thioanisole/TFA(trifluoroacetic acid) mixture (in the presence of m-cresol (100 eq), ethandithiol (300 eq)) at 25° C. for 3 hours.

Manufacturing Example 37

Manufacturing of Polypeptide TF7

(TF7: APA-TE14011 (2-14))
[SEQ ID NO: 47]
APA-Arg-Nal-Cys-Tyr-Cit-Lys-DGlu-Pro-Tyr-Arg-Cit-Cys-Arg-NH$_2$

TF7 was manufactured by the same method as Manufacturing Example 24.

However, instead of Arg(Pbf) of the 1-position, Fmoc-aminopentanoic acid was introduced after the introduction of the amino acids from the 13-postion through the 1-position.

Manufacturing Example 38

Manufacturing of Polypeptide TF8

(TF8: desamino-R-TE14011 (2-14))
                                    [SEQ ID NO: 48]
desamino-R-Arg-Nal-Cys-Tyr-Cit-Lys-DGlu-Pro-Tyr- Arg-Cit-Cys-Arg-NH$_2$ TF8 was manufactured by the same method as Manufacturing Example 24.

However, instead of Arg(Pbf) of the 1-position, Fmoc-5-aminopentanic acid was introduced after the introduction of the amino acids from the 13-postion through the 1-position. Furthermore, after removing Fmoc group from the protected polypeptide resin by 20% piperidine/DMF treatment, the resulting polypeptide resin was guanylated by 1H-pyrazole-1-carboxamidine (5 eq)/DMF treatment, and treated by 1 M TMSBr-thioanisole/TFA(trifluoroacetic acid) mixture (in the presence of m-cresol (100 eq), ethanedithiol (300 eq)) at 25° C. for 3 hours.

Manufacturing Example 39

Manufacturing of Polypeptide TF9

(TF9: guanyl-TE14011 (2-14))
                                    [SEQ ID NO: 49]
guanyl-Arg-Nal-Cys-Tyr-Cit-Lys-DGlu-Pro-Tyr-Arg- Cit-Cys-Arg-NH$_2$ TF9 was manufactured by the same method as Manufacturing Example 32.

However, arginine of the 1-position was not condensed.

Furthermore, after removing Fmoc group from the protected polypeptide resin by 20% piperidine/DMF treatment, the resulting polypeptide resin was guanylated by 1H-pyrazole-1-carboxamidine (5 eq)/DMF treatment, and treated by 1 M TMSBr-thioanisole/TFA(trifluoroacetic acid) mixture (in the presence of m-cresol (100 eq), ethanedithiol (300 eq)) at 25° C. for 3 hours.

Manufacturing Example 40

Manufacturing of Polypeptide TF10

(TF10: succinyl-TE14011 (2-14))
                                    [SEQ ID NO: 50]
succinyl-Arg-Nal-Cys-Tyr-Cit-Lys-DGlu-Pro-Tyr-Arg- Cit-Cys-Arg-NH$_2$ TF10 was manufactured by the same method as Manufacturing Example 24.

However, arginine of the 1-position was not condensed.

Also, after removing Fmoc group from the protected polypeptide resin by 20% piperidine/DMF treatment, the resulting polypeptide resin was hemisuccinylated by succinic anhydride (5 eq)/pyridine treatment, and treated by 1 M TMSBr-thioanisole/TFA(trifluoroacetic acid) mixture (in the presence of m-cresol (100 eq), ethanedithiol (300 eq)) at 25° C. for 3 hours.

Manufacturing Example 41

Manufacturing of Polypeptide TF11

(TF11: glutaryl-TE14011 (2-14))
                                    [SEQ ID NO: 51]
glutaryl-Arg-Nal-Cys-Tyr-Cit-Lys-DGlu-Pro-Tyr-Arg- Cit-Cys-Arg-NH$_2$ TF11 was manufactured by the same method as Manufacturing Example 40.

However, after removing Fmoc group from the protected polypeptide resin by 20% piperidine/DMF treatment, the resulting polypeptide resin was hemiglutarylated by glutaric anhydride (5 eq)/pyridine treatment, and treated by 1 M TMSBr-thioanisole/TFA(trifluoroacetic acid) mixture (in the presence of m-cresol (100 eq), ethanedithiol (300 eq)) at 25° C. for 3 hours.

Manufacturing Example 42

Manufacturing of Polypeptide TF12

(TF12: deaminoTMG-APA-TE14011 (2-14))
                                    [SEQ ID NO: 52]
deaminoTMG-APA-Arg-Nal-Cys-Tyr-Cit-Lys-DGlu-Pro- Tyr-Arg-Cit-Cys-Arg-NH$_2$ TF12 was manufactured by the same method as Manufacturing Example 24.

However, instead of Arg(Pbf) of the 1-position, Fmoc-5-aminopentanoic acid was introduced after the introduction of the amino acids from the 13-postion through the 1-position. Furthermore, after removing Fmoc group from the protected polypeptide resin by 20% piperidine/DMF treatment, the resulting polypeptide resin was tetramethylguanylated by 2-(1H-benzotriazole-1-yl)-1,1,3,3-tetramethyluronium tetrafluoroborate (5 eq)/DMF treatment, and treated by 1 M TMSBr-thioanisole/TFA(trifluoroacetic acid) mixture (in the presence of m-cresol (100 eq), ethanedithiol (300 eq)) at 25° C. for 3 hours.

Manufacturing Example 43

Manufacturing of Polypeptide TF15

(TF15: R-CH2NH-RTE14011)
                                    [SEQ ID NO: 55]
R-CH2-Arg-Nal-Cys-Tyr-Cit-Lys-DGlu-Pro-Tyr-Arg-

Cit-Cys-Arg-NH$_2$

TF15 was manufactured by the same method as Manufacturing Example 24.

However, at the 1-position, Fmoc-Arg(Pbf)-H (aldehyde) was condensed by reductive amidation (NaB(CN)H3 (3 eq), AcOH (1 eq)/DMF) instead of the condensation of Fmoc-Arg

Manufacturing Example 44

Manufacturing of Polypeptide TF17

(TF17: TE14011 (2-14))
[SEQ ID NO: 56]
H-Arg-Nal-Cys-Tyr-Cit-Lys-DGlu-Pro-Tyr-Arg-Cit-Cys-Arg-NH$_2$ (TF17)

TF17 was manufactured by the same method as Manufacturing Example 24.

However, arginine of the 1-position was not condensed.

Manufacturing Example 45

Manufacturing of Polypeptide TF18

(TF18: TMguanyl-TC14012)
[SEQ ID NO: 57]
TMguanyl-Arg-Arg-Nal-Cys-Tyr-Cit-Lys-DCit-Pro-Tyr-Arg-Cit-Cys-Arg-NH$_2$ TF18 was manufactured by the same method as Manufacturing Example 9.

However, after removing Fmoc group from the protected polypeptide resin by 20% piperidine/DMF treatment, the resulting polypeptide resin was tetramethylguanylated by 2-(1H-benzotriazole-1-yl)-1,1,3,3-tetramethyluronium tetrafluorob orate (5 eq)/DMF treatment, and treated by 1 M TMSBr-thioanisole/TFA (trifluoroacetic acid) mixture (in the presence of m-cresol (100 eq), ethanedithiol (300 eq)) at 25° C. for 3 hours.

Manufacturing Example 46

Manufacturing of Polypeptide TF19

(TF19: ACA-TC14012)
[SEQ ID NO: 58]
ACA-Arg-Arg-Nal-Cys-Tyr-Cit-Lys-DCit-Pro-Tyr-Arg-Cit-Cys-Arg-NH$_2$

TF19 was manufactured by the same method as Manufacturing Example 9.

However, next to Arg(Pbf) of the 1-position, Fmoc-6-aminohexanoic acid was introduced after the introduction of the amino acids from the 13-postion through the 1-position.

Manufacturing Example 47

Manufacturing of Polypeptide TF20

(TF20: ACA-T140)
[SEQ ID NO: 59]
ACA-Arg-Arg-Nal-Cys-Tyr-Arg-Lys-DLys-Pro-Tyr-Arg-Cit-Cys-Arg-OH

TF20 was manufactured by the same method as Manufacturing Example 17.

However, DLys(Boc) replaced DGlu(O-t-Bu) of the 8-position, and Fmoc-6-aminohexanoic acid replaced Arg (Pbf) of the 1-position respectively after the introduction of the amino acids from the 12-postion through the 1-position.

Manufacturing Example 48

Manufacturing of Polypeptide TZ14011

(TZ14011)
[SEQ ID NO: 60]
H-Arg-Arg-Nal-Cys-Tyr-Cit-Arg-DLys-Pro-Tyr-Arg-Cit-Cys-Arg-NH$_2$

TZ14011 was manufactured by the same method as Manufacturing Example 24. However, DLys(Boc) replaced DGlu (O-t-Bu) of the 8-position, and Arg (Pbf) replaced Lys (Boc) of the 7-position respectively during the introduction of the amino acids from the 13-postion through the 1-position.

Manufacturing Example 49

Manufacturing of Polypeptide AcTZ14011

(AcTZ14011)
[SEQ ID NO: 61]
Ac-Arg-Arg-Nal-Cys-Tyr-Cit-Arg-DLys-Pro-Tyr-Arg-Cit-Cys-Arg-NH$_2$

AcTZ14011 was manufactured by the same method as Manufacturing Example 48.

However, after removing Fmoc group from the protected polypeptide resin by 20% piperidine/DMF treatment, the resulting polypeptide resin was acetylated by acetic anhydride (100 eq)-pyridine (100 eq)/DMF treatment, and treated by 1M TMSBr-thioanisole/TFA(trifluoroacetic acid) mixture (in the presence of m-cresol (100 eq), ethanedithiol (300 eq)) at 25° C. for 3 hours.

Manufacturing Example 50

Manufacturing of Polypeptide TN14003

(TN14003)
[SEQ ID NO: 1]
H-Arg-Arg-Nal-Cys-Tyr-Cit-Lys-DLys-Pro-Tyr-Arg-Cit-Cys-Arg-NH$_2$

TN14003 was manufactured by the same method as Manufacturing Example 9. However, DLys(Boc) replaced DCit of the 8-position during the introduction of the amino acids from the 13-postion through the 1-position.

Manufacturing Example 51

Manufacturing of Polypeptide TN14005

(TN14005)
[SEQ ID NO: 1]
H-Arg-Arg-Nal-Cys-Tyr-Arg-Lys-DCit-Pro-Tyr-Arg-Cit-Cys-Arg-NH$_2$

TN14005 was manufactured by the same method as Manufacturing Example 9. However, Arg(Pbf) replaced Cit of the 6-position during the introduction of the amino acids from the 13-postion through the 1-position.

Manufacturing Example 52

Manufacturing of Polypeptide AcTN14003

(AcTN14003)
[SEQ ID NO: 62]
Ac-Arg-Arg-Nal-Cys-Tyr-Cit-Lys-DLys-Pro-Tyr-Arg-

Cit-Cys-Arg-NH₂

AcTN14003 was manufactured by the same method as Manufacturing Example 50. However, after removing Fmoc group from the protected polypeptide resin by 20% piperidine/DMF treatment, the resulting polypeptide resin was acetylated by acetic anhydride (100 eq)-pyridine (100 eq)/DMF treatment, and treated by 1 M TMSBr-thioanisole/TFA (trifluoroacetic acid) mixture (in the presence of m-cresol (100 eq), ethanedithiol (300 eq)) at 25° C. for 3 hours.

Manufacturing Example 53

Manufacturing of Polypeptide AcTN14005

(AcTN14005)
[SEQ ID NO: 63]
Ac-Arg-Arg-Nal-Cys-Tyr-Arg-Lys-DCit-Pro-Tyr-Arg-

Cit-Cys-Arg-NH₂

AcTN14005 was manufactured by the same method as Manufacturing Example 51. However, after removing Fmoc group from the protected polypeptide resin by 20% piperidine/DMF treatment, the resulting polypeptide resin was acetylated by acetic anhydride (100 eq)-pyridine (100 eq)/DMF treatment, and treated by 1 M TMSBr-thioanisole/TFA (trifluoroacetic acid) mixture (in the presence of m-cresol (100 eq), ethanedithiol (300 eq)) at 25° C. for 3 hours.

Manufacturing Example 54

Manufacturing of Polypeptide 4F-benzoyl-TN14003

(4F-benzoyl-TN14003)
[SEQ ID NO: 64]
4F-benzoyl-Arg-Arg-Nal-Cys-Tyr-Cit-Lys-DLys-Pro- Tyr-Arg-Cit-Cys-Arg-NH₂

1. Synthesis of 4F-Benzoyl-Tn14003 Protected Polypeptide Resin:

After removing Fmoc group from Fmoc-Rink amide resin (0.34 mmol/g) 2.94 g (1 mmol) by 20% piperidine/DMF, Fmoc-Arg(Pbf)-OH (2.5 eq) corresponding to the 14-position was added, and condensation reaction by DIPCDI-HOBt method was conducted in DMF. The progress of the condensation reaction was monitored by ninhydrin test of Kaiser, E. et al. (Anal. Biochem. 34: 595 (1970)).

2. Introduction of Amino Acids of the 13-Position to 1 Position:

Similarly to the foregoing, Cys(Trt), Cit, Arg(Pbf), Tyr(t-Bu), Pro, DLys(Boc), Lys(Boc), Cit, Tyr(t-Bu), Cys(Trt), Nal, Arg(Pbf), Arg(Pbf) residue was sequentially introduced into Rink amide resin, 4-fluorobenzoic acid (2.5 eq) was condensed at the last N-terminal by DIPCDI-HOBt method and the protected polypeptide resin was obtained.

3. Deprotection and Clearage of Polypeptide from Resin and Purification:

The protected polypeptide resin (1 mmol) was treated by 270 mL of 1 M TMSBr-thioanisole/TFA(trifluoroacetic acid) mixture (in the presence of m-cresol (100 eq), ethanedithiol (300 eq)) at 25° C. for 3 hours. The resin was separated by filtration from the reaction mixture, washed with TFA 5 mL twice, the mixture of the filtrate and the wash solution was subjected to concentration in vacuo. The remaining residue was added with 300 mL of water-cooled dry ether, the resultant sediment was separated from supernatant liquid by centrifugal sedimentation and decantation. The obtained residue was cleansed by cold ether, dissolved into 500 mL of 1 N acetic acid, and diluted to 2.5 L by distilled water.

4. Cyclization by Air Oxidation:

Diluted water solution of the above-mentioned polypeptide was adjusted to pH 7.5 by concentrated ammonia water, and was cyclized by ventilated air oxidation. This water solution was purified by preparative HPLC(COSMOSIL 5C18 AR-II column: acetonitrile water) and gel filtration chromatography (Sephadex G-15, eluate: 0.1 N AcOH), a polypeptide of a single peak was obtained and freeze-dried. The purity was confirmed by HPLC.

Yield: 551.5 mg (6 TFA salt) (19.4%)

$[\alpha]D28.6=-10.25$ (c 0.39, H2O)

Ionspray mass spectrum (IS-MS): $C_{97}H_{144}FN_{33}O_{19}S_2$

Calculated Value: 2159.52 Actual Measurement Value: 2161

(triple stage quadrupole mass spectrometry API-IIIE (Sciex))

Manufacturing Example 55

Manufacturing of Polypeptide
4F-benzoyl-TE14011-Me (4F-benzoyl-TE14011-Me)
[SEQ ID NO: 1]
4-fluorobenzoyl-Arg-Arg-Nal-Cys-Tyr-Cit-Lys-DGlu- Pro-Tyr-Arg-Cit-Cys-Arg-NHMe 1. Synthesis of 4F-Benzoyl-TE14011-Me Protected Polypeptide Resin:

4-sulfamylbutyryl AM NovaGel resin was added with Fmoc-Arg(Pbf)-OH (4 eq) corresponding to the 14-position, and, in CHCl₃, condensation reaction by PyBOP (3 eq)-DIPEA (6 eq) method was conducted at 0° C. (This condensation reaction was repeated twice). After removing Fmoc group by 20% piperidine/DMF, Fmoc-Cys(Trt)-OH (2.5 eq) corresponding to the 13-position was added, and condensation reaction by DIPCDI-HOBt method was conducted in DMF. The degree of the progress of the condensation reaction was monitored by ninhydrin test of Kaiser, E. et al. (Anal. Biochem., 34: 595 (1970)). Similarly to the foregoing for the introduction of amino acids from the 12-position to the 1-position, Cit, Arg(Pbf), Tyr(t-Bu), Pro, DGlu(O-t-Bu), Lys(Boc), Cit, Tyr(t-Bu), Cys(Trt), Nal, Arg(Pbf), Arg(Pbf) residue was sequentially introduced into the sulfamylbutyryl resin, 4-fluorobenzoic acid (2.5 eq) was condensed at the last N-terminal by DIPCDI-HOBt method to yield the protected polypeptide resin.

2. C-Terminal Alkylamidation, Deprotection and Clearage of Polypeptide from Resin and Purification:

The protected polypeptide resin was cyanomethylated by ICH2CN (40 eq), DIPEA (10 eq)/NMP treatment (48 hours), then, treated by methylamine (excess) in THF/DMF, and the protected C-terminally methylamidated polypeptide was isolated from the resin. The protected polypeptide was treated by 1 M TMSBr-thioanisole/TFA(trifluoroacetic acid) mixture (in the presence of m-cresol (100 eq), ethanedithiol (300 eq)) at 25° C. for 3 hours. The reaction solution was subjected to concentration in vacuo, the remaining residue was added with water-cooled dry ether, the resultant sediment was separated from supernatant liquid by centrifugal sedimentation and decantation. The obtained residue was cleansed by cold ether, dissolved into 1N acetic acid, and diluted by distilled water.

3. Cyclization by Air Oxidation:

Diluted water solution of the above-mentioned polypeptide was adjusted to pH 7.5 by concentrated ammonia water, and was cyclized by ventilated air oxidation. This water solution was purified by preparative HPLC(COSMOSIL 5C18 AR-II column: acetonitrile water) and gel filtration chromatography (Sephadex G-15, eluate: 0.1 N AcOH), a polypeptide of a single peak was obtained and freeze-dried. The purity was confirmed by HPLC.

Manufacturing Example 56

Manufacturing of Polypeptide
4F-benzoyl-TE14011-Et (4F-benzoyl-TE14011-Et)
[SEQ ID NO: 1]
4-fluorobenzoyl-Arg-Arg-Nal-Cys-Tyr-Cit-Lys-DGlu- Pro-Tyr-Arg-Cit-Cys-Arg-NHEt 4F-benzoyl-TE14011-Et was manufactured by the same method as Manufacturing Example 55. However, ethylamine replaced methylamine Manufacturing Example 57

Manufacturing of Polypeptide
4F-benzoyl-TE14011-iPr (4F-benzoyl-TE14011-iPr)
[SEQ ID NO: 1]
4-fluorobenzoyl-Arg-Arg-Nal-Cys-Tyr-Cit-Lys-DGlu- Pro-Tyr-Arg-Cit-Cys-Arg-NHiPr 4F-benzoyl-TE14011-iPr was manufactured by the same method as Manufacturing Example 55. However, isopropylamine replaced methylamine Manufacturing Example 58

Manufacturing of Polypeptide
4F-benzoyl-TE14011-tyramine (4F-benzoyl-TE14011-tyramine)
[SEQ ID NO: 1]
4-fluorobenzoyl-Arg-Arg-Nal-Cys-Tyr-Cit-Lys-DGlu- Pro-Tyr-Arg-Cit-Cys-Arg-tyramine 4F-benzoyl-TE14011-tyramine was manufactured by the same method as Manufacturing Example 55. However, tyramine (p-hydroxyphenylethylamine) replaced methylamine Experimental Example 1

The Inhibitory Activity of the Peptides of the Present Invention Against CXCL12 Binding to CXCR4 Receptor 50 μL of Jurkat human T-cell leukemia cells ($6 \times 10^6$ cells/mL) suspended in buffer (Dulbecco's PBS solution (pH 7.0) containing 0.5% BSA, 20 mM HEPES), 25 μL of test compounds (Table 1: each compound being synthesized in the form of acetate salt) diluted by buffer and 25 μL of 200 pM 125I-CXCL12 solution were respectively dispensed to each well of the plate, and were subjected to fixation reaction for 1 hour at room temperature. After reaction, suction was made toward the reaction solution by 96 well GF/C filter plate, and each well's radioactivity was measured by top count. As the radioactivity index of 100% when the test compound was not added, and 0% when 100 nM of non-radioisotope-labeled CXCL12 was added, the inhibitory activity of each test compound was measured. The result is indicated in the following Table 1.

| No. | IC50 (nM) | No. | IC50 (nM) | No. | IC50 (nM) |
|---|---|---|---|---|---|
| TE14002 | 680 | TF1 | 11 | TF11 | 630 |
| TE14003 | 5 | TF2 | 3.3 | TF12 | 4.6 |
| TE14004 | 6.8 | TF3 | 9.6 | TF13 | 21 |
| TE14005 | 2.2 | TF4 | 9.9 | TF14 | 49 |
| TE14006 | 5.6 | TF5 | 2.8 | TF15 | 95 |
| TE14011 | 2.9 | TF6 | 3.9 | TF17 | 79 |
| TE14012 | 5.4 | TF7 | 5.7 | TF18 | 8 |
| TE14013 | 9.3 | TF8 | 8.2 | TF19 | 4.5 |
| 4F-benzoyl-TN14003 | 0.99 | TF9 | 250 | TF20 | 3.5 |
|  |  | TF10 | 48 |  |  |

The results indicated in Table 1 shows that the compounds have potent binding inhibitory activity.

Experimental Example 2

The Inhibitory Activity of TE-14005 Against Breast Cancer Cell Migration Induced by CXCL12

Transwell filter (polycarbonate filter, 8 μm diameter, Costar Company) was treated at 37° C. for 6 hours in 10 μg/mL fibronectin solution and air-dried. 100 nM of CXCL12 (R&D System Company) and 600 μL/well of buffer-A (0.1% bovine serum albumin, DMEM (GibcoBRL) containing 12 mM HEPES) containing the test compound were added to the lower chamber of the Transwell. The test compound and human breast cancer MDA-MB-231 cells (purchased from American Tissue Culture Collection), and 100 μL/well of buffer A containing $2\times10^6$ cells/mL were added to the upper chamber. After 15 hours' incubation at 37° C. in 5% $CO_2$ incubator, the upper surface of the filter was wiped and the cell was removed, and then the cell on the lower surface of the filter was fixed and stained with 25% methanol solution containing 0.5% crystal violet (Wako Pure Chemical Ind.), washed by distilled water and air-dried. Cutting off the filter part, adding 0.1 M sodium citrate/50% ethanol solution, and eluting crystal violet absorption at 550 nm was measured. The result is indicated in FIG. 1. Control (−) indicates the migration when CXCL12 was not added. By adding CXCL12, the migration of MDA-MB-231 cells was enhanced. This CXCL12-induced migration of MDA-MB-231 cells was inhibited by 10 nM of the antagonist, TE14005.

Experimental Example 3

The Inhibitory Activity of TC14012 and TN14003 Against CXCL12Binding to CXCR4 Receptor 50 μL of Jurkat human T-cell leukemia cells ($6\times10^6$ cells/mL) suspended in buffer (Dulbecco's PBS solution (pH 7.0) containing 0.5% BSA, 20 mM HEPES), 25 μL of test compounds (Table 2: each compound being synthesized in the form of acetate salt) diluted by buffer and 25 μL of 200 p M 125I-CXCL12 solution were respectively dispensed to each well of the plate, and were subjected to fixation reaction for 1 hour at room temperature. After reaction, suction was made toward the reaction solution by 96 well GF/C filter plate, and each well's radioactivity was measured by top count. As the radioactivity index of 100% when the test compound was not added, and 0% when 100 nM of non-radioisotope-labeled CXCL12 was added, the inhibitory activity of each test compound was measured. The result is indicated in the following Table 2.

| No. | IC50 (nM) |
|---|---|
| TC14012 | 2.7 |
| TN14003 | 2.6 |

The result indicated in Table 2 shows that the compounds have potent binding inhibitory activity.

Experimental Example 4

The Inhibitory Activity of TC-14012 Against Breast Cancer Cell Migration Induced by CXCL12

Transwell filter (polycarbonate filter, 8 μm diameter, Costar Company) was treated at 37° C. for 6 hours in 10 μg/mL fibronectin solution and air-dried. 100 nM of CXCL12 (R&D System Company) and 600 μL/well of buffer-A (0.1% bovine serum albumin, DMEM (GibcoBRL) containing 12 mM HEPES) containing the test compound were added to the lower chamber of the Transwell. The test compound and human breast cancer MDA-MB-231 cells (purchased from American Tissue Culture Collection), and 100 μL/well of buffer A containing $2\times10^6$ cells/mL were added to the upper chamber.

Figure 2:
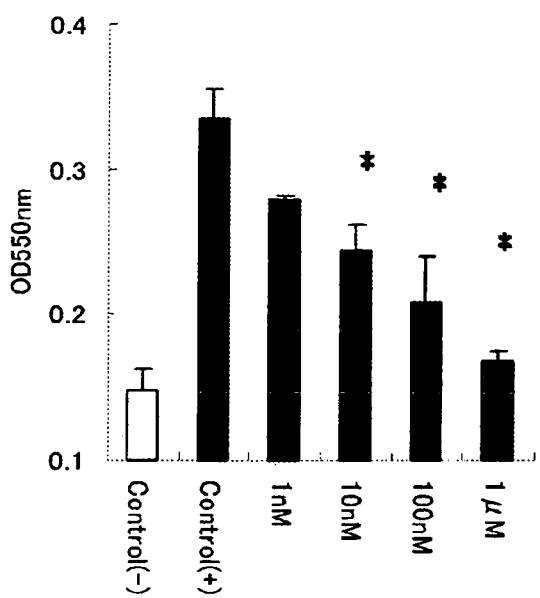
FIG. 2 shows the inhibitory activity of TC-14012 against the migration of breast cancer cells induced by CXCL12. The vertical axis shows the migration of cells (absorption of light: OD550 nm). From the left, it shows the result (mean value±standard deviation, n=2) obtained respectively when CXCL12 was not added (negative control), when CXCL12 was added (positive control), when CXCL12 and TC-14012 1 nM were added, when CXCL12 and TC-14012 10 nM were added, when CXCL12 and TC-14012 100 nM were added, and when CXCL12 and TC-14012 1 μM were added. * indicates the significance of each TC-14012 added group compared with the positive control group (Williams' test, $p \leq 0.025$).

After 15 hours' incubation at 37° C. in 5% $CO_2$ incubator, the upper surface of the filter was wiped and the cell was removed, and then the cell on the lower surface of the filter was fixed and stained with 25% methanol solution containing 0.5% crystal violet (Wako Pure Chemical Ind.), washed by distilled water and air-dried. Cutting off the filter part, adding 0.1 M sodium citrate/50% ethanol solution, and eluting crystal violet absorption at 550 nm was measured. The result is indicated in FIG. 2. Control (−) indicates the migration when CXCL12 was not added. By adding CXCL12, the migration of MDA-MB-231 cells was enhanced. This CXCL12-induced migration of MDA-MB-231 cells was inhibited by 10 nM of the antagonist, TE14005.

Experimental Example 5

The Inhibitory Activity of 4Fbenzoyl-TN-14003 Against T-Cell Derived Leukemia Cell Migration Induced by CXCL12

30 nM of CXCL12 (R&D System Company) and 600 μL/well of buffer-A (0.1% bovine serum albumin, DMEM (GibcoBRL) containing 12 mM HEPES) containing the test compound were added to the lower chamber of Transwell filter (polycarbonate filter, 8 μm diameter, Costar Company). The test compound and human cell-derived leukemia SUP-T1 cells (purchased from American Tissue Culture Collection), and 100 μL/well of buffer A containing $2\times10^6$ cells/mL were added to the upper chamber.

Figure 3:
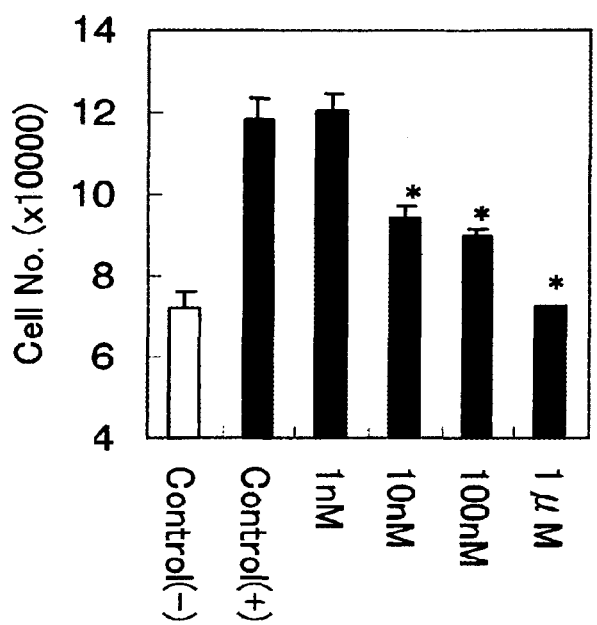
FIG. 3 shows the inhibitory activity of 4Fbenzoyl-TN-14003 against the migration of T-cell originating leukemia cells induced by CXCL12. The vertical axis shows the migration of cells (the number of cells). From the left, it shows the result (mean value±standard deviation, n=2) obtained respectively when CXCL12 was not added (negative control), when CXCL12 was added (positive control), when CXCL12 and 4Fbenzoyl-TN-14003 1 nM were added, when CXCL12 and 4Fbenzoyl-TN-14003 10 nM were added, when CXCL12 and 4Fbenzoyl-TN-14003 100 nM were added, and when CXCL12 and 4Fbenzoyl-TN-14003 1 μM were added. * indicates the significance of each 4Fbenzoyl-TN-14003 added group compared with the positive control group (Williams' test, $p \leq 0.025$).

After 4 hours' incubation at 37° C. in 5% $CO_2$ incubator, the number of the cells moved to the lower chamber was counted by Coulter counter. The result is indicated in FIG. 3. Control (−) indicates the migration when CXCL12 was not added. Control (+) indicates the migration when CXCL12 was added. By adding CXCL12, the migration of SUP-T1 cells was enhanced. This CXCL12-induced migration of SUP-T1 cells was inhibited by 10 nM of the antagonist, 4Fbenzoyl-TN-14003. From the foregoing, 4Fbenzoyl-TN-14003, by inhibiting the movement of T-cells at low concentrations, is considered to be useful as an inhibitory drug for chronic rheumatoid arthritis.

Experimental Example 6

The Inhibitory Activity of 4Fbenzoyl-TN-14003 Against Breast Cancer Cell Migration Induced by CXCL12

Figure 4:
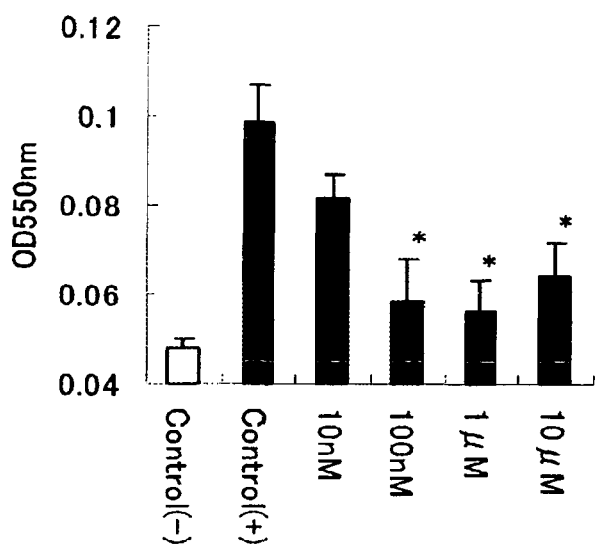
FIG. 4 shows the inhibitory activity of 4Fbenzoyl-TN-14003 against the migration of breast cancer cells induced by CXCL12. The vertical axis shows the migration of cells (absorption of light: OD550 nm). From the left, it shows the result (mean value±standard deviation, n=2) obtained respectively when CXCL12 was not added (negative control), when CXCL12 was added (positive control), when CXCL12 and 4Fbenzoyl-TN-14003 10 nM were added, when CXCL12 and 4Fbenzoyl-TN-14003 100 nM were added, when CXCL12 and 4Fbenzoyl-TN-14003 1 μM were added, and when CXCL12 and 4Fbenzoyl-TN-14003 10 μM were added. * indicates the significance of each 4Fbenzoyl-TN-14003 added group compared with the positive control group (Williams' test, $p \leq 0.025$).

Transwell filter (polycarbonate filter, 8 μm diameter, Costar Company) was treated at 37° C. overnight in 10 mg/mL fibronectin solution and air-dried. 100 nM of CXCL12 (R&D System Company) and 600 μL/well of buffer-A (0.1% bovine serum albumin, DMEM (GibcoBRL) containing 12 mM HEPES) containing 4Fbenzoyl-TN-14003 were added to the lower chamber of Transwell. 4Fbenzoyl-TN-14003 and human breast cancer MDA-MB-231 cells (purchased from American Tissue Culture Collection), and 100 μL/well of buffer A containing $2\times10^6$ cells/mL were added to the upper chamber. The test compound and human breast cancer MDA-MB-231 cells (purchased from American Tissue Culture Collection), and 100 mL/well of buffer A containing $2\times10^6$ cells/mL were added to the upper chamber. After 15 hours' incubation at 37° C. in 5% $CO_2$ incubator, the upper surface of the filter was wiped and the cell was removed, and then the cell on the lower surface of the filter was fixed and stained with 25% methanol solution containing 0.5% crystal violet (Wako Pure Chemical Ind.), washed by distilled water and air-dried. Cutting off the filter part, adding 0.1 M sodium citrate/50% ethanol solution, and eluting crystal violet absorption at 550 nm was measured. The result is indicated in FIG. 4. Control (−) indicates the migration when CXCL12 was not added. Control (+) indicates the migration when CXCL12 was added. By adding CXCL12, the migration of MDA-MB-231 cells was enhanced. This CXCL12-induced migration of MDA-MB-231 cells was inhibited by 10 nM of the antagonist, 4Fbenzoyl-TN-14003.

Experimental Example 7

Anti-Metastatic Activity of 4Fbenzoyl-TN-14003

Figure 5:
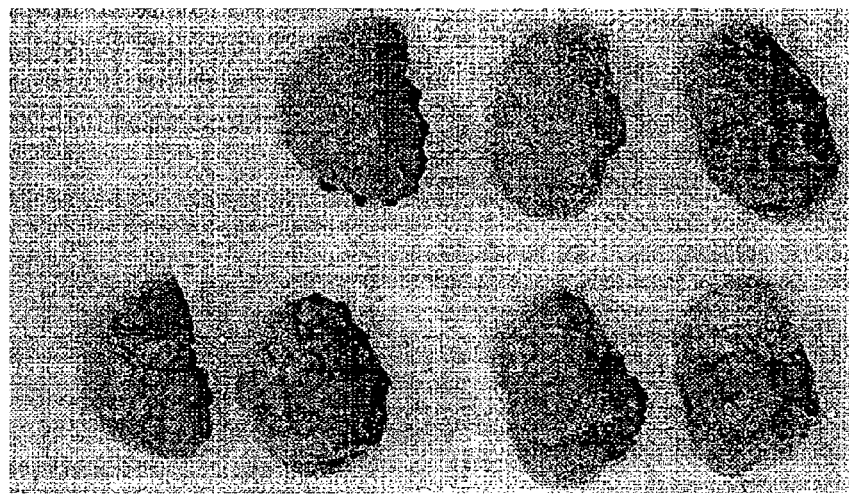
FIGS. 5A-5B are chromatic figures of lung tissue displaying the inhibitory activity of 4Fbenzoyl-TN-14003 in a mouse transplanted with human breast cancer cells.
Figure 5:
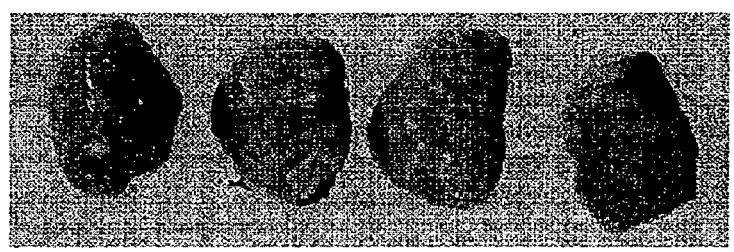

MDA-MB-231 human breast cancer cells ($10^6$ cells) were implanted intravenously into the tails of five week-old female CB-17 SCID mice (Crea Japan, Inc.). 4Fbenzoyl-TN-14003 was prepared at 80 mg/mL in physiologic saline solution, was included into sustained-releasing osmotic pumps (Alzet pump, Alza Corporation, usable for 2 week sustained-release; the dose was equivalent to 18.2 mg/kg/day), and was intradermally loaded to the backs of the mice on the date immediately preceding the implantation. Further, 14 days after the implantation, Alzet pumps containing an equal dose of the drug were additionally loaded. To the control group, Alzet pumps injected with physiological saline solution were additionally loaded. 28 days after the implantation, the mice were dissected, about 2 mL of 0.2% Evans' Blue solution was injected through windpipes, and lungs were stained. The lungs were taken out, soaked in Bouin's liquid, stained and fixed. By eye observation of metastatic focus (yellow stained potion), the evaluation was conducted to determine whether or not the compound exhibited more evident anti-metastatic activity. The result is indicated in FIG. 5. In the lungs of the control group, the yellow stained portions were evenly seen, and lung metastasis was observed. On the other hand, in the 4Fbenzoyl-TN-14003 administration group, yellow stained specimens were less. Comparatively, the metastasis was inhibited by 4Fbenzoyl-TN-14003.

Experimental Example 8

The Inhibitory Activity of 4Fbenzoyl-TN-14003 Against CXCL12-Induced Migration of Human Cell Lines (Jurkat) and Mouse Splenocytes 1. Effects on the Migrating Reaction of Human T-Cell Lines:
RPMI-1640 and fetal calf serum (FCS) was purchased from BioWhittaker, penicillin-streptomycin solution, RPMI-1640 (without phenol red) and HEPES from Invitrogen, BSA from Sigma, and, human SDF-1α (CXCL12) from Genzyme. Jurkat human T lymphocyte cell lines were purchased from ATCC and incubated in RPMI-1640 10% FCS. 4Fbenzoyl-TN14003 was dissolved to PBS and used for experiments.

Using 24-wells Transwell (Costar, polycarbonate membrane, pore size 5 μm), migrating reaction was performed. 600 μL of SDF-1α (final concentration 1 ng/mL) was added to the lower layer of Transwell, $5 \times 10^5$ cells (200 μL) was added to the insert, and was reacted at 37° C. for 4 hours. The cells were pre-incubated with drugs at 37° C. for 30 minutes. The migrating reaction was made in RPMI-1640 culture media containing 20 mmol/L HEPES, 0.5% BSA. The cells migrated to the lower layer were recovered, and the number of the cells was counted by Coulter Counter. The inhibitory rate (%) against the migration by the drug of each concentration was calculated by the following formula, and $IC_{50}$ value was calculated from such inhibitory rate.

$$\text{inhibition rate } (\%) = 100 \times \left(1 - \frac{\text{the number of migrated cells at the presence of a drug of each concentration} - \text{the number of migrated cells without } SDF-1\alpha}{\text{(the number of migrated cells without a drug} - \text{the number of migrated cells without } SDF-1\alpha)}\right)$$

Figure 6:
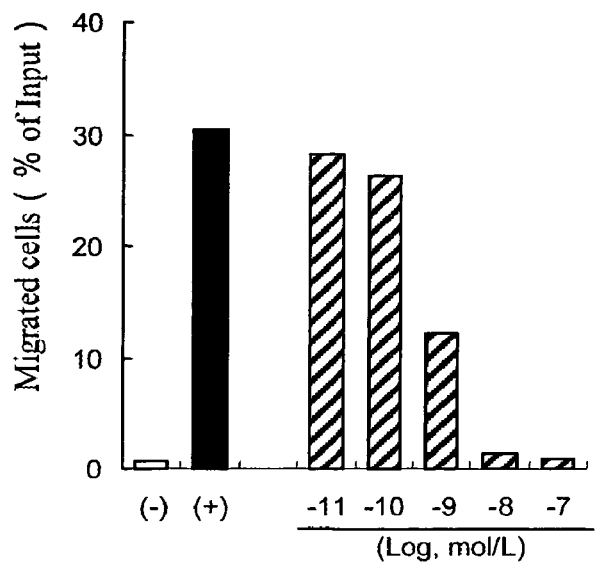
FIG. 6 shows the inhibitory activity of 4Fbenzoyl-TN-14003 against migration of Jurkat cells induced by SDF-1α (CXCL12). The vertical axis shows cell migration (the ratio of migrating cells to the input). From the left, it shows the result obtained respectively when SDF-1α was not added, when SDF-1α was added, when SDF-1α and 4Fbenzoyl-TN-14003 10 μM were added, when SDF-1α and 4Fbenzoyl-TN-14003 100 pM were added, when SDF-1α and 4Fbenzoyl-TN-14003 1 nM were added, when SDF-1α and 4Fbenzoyl-TN-14003 10 nM were added, and when SDF-1α and 4Fbenzoyl-TN-14003 100 nM were added.

As a result, as indicated in FIG. 6, Jurkat cells exhibited strong cell migration reactivity against SDF-1α. 4F-benzoyl-TN14003 inhibited this reaction in a dose-dependent manner, and its $IC_{50}$ value was 0.65 nmol/L.

2. Effects on the Migrating Reaction of Mouse Splenocytes:
Spleens were isolated from BALB/c mice (male, Charles River Japan, Inc.), converted to single cell suspensions, and splenocytes were prepared by crushing red blood cells.

SDF-1α (Peprotech, final concentration 100 ng/mL) was added to the lower layer of Transwell (pore size 5 nm), $1 \times 10^6$/well of the cells (100 μL) were added to the insert, and reacted at 37° C. for 2.5 hours. The cells were incubated with the drug at 37° C. for 30 minutes. Migrating reaction was made in the RPMI-1640 culture media containing 20 mmol/L HEPES, 0.5% BSA. The number of the cells migrated to the lower layer was counted by Coulter Counter. Similarly to the preceding clause, the inhibitory rate against the migration by the drug of each concentration and $IC_{50}$ value were calculated.

Figure 7:
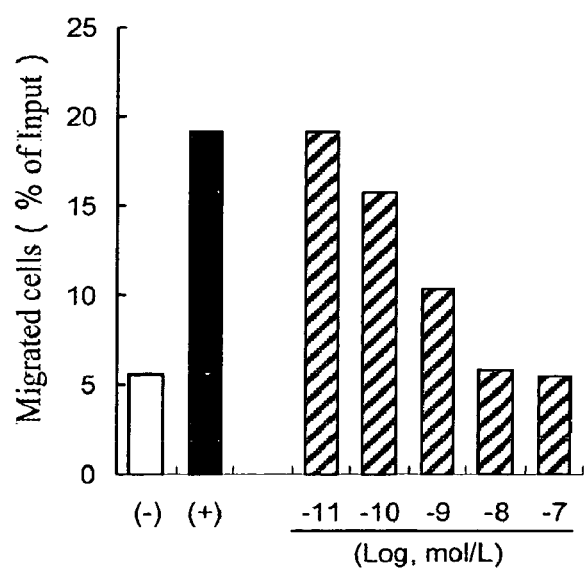
FIG. 7 shows the inhibitory activity of 4Fbenzoyl-TN-14003 against migration of mouse splenocytes induced by SDF-1α (CXCL12). The vertical axis shows cell migration (the ratio of migrating cells to the input). From the left, it shows the result obtained respectively when SDF-1α was not added, when SDF-1α was added, when SDF-1α and 4Fbenzoyl-TN-14003 10 pM were added, when SDF-1α and 4Fbenzoyl-TN-14003 100 pM were added, when SDF-1α and 4Fbenzoyl-TN-14003 1 nM were added, when SDF-1α and 4Fbenzoyl-TN-14003 10 nM were added, and when SDF-1α and 4Fbenzoyl-TN-14003 100 nM were added.

As a result, as indicated in FIG. 7, 4Fbenzoyl-TN14003 inhibited strong migration reactivity of mouse splenocytes induced by SDF-1 in a dose-dependent manner. Its $IC_{50}$ value was 0.54 nmol/L, and it exhibited inhibitory activity comparable to the case of human cells. This means in turn that little species difference was identified between humans and mice with respect to this peptide.

Experimental Example 9

Effects of 4Fbenzoyl-TN-14003 on Mouse Delayed-Type Hypersensitivity Reaction (DTH)

Preserved blood of sheep was purchased from Nippon Bio-Supp. Center. The preserved sheep blood was cleansed twice in physiological saline solution, suspended in physiological saline solution, and used as sheep red blood cells (SRBC). As OD541 nm value of oxyhemoglobin at the time of hemolyzation of $1.0 \times 10^9$ cells/mL of the SRBC suspension by 14 parts distilled water is considered to be nearly 0.700, SRBC density was accordingly fixed.

$2 \times 10^7$ cells/50 μl of SRBC were administered subcutaneously to the ankles of the left hindlimbs of BALB/c mice (male, 6 week-old, Charles River Japan, Inc.) and sentisized. After 5 days, $10^8$ cells/50 μl of SRBC were administered subcutaneously to the ankles of the right hindlimbs and DTH reaction was induced Immediately prior to and 24 hours after the induction of antigens, the thickness of the ankles of the right hindlimbs was measured by a digital micrometer (Mitutoyo Corporation CD-15B), and the increase (mm) in the thickness of ankles was adopted as the indicator of DTH reaction.

4Fbenzoyl-TN14003 was dissolved to PBS, and continuously administered using Alzet osmotic pumps (Alza, 0.5 μL/hr, 7 days persistent type). The osmotic pumps were implanted intradermally to the backs under ether anesthesia on the day before the sensitization. As the control, pumps injected with PBS were similarly implanted. 4F-benzoyl-TN14003 was administered at the doses of 4.8, 24 and 120 μg/day.

Data were expressed as mean value±s tandard margin of error (n=7). By Williams test, p≦0.025 was valued as significant.

Figure 8:
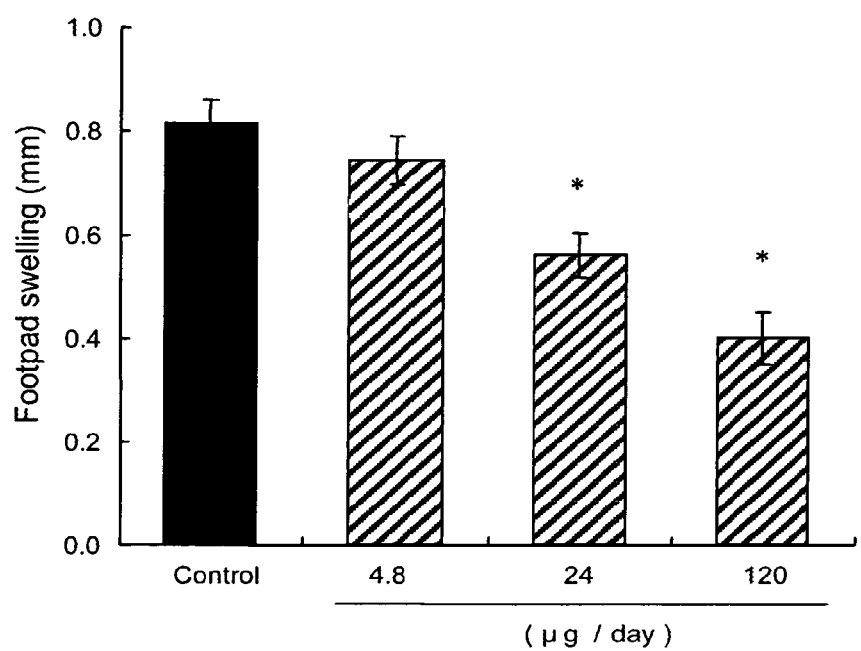
FIG. 8 shows the inhibitory activity of 4Fbenzoyl-TN-14003 against mouse DTH reaction induced by SRBC. The vertical axis shows the increase of footpad thickness of by swelling (mean value±standard margin of error, n=7). From the left, it shows the result each of PBS administration (control) group, 4Fbenzoyl-TN-14003 48 μg per-day administration group, 4Fbenzoyl-TN-14003 24 μg per-day administration group, and 4Fbenzoyl-TN-14003 120 μg per-day administration group. * is $P \leq 0.025$ (comparison with PBS administration group; Williams' test).

As a result, as indicated in FIG. 8, 4F-benzoyl-TN14003 (4.8, 24 and 120 μg/day) inhibited footpad edema dose-dependently and significantly, and the inhibitory rates were 9, 31 and 51%, respectively. This suggests that CXCR4 plays an important role in cellular immunity such as DTH reaction.

Experimental Example 10

Therapeutic Effects of 4Fbenzoyl-TN-14003 on Mouse Collagen-Induced Arthritis

FK-506 was purified by a known method (Kino T. et al., J. Antibiot., 1987 40(9): 1249-55). Methotrexate was purchased from Wako Pure Chemical Ind., indomethacin from Sigma, bovine type II collagen from Collagen Research Center (Tokyo, Japan), Freund's complete adjuvant (FCA from Difco), and anti-mouse IgG2a antibody from Zymed, respectively.

Bovine type II collagen was dissolved to the 2 mg/mL concentration by 0.05 mol/L of acetic acid solution, emulsion was prepared with an equal volume of FCA. 50 μL of the emulsion was injected intradermally at the base of the tail DBA/LIN mouse (male, 6 week old, Charles River Japan, Inc.) and sensitized. 21 days after the injection, additional immunization was made similarly. For 2 weeks after the additional immunization, body weights and hindlimb thickness were measured and arthritis scoring was made. Arthritis scores were scored at 0-3 points of each limb, and evaluated by the total of the same (12 points being the full points; 0, normal; 1, mild swelling or swelling of a single digit; 2, moderate swelling or swelling of plural digits; 3, severe swelling). Two weeks after the immunization, four limbs and sera were picked.

After coat blocking bovine type II collagen (10 μg/mL PBS solution) on the immunoplate, 100 μL of 1000 times diluted mouse serum was added, and kept at room temperature for 2 hours. After cleansing, anti-mouse IgG2a antibody (1000 times dilution) was added. After cleansing, TMB was added, kept at room temperature for 30 minutes, $H_2SO_4$ of equal amount was added, and A450 nm was measured.

Indomethacin (1 mg/kg), methotrexate (3 mg/kg) and FK-506 (10 mg/kg) were suspended to 0.5% methyl cellulose, and orally administered every day for 2 weeks from the day of the additional immunization at the dose of 0.1 mL/10 g body weight. 0.5% methyl cellulose solution of the equal dose was orally administered to the control group. 4Fbenzoyl-TN14003 was dissolved to PBS, and continuously administered using Alzet osmotic pumps (Alza, 0.5 μL/hr 2 weeks). The osmotic pumps were implanted intradermally to the backs of the mice under ether anesthesia on the day before the additional immunization. As the control, pumps injected with PBS were similarly implanted. Evaluation of each drug was made for the value obtained 2 weeks after the additional immunization.

Data were expressed as mean value±standard margin of error (n=8-12). Comparison between 2 groups was made by Student's t-test, p≦0.05 was valued as significant. Multiple comparison was made by Dunnett test, p≦0.05 was valued as significant.

Figure 9:
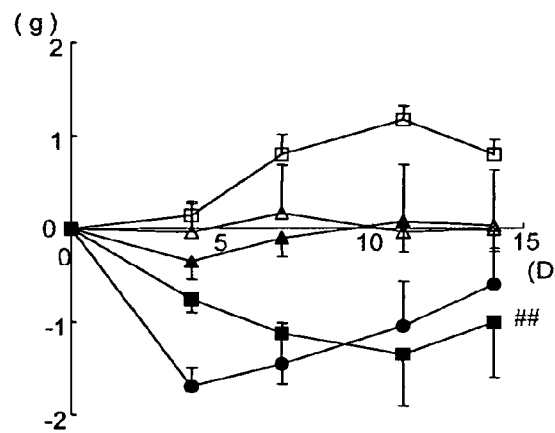
FIGS. 9A-9F show the effects of known medicines against mouse collagen arthritis.
Figure 9:
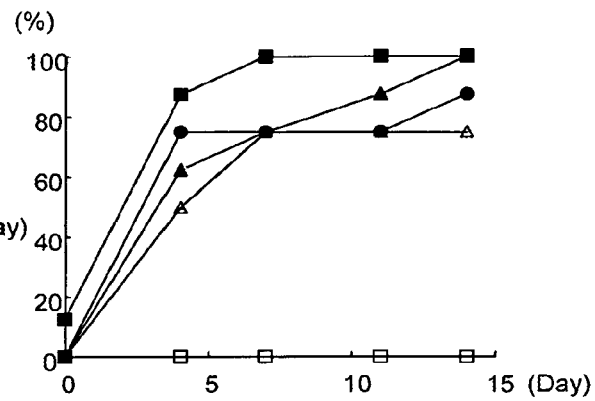
Figure 9:
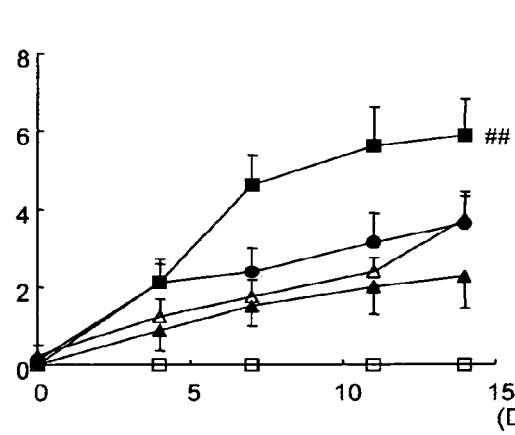
Figure 9:
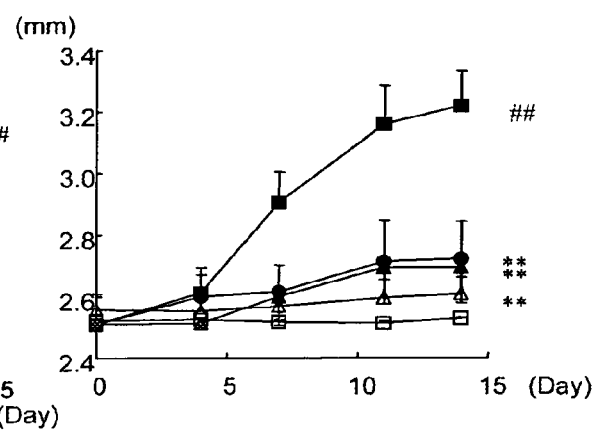
Figure 9:
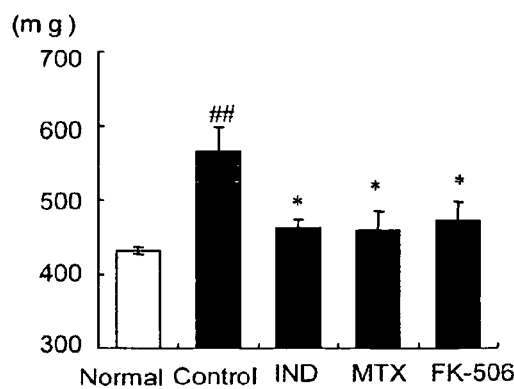
Figure 9:
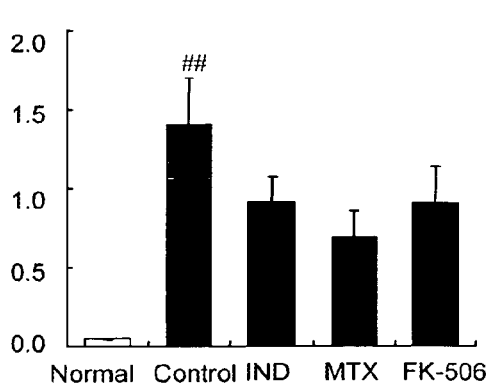
Figure 10A:
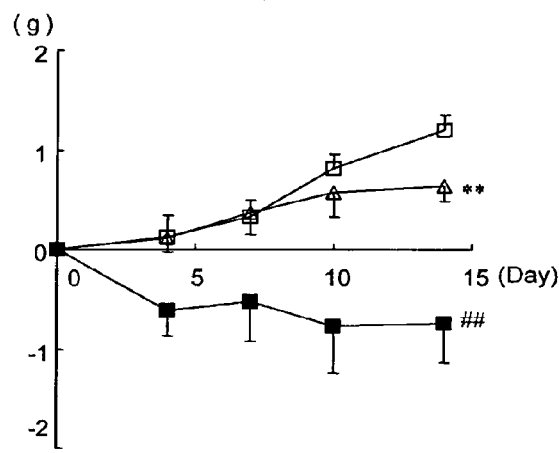
FIGS. 10A-10F show the activity of 4Fbenzoyl-TN-14003 on mouse collagen-induced arthritis.
Figure 10B:
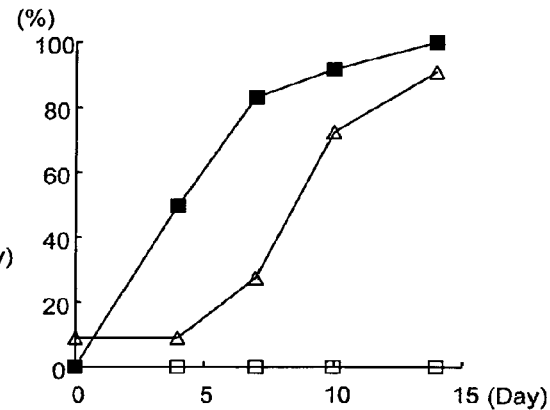
Figure 10C:
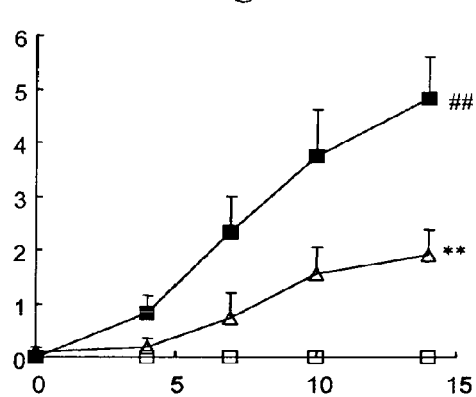
Figure 10D:
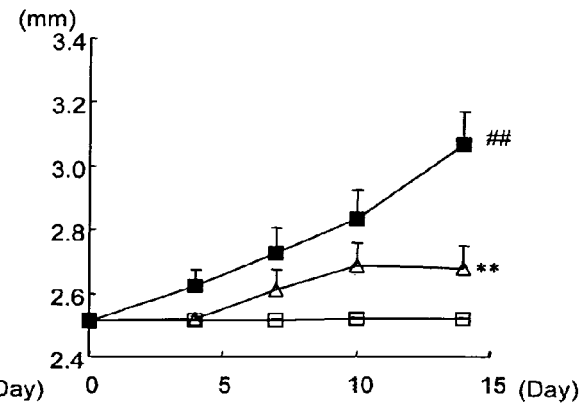
Figure 10E:
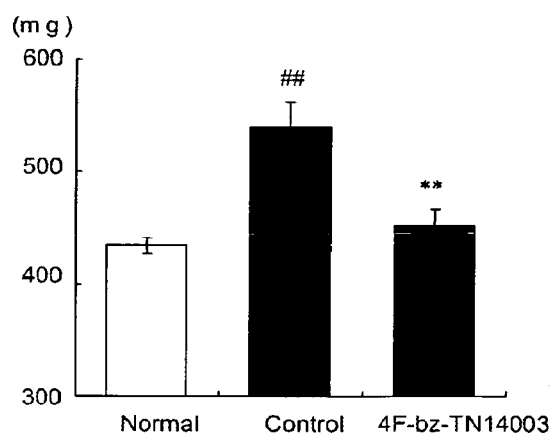
Figure 10F:
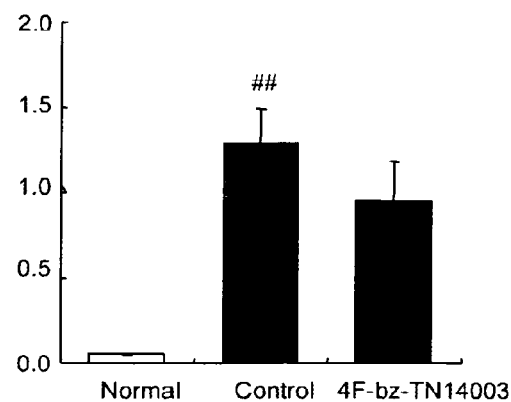

As a result, all of Indomethacin (1 mg/kg, p.o.), methotrexate (3 mg/kg, p.o.) and FK-506 (10 mg/kg, p.o.) significantly inhibited hindlimb swelling, and exhibited significant or evident inhibitory activity against arthritis score (FIG. 9).

4F-benzoyl-TN14003 (120 μg/day) exhibited significant inhibitory activity against hindlimb swelling, arthritis score and body weight loss. It also showed an inhibitory tendency against increase of anti-type II collagen specific IgG2a antibody value (FIG. 10). These inhibitory effects were equivalent to or better than those of the above-mentioned known drugs.

INDUSTRIAL APPLICABILITY

The peptidic compounds of the present invention having CXCR4 antagonistic activity can inhibit the interaction of CXCR4 and CXCL12/SDF-1α, and accordingly, can inhibit the migrating reaction of cancerous cells of cancers impressing CXCR4, for example, oral cancer, throat cancer, lip cancer, lingual cancer, gingival cancer, nasopharyngeal cancer, esophageal cancer, gastric cancer, small intestinal cancer, large intestinal cancer including colorectal cancer, liver cancer, gallbladder cancer, pancreatic cancer, nasal cancer, lung cancer, bone cancer, soft tissue cancer, skin cancer, melanoma, breast cancer, uterine cancer, ovarian cancer, prostate cancer, testicular cancer, penile cancer, bladder cancer, kidney cancer, brain cancer, thyroid cancer, lymphoma, leukemia, etc., and are useful as drugs for the prevention and/or therapy of these cancers. Also, the peptidic compounds of the present invention can inhibit the migrating reaction of immunocytes induced by CXCL12/SDF-1α and are useful as drugs for the prevention and/or therapy of chronic rheumatoid arthritis.

The invention claimed is:

1. The peptide 4F-benzoyl-Arg-Arg-NaI-Cys-Tyr-Cit-Lys-DLys-Pro-Try-Arg-Cit-Cys-Arg-NH$_2$, or salt thereof.

2. A pharmaceutical composition comprising the peptide as defined in claim 1, or a salt thereof, and a pharmaceutically acceptable carrier or excipient.

3. A method for treating cancer selected from the group consisting of lung cancer, leukemia and breast cancer, reducing metastasis or treating chronic rheumatoid arthritis in a subject in need thereof, the method comprising administering to the subject a pharmaceutical composition comprising as an active ingredient a therapeutically effective amount of the peptide according to claim 1.

* * * * *